(12) United States Patent
Look et al.

(10) Patent No.: US 11,540,847 B2
(45) Date of Patent: Jan. 3, 2023

(54) SYSTEMS AND METHODS FOR MANAGEMENT OF THROMBOSIS

(71) Applicant: INCUVATE, LLC, Irvine, CA (US)

(72) Inventors: David M. Look, Newport Beach, CA (US); Bradley S. Culbert, Mission Viejo, CA (US)

(73) Assignee: Incuvate, LLC, Irvine, CA (US)

( * ) Notice: Subject to any disclaimer, the term of this patent is extended or adjusted under 35 U.S.C. 154(b) by 733 days.

(21) Appl. No.: 16/504,768

(22) Filed: Jul. 8, 2019

(65) Prior Publication Data
US 2019/0328410 A1 Oct. 31, 2019

Related U.S. Application Data

(63) Continuation of application No. 15/288,527, filed on Oct. 7, 2016, now abandoned.
(Continued)

(51) Int. Cl.
*A61B 17/22* (2006.01)
*A61B 17/3203* (2006.01)
*A61M 1/00* (2006.01)

(52) U.S. Cl.
CPC ........ *A61B 17/22* (2013.01); *A61B 17/32037* (2013.01); *A61B 2017/22054* (2013.01);
(Continued)

(58) Field of Classification Search
CPC .......... A61B 17/22; A61B 2017/22079; A61B 2017/22054; A61B 2017/22067; A61B 2017/22084; A61M 1/008; A61M 1/84
See application file for complete search history.

(56) References Cited

U.S. PATENT DOCUMENTS

| 1,114,268 A | 10/1914 | Kells |
|---|---|---|
| 1,148,093 A | 7/1915 | Kells |

(Continued)

FOREIGN PATENT DOCUMENTS

| DE | 3715418 A1 | 11/1987 |
|---|---|---|
| EP | 806213 A1 | 11/1997 |

(Continued)

OTHER PUBLICATIONS

Meritrans, Merit Medical Systems, Inc., 400545002/B ID 120606, Date unknown (2 pages).
(Continued)

*Primary Examiner* — Diane D Yabut
*Assistant Examiner* — Christina C Lauer
(74) *Attorney, Agent, or Firm* — Blair Walker IP Services, LLC

(57) ABSTRACT

An aspiration system includes an aspiration catheter including a tubular aspiration member having a proximal end, a distal end, and a lumen, and configured to at least partially extend out of the lumen of an elongate tubular member and into the vasculature of a subject, an elongate support member coupled to the tubular aspiration member and extending between the proximal end of the aspiration catheter and the proximal end of the tubular aspiration member, a high pressure injection lumen extending within the elongate support member and having a distal end including a curved portion configured to change a direction of fluid flow by at least about 90°, at least one orifice located at the distal end of the high pressure injection lumen configured to allow liquid to be released into the lumen of the tubular aspiration member, and an annular seal carried by the tubular aspiration member and configured to create a liquid seal against the inner surface of the elongate tubular member.

20 Claims, 45 Drawing Sheets

Related U.S. Application Data

(60) Provisional application No. 62/239,946, filed on Oct. 11, 2015, provisional application No. 62/239,795, filed on Oct. 9, 2015.

(52) U.S. Cl.
CPC .............. *A61B 2017/22067* (2013.01); *A61B 2017/22079* (2013.01); *A61B 2017/22084* (2013.01); *A61M 1/84* (2021.05); *A61M 2210/12* (2013.01)

(56) References Cited

U.S. PATENT DOCUMENTS

| | | |
|---|---|---|
| 2,804,075 A | 8/1957 | Borden |
| 3,322,433 A | 5/1967 | Rentschler |
| 3,429,313 A | 2/1969 | Romanelli |
| 3,693,613 A | 9/1972 | Kelman |
| 3,707,967 A | 1/1973 | Kitrilakis et al. |
| 3,916,892 A | 11/1975 | Latham, Jr. |
| 3,930,505 A | 1/1976 | Wallach |
| 3,955,573 A | 5/1976 | Hansen et al. |
| 4,299,221 A | 11/1981 | Phillips et al. |
| 4,465,470 A | 8/1984 | Keiman |
| 4,574,812 A | 3/1986 | Arkans |
| 4,606,347 A | 8/1986 | Fogarty et al. |
| 4,638,539 A | 1/1987 | Palmer |
| 4,690,672 A | 9/1987 | Veltrup |
| 4,832,685 A | 5/1989 | Haines |
| 4,875,897 A | 10/1989 | Lee |
| 4,898,574 A | 2/1990 | Uchiyama et al. |
| 4,998,919 A | 3/1991 | Schnepp-Pesch |
| 5,057,098 A | 10/1991 | Zelman |
| 5,064,428 A | 11/1991 | Cope et al. |
| 5,073,164 A | 12/1991 | Hollister et al. |
| 5,073,168 A | 12/1991 | Danforth |
| 5,078,681 A | 1/1992 | Kawashima |
| 5,125,893 A | 6/1992 | Dryden |
| 5,135,482 A | 8/1992 | Neracher |
| 5,141,518 A | 8/1992 | Hess et al. |
| 5,197,951 A | 3/1993 | Mahurkar |
| 5,234,407 A | 8/1993 | Teirstein et al. |
| 5,248,297 A | 9/1993 | Takase |
| 5,259,839 A | 11/1993 | Burns |
| 5,273,047 A | 12/1993 | Tripp et al. |
| 5,273,052 A | 12/1993 | Kraus et al. |
| 5,281,203 A | 1/1994 | Ressemann |
| 5,290,247 A | 3/1994 | Crittenden |
| 5,318,518 A | 6/1994 | Plechinger et al. |
| 5,320,604 A | 6/1994 | Walker et al. |
| 5,322,504 A | 6/1994 | Doherty et al. |
| 5,324,263 A | 6/1994 | Kraus et al. |
| 5,342,293 A | 8/1994 | Zanger |
| 5,342,306 A | 8/1994 | Don Michael |
| 5,368,555 A | 11/1994 | Sussman et al. |
| 5,378,238 A | 1/1995 | Peters et al. |
| 5,380,282 A | 1/1995 | Burns |
| 5,383,890 A | 1/1995 | Miraki et al. |
| 5,385,562 A | 1/1995 | Adams et al. |
| 5,395,315 A | 3/1995 | Griep |
| 5,403,274 A | 4/1995 | Cannon |
| 5,413,561 A | 5/1995 | Fischell et al. |
| 5,419,772 A | 5/1995 | Teitz et al. |
| 5,421,826 A | 6/1995 | Crocker et al. |
| 5,423,742 A | 6/1995 | Theron |
| 5,454,788 A | 10/1995 | Walker et al. |
| 5,468,225 A | 11/1995 | Teirstein |
| 5,484,412 A | 1/1996 | Pierpont |
| 5,486,183 A | 1/1996 | Middleman et al. |
| 5,490,837 A | 2/1996 | Blaeser et al. |
| 5,496,267 A | 3/1996 | Drasler et al. |
| 5,522,818 A | 6/1996 | Keith et al. |
| 5,527,274 A | 6/1996 | Zakko |
| 5,533,968 A | 7/1996 | Muni et al. |
| 5,536,242 A | 7/1996 | Willard et al. |
| 5,538,002 A | 7/1996 | Boussignac et al. |
| 5,567,203 A | 10/1996 | Euteneuer et al. |
| 5,581,038 A | 12/1996 | Lampropoulos et al. |
| 5,606,968 A | 3/1997 | Mang |
| 5,624,394 A | 4/1997 | Barnitz et al. |
| 5,647,847 A | 7/1997 | Lafontaine et al. |
| 5,658,251 A | 8/1997 | Ressemann et al. |
| 5,676,654 A | 10/1997 | Ellis et al. |
| 5,702,413 A | 12/1997 | LaFontaine |
| 5,713,849 A | 2/1998 | Bosma et al. |
| 5,713,851 A | 2/1998 | Boudewijn et al. |
| 5,713,878 A | 2/1998 | Moutafis et al. |
| 5,720,724 A | 2/1998 | Ressemann et al. |
| 5,730,717 A | 3/1998 | Gelbfish |
| 5,749,852 A | 5/1998 | Schwab et al. |
| 5,762,631 A | 6/1998 | Klein |
| 5,772,674 A | 6/1998 | Nakhjavan |
| 5,785,685 A | 7/1998 | Kugler et al. |
| 5,795,322 A | 8/1998 | Boudewijn |
| 5,827,229 A | 10/1998 | Auth et al. |
| 5,827,243 A | 10/1998 | Palestrant |
| 5,833,706 A | 11/1998 | St. Germain et al. |
| 5,843,022 A | 12/1998 | Willard et al. |
| 5,843,051 A | 12/1998 | Adams et al. |
| 5,855,567 A | 1/1999 | Ressemann |
| 5,863,284 A | 1/1999 | Klein |
| 5,868,702 A | 2/1999 | Stevens et al. |
| 5,871,462 A | 2/1999 | Yoder et al. |
| 5,885,238 A | 3/1999 | Stevens et al. |
| 5,885,244 A | 3/1999 | Leone et al. |
| 5,895,399 A | 4/1999 | Barbut et al. |
| 5,910,252 A | 6/1999 | Truitt et al. |
| 5,916,192 A | 6/1999 | Nita et al. |
| 5,921,958 A | 7/1999 | Ressemann et al. |
| 5,938,645 A | 8/1999 | Gordon |
| 5,941,871 A | 8/1999 | Adams et al. |
| 5,944,686 A | 8/1999 | Patterson et al. |
| 5,957,901 A | 9/1999 | Mottola et al. |
| 5,976,107 A | 11/1999 | Mertens et al. |
| 5,989,210 A | 11/1999 | Morris et al. |
| 6,001,112 A | 12/1999 | Taylor |
| 6,019,728 A | 2/2000 | Iwata et al. |
| 6,022,336 A | 2/2000 | Zadno-Azizi et al. |
| 6,096,001 A | 8/2000 | Drasler et al. |
| 6,096,009 A | 8/2000 | Windheuser et al. |
| 6,126,635 A | 10/2000 | Simpson et al. |
| 6,129,697 A | 10/2000 | Drasler et al. |
| 6,129,698 A | 10/2000 | Beck |
| 6,146,396 A | 11/2000 | Kónya et al. |
| 6,159,230 A | 12/2000 | Samuels |
| 6,176,844 B1 | 1/2001 | Lee |
| 6,179,851 B1 | 1/2001 | Barbut et al. |
| 6,190,357 B1 | 2/2001 | Ferrari et al. |
| 6,196,989 B1 | 3/2001 | Padget et al. |
| 6,216,573 B1 | 4/2001 | Moutafis et al. |
| 6,224,570 B1 | 5/2001 | Le et al. |
| 6,241,703 B1 | 6/2001 | Levin et al. |
| 6,258,061 B1 | 7/2001 | Drasler et al. |
| 6,283,719 B1 | 9/2001 | Frantz et al. |
| 6,293,960 B1 | 9/2001 | Ken |
| 6,375,635 B1 | 4/2002 | Moutafis et al. |
| 6,471,683 B2 | 10/2002 | Drasler et al. |
| 6,481,439 B1 | 11/2002 | Lewis et al. |
| 6,488,672 B1 | 12/2002 | Dance et al. |
| 6,497,698 B1 | 12/2002 | Fonger et al. |
| 6,544,209 B1 | 4/2003 | Drasler et al. |
| 6,558,401 B1 | 5/2003 | Azizi |
| 6,569,148 B2 | 5/2003 | Bagaoisan et al. |
| 6,572,578 B1 | 6/2003 | Blanchard |
| 6,579,270 B2 | 6/2003 | Sussman et al. |
| 6,585,705 B1 | 7/2003 | Maginot et al. |
| 6,599,271 B1 | 7/2003 | Easley |
| 6,610,046 B1 | 8/2003 | Usami et al. |
| 6,616,679 B1 | 9/2003 | Khosravi et al. |
| 6,622,367 B1 | 9/2003 | Bolduc et al. |
| 6,635,070 B2 | 10/2003 | Leeflang et al. |
| 6,669,710 B2 | 12/2003 | Moutafis et al. |
| 6,676,637 B1 | 1/2004 | Bonnette et al. |
| 6,706,018 B2 | 3/2004 | Westlund et al. |

(56) References Cited

U.S. PATENT DOCUMENTS

| | | |
|---|---|---|
| 6,719,717 B1 | 4/2004 | Johnson et al. |
| 6,723,081 B1 | 4/2004 | Hektner |
| 6,755,803 B1 | 6/2004 | Le et al. |
| 6,755,812 B2 | 6/2004 | Peterson et al. |
| 6,818,001 B2 | 11/2004 | Wulfman et al. |
| 6,899,712 B2 | 5/2005 | Moutafis et al. |
| 6,926,726 B2 | 8/2005 | Drasler et al. |
| 6,958,059 B2 | 10/2005 | Zadno-Azizi |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,232,452 B2 | 6/2007 | Adams et al. |
| 7,241,273 B2 | 7/2007 | Maguire et al. |
| 7,244,243 B2 | 7/2007 | Lary |
| 7,267,660 B2 | 9/2007 | Fonger et al. |
| 7,294,124 B2 | 11/2007 | Eidenschink |
| 7,344,515 B2 | 3/2008 | Coyle |
| 7,374,560 B2 | 5/2008 | Ressemann et al. |
| 7,479,147 B2 | 1/2009 | Honeycutt et al. |
| 7,481,222 B2 | 1/2009 | Reissmann |
| 7,503,904 B2 | 3/2009 | Choi |
| 7,588,033 B2 | 9/2009 | Wondka |
| 7,591,816 B2 | 9/2009 | Wang et al. |
| 7,604,612 B2 | 10/2009 | Ressemann et al. |
| 7,621,886 B2 | 11/2009 | Burnett |
| 7,666,161 B2 | 2/2010 | Nash et al. |
| 7,678,081 B2 | 3/2010 | Whiting et al. |
| 7,699,804 B2 | 4/2010 | Barry et al. |
| 7,717,685 B2 | 5/2010 | Moutafis et al. |
| 7,717,898 B2 | 5/2010 | Gately et al. |
| 7,736,355 B2 | 6/2010 | Itou et al. |
| 7,753,868 B2 | 7/2010 | Hoffa |
| 7,753,880 B2 | 7/2010 | Malackowski |
| 7,763,012 B2 | 7/2010 | Petrick et al. |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,846,175 B2 | 12/2010 | Bonnette et al. |
| 7,867,192 B2 | 1/2011 | Bowman et al. |
| 7,875,004 B2 | 1/2011 | Yodfat et al. |
| 7,879,022 B2 | 2/2011 | Bonnette et al. |
| 7,887,510 B2 | 2/2011 | Karpowicz et al. |
| 7,905,710 B2 | 3/2011 | Wang et al. |
| 7,909,810 B2 | 3/2011 | Noone |
| 7,914,482 B2 | 3/2011 | Urich et al. |
| 7,914,549 B2 | 3/2011 | Morsi |
| 7,918,654 B2 | 4/2011 | Adahan |
| 7,918,822 B2 | 4/2011 | Kumar et al. |
| 7,918,835 B2 | 4/2011 | Callahan et al. |
| 7,935,077 B2 | 5/2011 | Thor et al. |
| 7,951,073 B2 | 5/2011 | Freed |
| 7,951,107 B2 | 5/2011 | Staid et al. |
| 7,951,112 B2 | 5/2011 | Patzer |
| 7,959,603 B2 | 6/2011 | Wahr et al. |
| 7,981,129 B2 | 7/2011 | Nash et al. |
| 7,988,705 B2 | 8/2011 | Galdonik et al. |
| 7,998,114 B2 | 8/2011 | Lombardi |
| 8,007,490 B2 | 8/2011 | Schaeffer et al. |
| 3,021,351 A1 | 9/2011 | Boldenow et al. |
| 8,012,766 B2 | 9/2011 | Graham |
| 3,043,313 A1 | 10/2011 | Krolik et al. |
| 8,034,018 B2 | 10/2011 | Lutwyche |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 3,070,694 A1 | 12/2011 | Galdonik et al. |
| 8,075,546 B2 | 12/2011 | Carlisle et al. |
| 8,092,483 B2 | 1/2012 | Galdonik et al. |
| 8,114,057 B2 | 2/2012 | Gerdts et al. |
| 8,123,778 B2 | 2/2012 | Brady et al. |
| 8,140,146 B2 | 3/2012 | Kim et al. |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,202,243 B2 | 6/2012 | Morgan |
| 8,209,060 B2 | 6/2012 | Ledford |
| 8,221,348 B2 | 7/2012 | Hackett et al. |
| 8,246,573 B2 | 8/2012 | Ali et al. |
| 8,246,574 B2 | 8/2012 | Jacobs et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,313,478 B2 | 11/2012 | Tockman et al. |
| 8,317,739 B2 | 11/2012 | Kuebler |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,268 B2 | 12/2012 | Ring et al. |
| 8,337,175 B2 | 12/2012 | Dion et al. |
| 8,343,131 B2 | 1/2013 | Vinten-Johansen |
| 8,348,896 B2 | 1/2013 | Wagner |
| 8,353,858 B2 | 1/2013 | Kozak et al. |
| 8,353,860 B2 | 1/2013 | Boulais et al. |
| 8,357,138 B2 | 1/2013 | Pierpont et al. |
| 8,372,038 B2 | 2/2013 | Urich et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,444,625 B2 | 5/2013 | Stalker et al. |
| 8,454,557 B1 | 6/2013 | Qi et al. |
| 8,465,456 B2 | 6/2013 | Stivland |
| 8,465,867 B2 | 6/2013 | Kim |
| 8,480,697 B2 | 7/2013 | Kucharczyk et al. |
| 8,483,980 B2 | 7/2013 | Moberg et al. |
| 8,491,523 B2 | 7/2013 | Thor et al. |
| 8,506,537 B2 | 8/2013 | Torstensen et al. |
| 8,523,801 B2 | 9/2013 | Nash et al. |
| 8,535,272 B2 | 9/2013 | Wang et al. |
| 8,545,514 B2 | 10/2013 | Ferrera |
| 8,562,555 B2 | 10/2013 | MacMahon et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier, Jr. et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,657,845 B2 | 2/2014 | Lentz |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,721,674 B2 | 5/2014 | Kusleika |
| 8,734,399 B2 | 5/2014 | Nelson |
| 8,740,874 B2 | 6/2014 | Ravenscroft |
| 8,758,325 B2 | 6/2014 | Webster et al. |
| 8,771,305 B2 | 7/2014 | Shriver |
| 8,783,151 B1 | 7/2014 | Janardhan et al. |

(56) References Cited

U.S. PATENT DOCUMENTS

| | | | |
|---|---|---|---|
| 8,803,030 | B1 | 8/2014 | Janardhan et al. |
| 8,808,270 | B2 | 8/2014 | Dann et al. |
| 8,814,847 | B2 | 8/2014 | Hoffman et al. |
| 8,814,892 | B2 | 8/2014 | Galdonik et al. |
| 8,851,866 | B2 | 10/2014 | Moutafis et al. |
| 8,852,219 | B2 | 10/2014 | Wulfman et al. |
| RE45,760 | E | 10/2015 | Root et al. |
| RE45,776 | E | 10/2015 | Root et al. |
| 2001/0051811 | A1 | 12/2001 | Bonnette et al. |
| 2002/0068895 | A1 | 6/2002 | Beck |
| 2002/0133114 | A1 | 9/2002 | Itoh et al. |
| 2002/0138095 | A1 | 9/2002 | Mazzocchi et al. |
| 2002/0165575 | A1 | 11/2002 | Saleh |
| 2002/0173819 | A1 | 11/2002 | Leeflang et al. |
| 2002/0176788 | A1 | 11/2002 | Moutafis et al. |
| 2003/0032918 | A1 | 2/2003 | Quinn |
| 2003/0069549 | A1 | 4/2003 | MacMahon et al. |
| 2003/0088209 | A1 | 5/2003 | Chiu et al. |
| 2003/0144688 | A1 | 7/2003 | Brady et al. |
| 2003/0216760 | A1 | 11/2003 | Welch et al. |
| 2003/0220556 | A1 | 11/2003 | Porat et al. |
| 2003/0236533 | A1 | 12/2003 | Wilson et al. |
| 2004/0049225 | A1 | 3/2004 | Denison |
| 2004/0087988 | A1 | 5/2004 | Heitzmann et al. |
| 2004/0147871 | A1 | 7/2004 | Burnett |
| 2004/0158136 | A1 | 8/2004 | Gough et al. |
| 2004/0167463 | A1 | 8/2004 | Zawacki |
| 2004/0193046 | A1 | 9/2004 | Nash et al. |
| 2004/0199201 | A1 | 10/2004 | Kellet et al. |
| 2004/0243157 | A1 | 12/2004 | Connor et al. |
| 2005/0065426 | A1 | 3/2005 | Porat et al. |
| 2005/0102165 | A1 | 5/2005 | Oshita et al. |
| 2005/0159716 | A1 | 7/2005 | Kobayashi et al. |
| 2005/0196748 | A1 | 9/2005 | Ericson |
| 2005/0240146 | A1 | 10/2005 | Nash et al. |
| 2005/0283150 | A1 | 12/2005 | Moutafis et al. |
| 2006/0009785 | A1 | 1/2006 | Maitland et al. |
| 2006/0058836 | A1 | 3/2006 | Bose et al. |
| 2006/0063973 | A1 | 3/2006 | Makower et al. |
| 2006/0064123 | A1 | 3/2006 | Bonnette et al. |
| 2006/0142630 | A1 | 6/2006 | Meretei |
| 2007/0073233 | A1 | 3/2007 | Thor et al. |
| 2007/0073268 | A1 | 3/2007 | Goble et al. |
| 2007/0078438 | A1 | 4/2007 | Okada |
| 2007/0197956 | A1 | 8/2007 | Le et al. |
| 2007/0225739 | A1 | 9/2007 | Pintor et al. |
| 2008/0009784 | A1 | 1/2008 | Leedle et al. |
| 2008/0079221 | A1* | 4/2008 | Tupper .................. F16J 15/164 277/345 |
| 2008/0086110 | A1 | 4/2008 | Galdonik et al. |
| 2008/0097339 | A1 | 4/2008 | Ranchod et al. |
| 2008/0097563 | A1 | 4/2008 | Petrie et al. |
| 2008/0195139 | A1 | 8/2008 | Donald et al. |
| 2008/0249501 | A1 | 10/2008 | Yamasaki |
| 2008/0255596 | A1 | 10/2008 | Jenson et al. |
| 2008/0294181 | A1 | 11/2008 | Wensel et al. |
| 2008/0306465 | A1 | 12/2008 | Bailey et al. |
| 2008/0319376 | A1 | 12/2008 | Wilcox et al. |
| 2009/0054825 | A1 | 2/2009 | Melsheimer et al. |
| 2009/0105690 | A1 | 4/2009 | Schaeffer et al. |
| 2009/0157057 | A1 | 6/2009 | Ferren et al. |
| 2009/0292212 | A1 | 11/2009 | Ferren et al. |
| 2010/0010524 | A1 | 1/2010 | Barrington et al. |
| 2010/0030186 | A1 | 2/2010 | Stivland |
| 2010/0094201 | A1 | 4/2010 | Mallaby |
| 2010/0204672 | A1 | 8/2010 | Lockhart et al. |
| 2010/0217276 | A1 | 8/2010 | Garrison et al. |
| 2010/0274191 | A1 | 10/2010 | Ting |
| 2011/0091331 | A1 | 4/2011 | Moutafis et al. |
| 2011/0106019 | A1 | 5/2011 | Bagwell et al. |
| 2011/0160683 | A1 | 6/2011 | Pinotti Barbosa et al. |
| 2012/0059340 | A1 | 3/2012 | Larsson |
| 2012/0071907 | A1 | 3/2012 | Pintor et al. |
| 2012/0123509 | A1 | 5/2012 | Merrill et al. |
| 2012/0130415 | A1 | 5/2012 | Tal et al. |
| 2012/0165756 | A1 | 6/2012 | Root et al. |
| 2012/0259265 | A1 | 10/2012 | Salehi et al. |
| 2012/0289910 | A1 | 11/2012 | Shtul et al. |
| 2012/0291811 | A1 | 11/2012 | Dabney et al. |
| 2013/0085381 | A1 | 4/2013 | Comerota et al. |
| 2013/0116701 | A1 | 5/2013 | Wang et al. |
| 2013/0190701 | A1 | 7/2013 | Kim |
| 2013/0267891 | A1 | 10/2013 | Malhi et al. |
| 2013/0310845 | A1 | 11/2013 | Thor et al. |
| 2014/0005699 | A1 | 1/2014 | Bonnette et al. |
| 2014/0147246 | A1 | 5/2014 | Chappel et al. |
| 2014/0155931 | A1 | 6/2014 | Bose et al. |
| 2014/0276920 | A1 | 9/2014 | Hendrick et al. |
| 2014/0309589 | A1 | 10/2014 | Momose et al. |
| 2014/0323906 | A1 | 10/2014 | Peatfield et al. |
| 2015/0094748 | A1 | 4/2015 | Nash et al. |
| 2015/0282821 | A1* | 10/2015 | Look ..................... A61M 1/90 606/127 |
| 2015/0283309 | A1 | 10/2015 | Look et al. |
| 2015/0327875 | A1 | 11/2015 | Look et al. |
| 2017/0143938 | A1 | 5/2017 | Ogle et al. |

FOREIGN PATENT DOCUMENTS

| | | |
|---|---|---|
| EP | 726466 B1 | 4/2002 |
| EP | 1488748 A1 | 12/2004 |
| WO | WO199005493 A1 | 5/1990 |
| WO | WO1996001079 A1 | 1/1996 |
| WO | WO1996035469 A1 | 11/1996 |
| WO | WO199918850 A1 | 4/1999 |
| WO | WO2001037916 A1 | 5/2001 |
| WO | WO2004100772 A2 | 11/2004 |
| WO | WO2007143633 A2 | 12/2007 |
| WO | WO2008097993 A2 | 8/2008 |
| WO | WO2016/126974 A1 | 8/2016 |

OTHER PUBLICATIONS

Merit Mentor Simulator/Tester Instructions for Use, Merit Medical Systems, Inc., 460101002 ID 062696, Date unknown (12 pages).

"Comparison of Dimensions and Aspiration Rate of the Pronto V3, Pronto LP, Export XT, Export AP, Fetch, Xtract, Diver C.E. and QuickCat Catheter", Vascular Solutions, Inc., downloaded from internet Oct. 22, 2014.

Frölich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.

Gousios, A., Shearn, M, "Effect of Intravenous Heparin on Human Blood Viscosity", Circulation, Dec. 1959, pp. 1063-1066, vol. 20, American Heart Association, Dallas, USA.

"Infusion Liquid Flow Sensors—Safe, Precise and Reliable", Sensirion, downloaded from internet Apr. 3, 2015.

"Makes even the most difficult intervention A Fast and Smooth Run." GuideLiner brochure. Vascular Solutions, Inc., downloaded from internet Apr. 9, 2015.

Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.

Prasad, A., Stone, G., Holmes, D., Gersh, B., "Peperfusion Injury, Microvascular Dysfunction, and Carioprotection: The Dark Side" of Reperfusion, Circulation, Nov. 24, 2009, pp. 2105-2112, vol. 120, American Heart Association, Dallas, USA.

Rodriquez, R., Condé-Green, A., "Quantification of Negative Pressures Generated by Syringes of Different Calibers Used for Liposuction", Plastic & Reconstructive Surgery, Aug. 2012, pp. 383e-384e, vol. 130, No. 2, Lippicott Williams & Wilkins, Philadelphia, USA.

Stys, A., Stys, T., Rajpurohit, N., Khan, M. "A Novel Application of GuideLiner Catheter for Thrombectomy in Acute Myocardial Infarction: A Case Series", Journal of Invasive cardiology, Nov. 2013, pp. 620-624, vol. 25, No. 11, King of Prussia, USA.

(56) References Cited

OTHER PUBLICATIONS

PCT International Search Report and Written Opinion for PCT/US2016/056205, Applicant: Incuvate, LLC, Forms PCT/ISA/220, 210, and 237 dated Mar. 24, 2017 (11 pages).

* cited by examiner

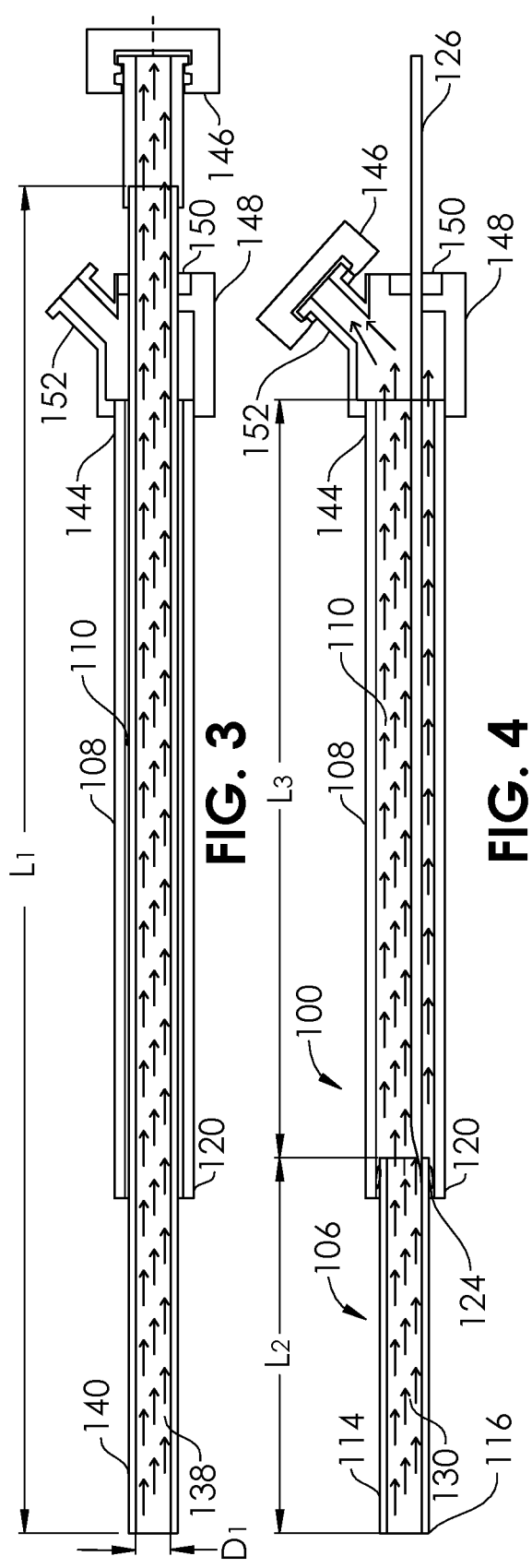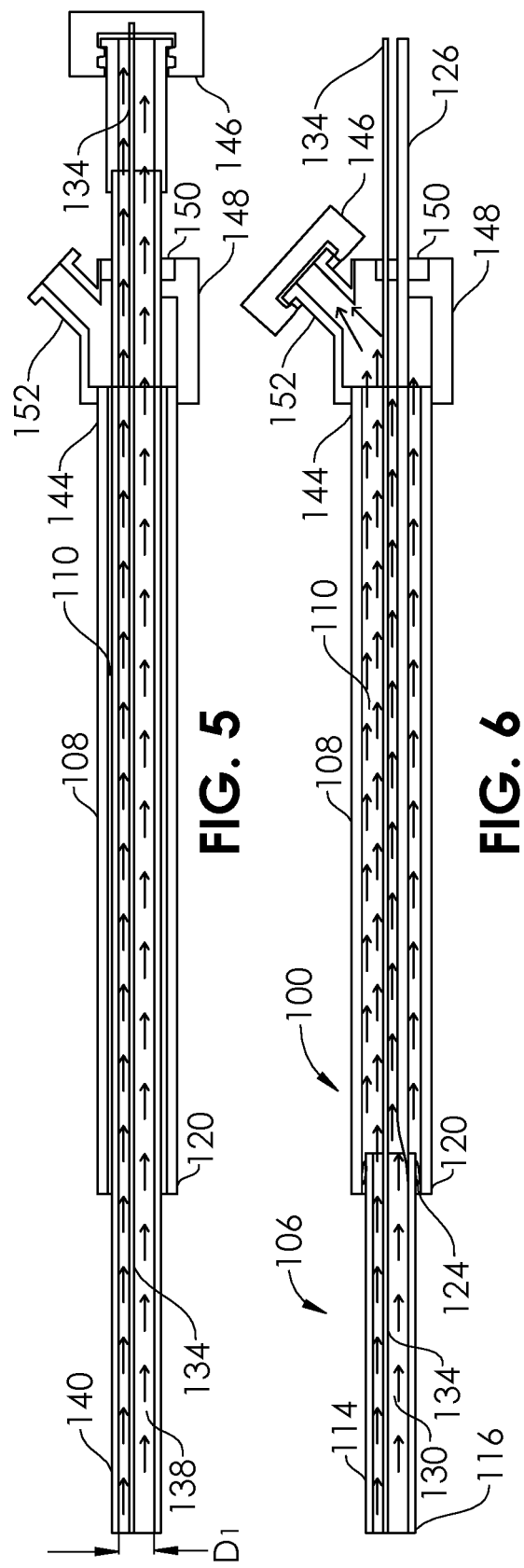

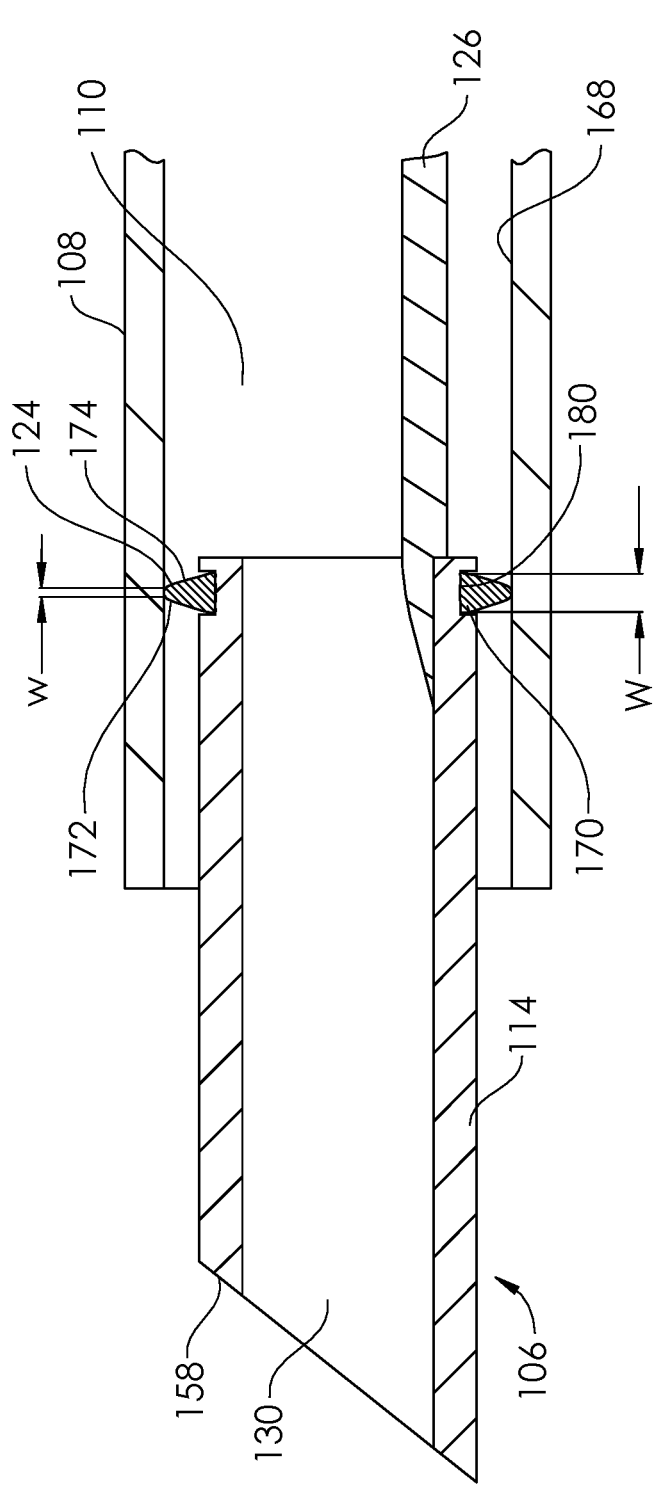
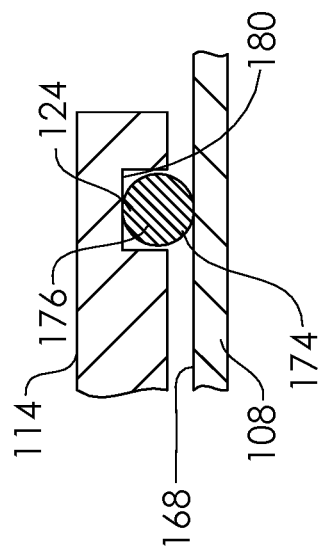
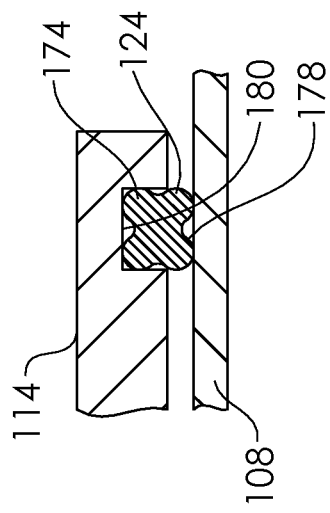
FIG. 15A
FIG. 15B
FIG. 15C

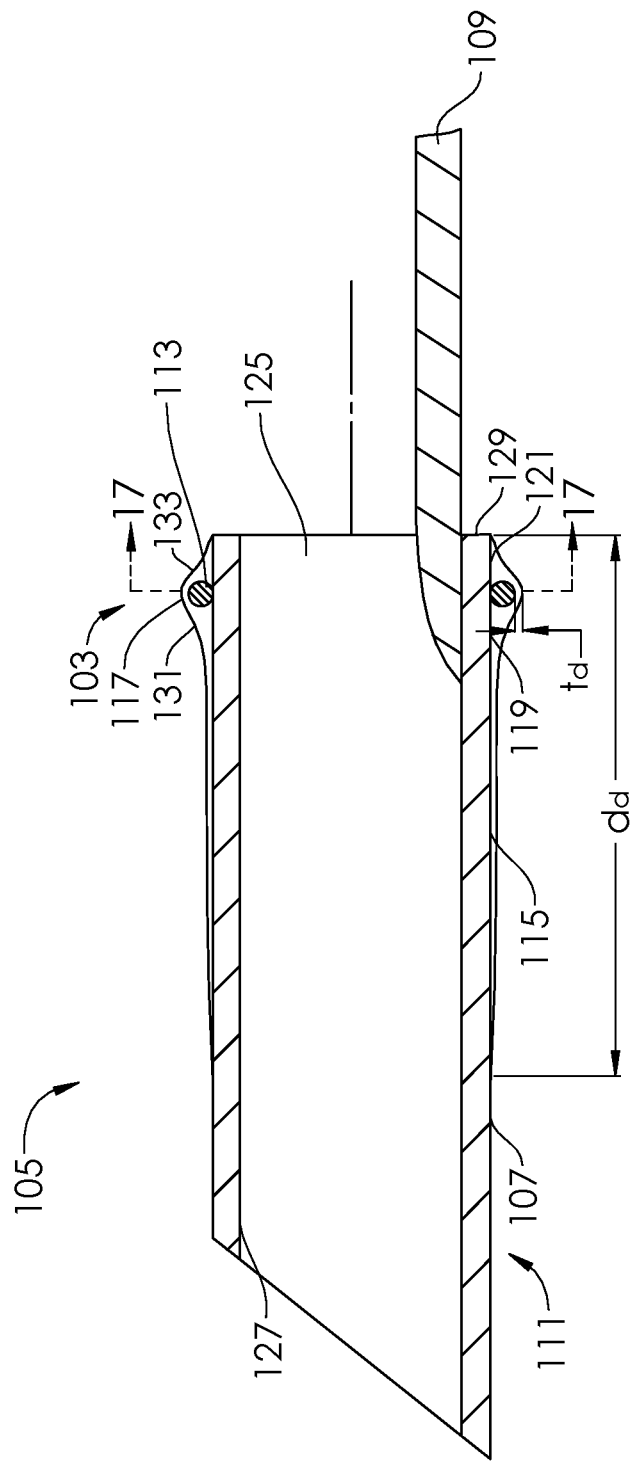
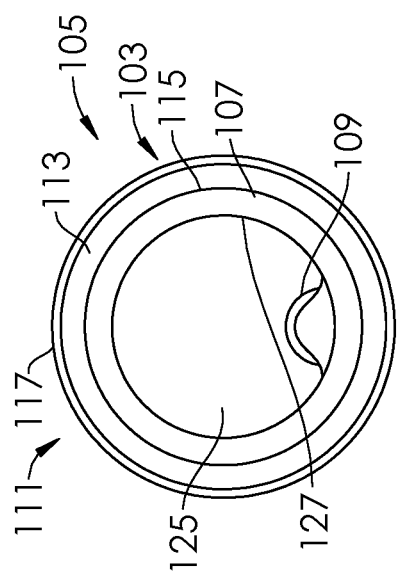

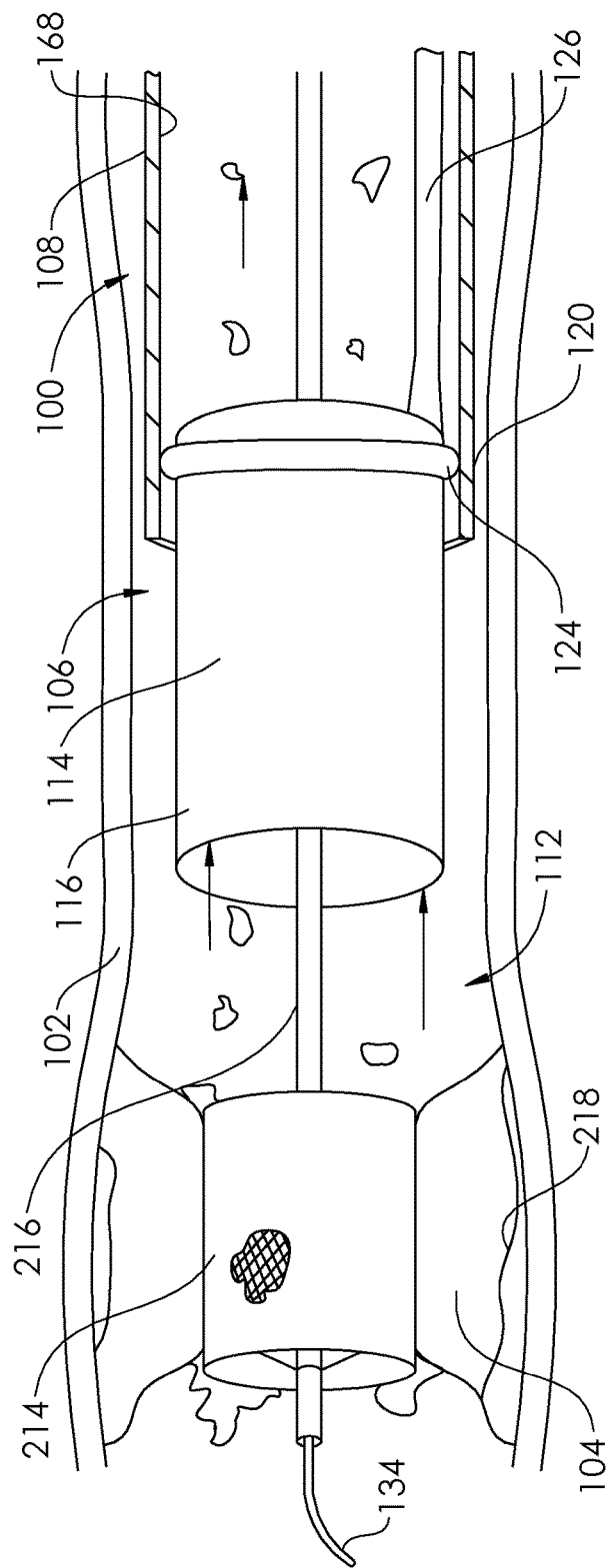
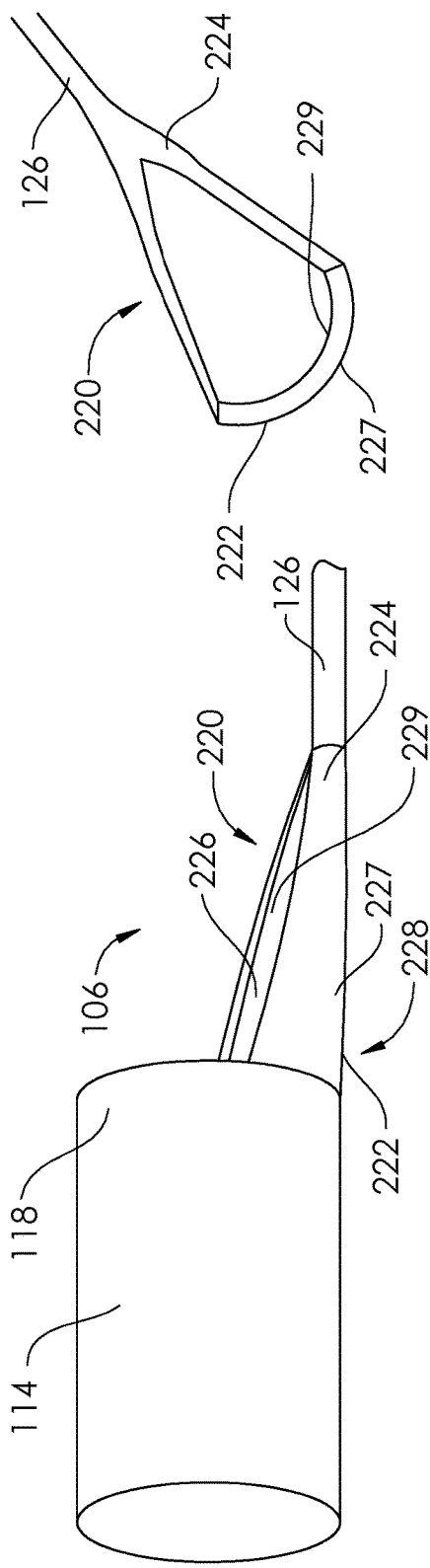
FIG. 25
FIG. 26A
FIG. 26B

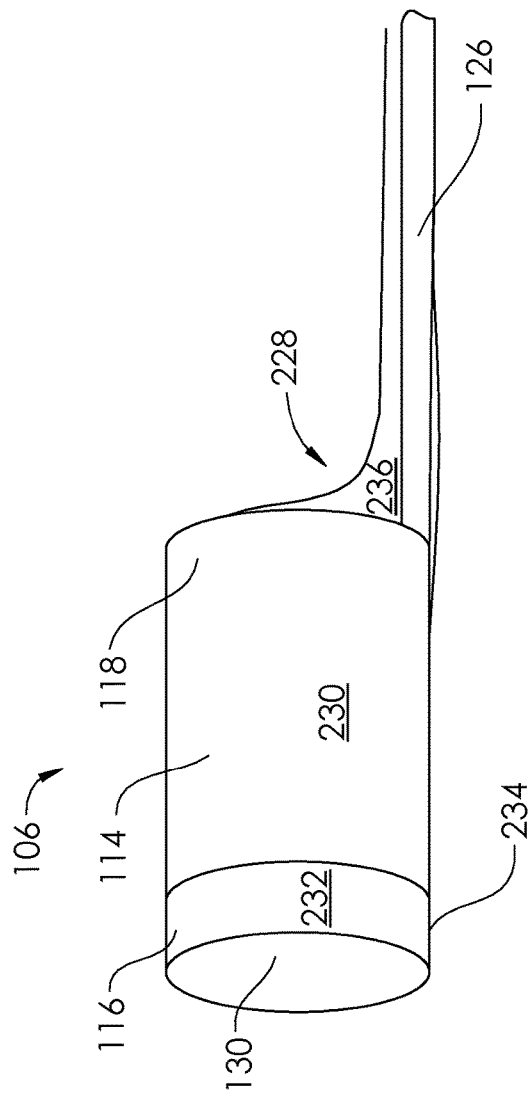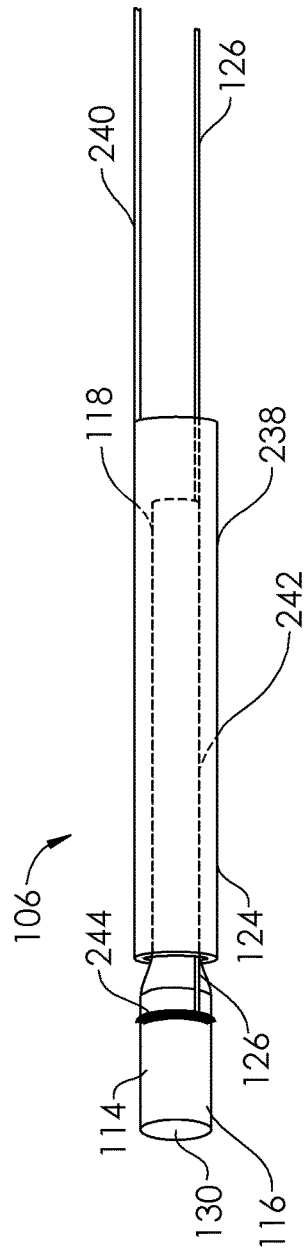

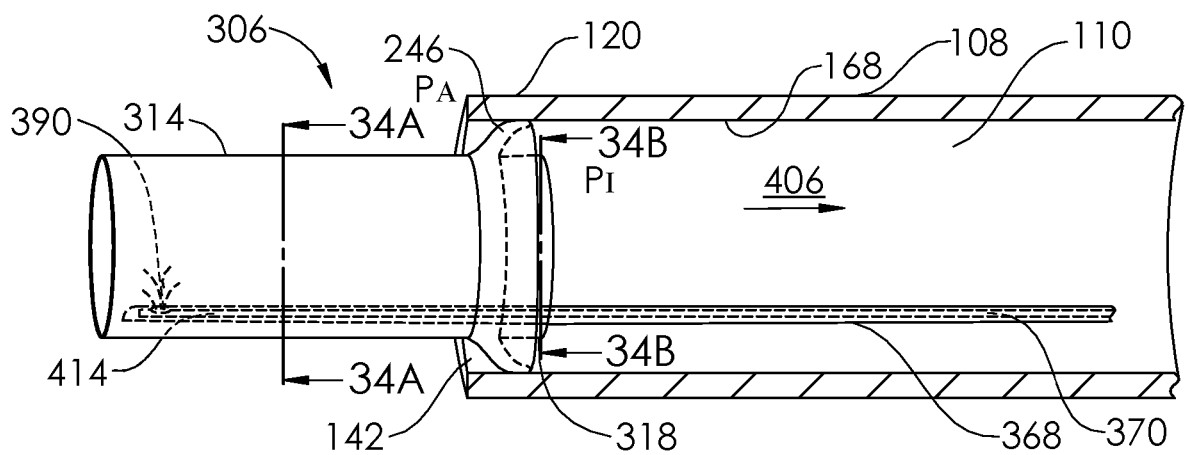
FIG. 33
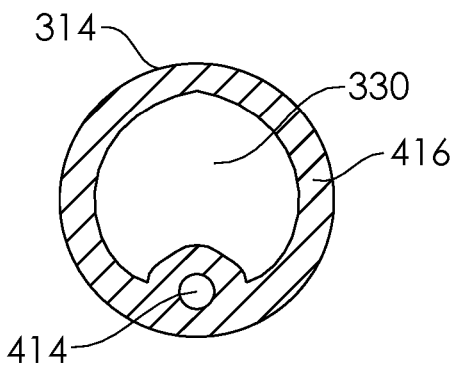      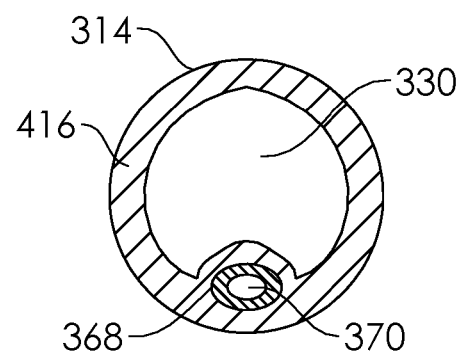
FIG. 34A                FIG. 34B

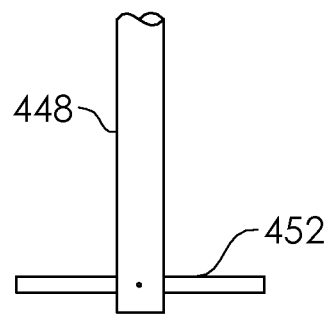
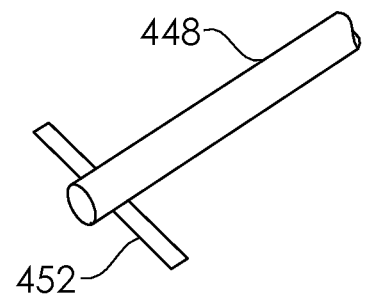
FIG. 39
FIG. 40
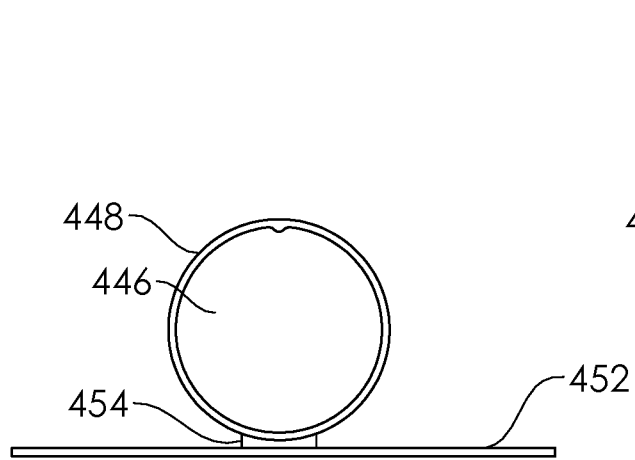
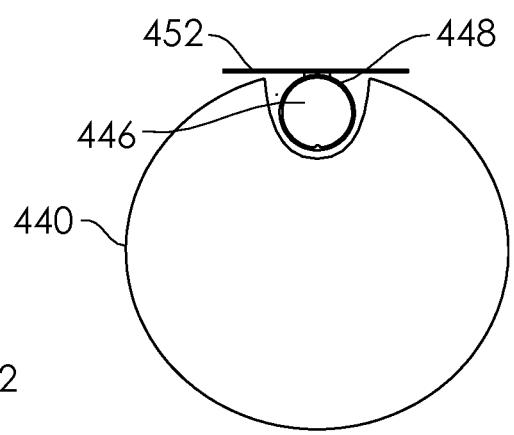
FIG. 41
FIG. 42

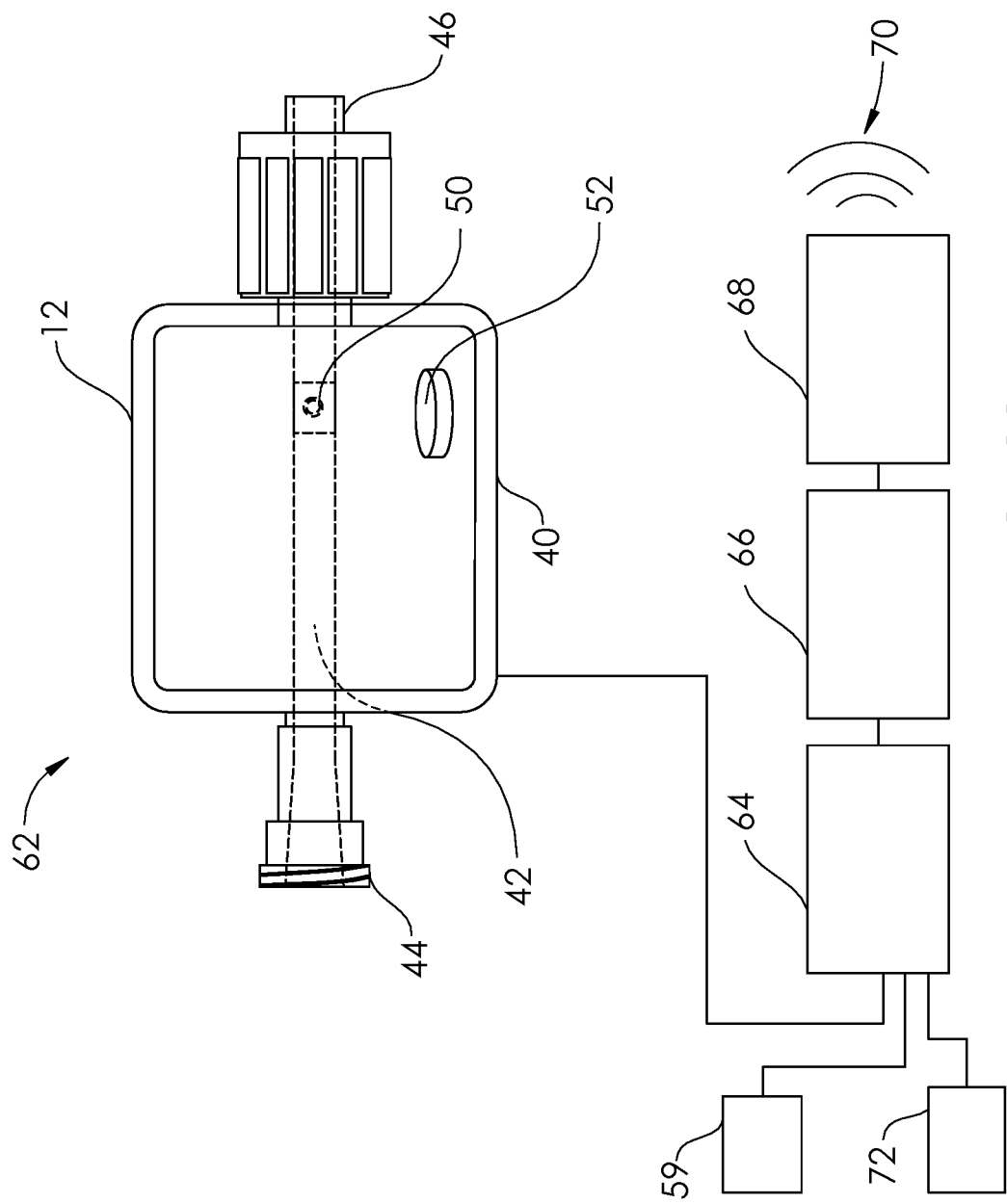

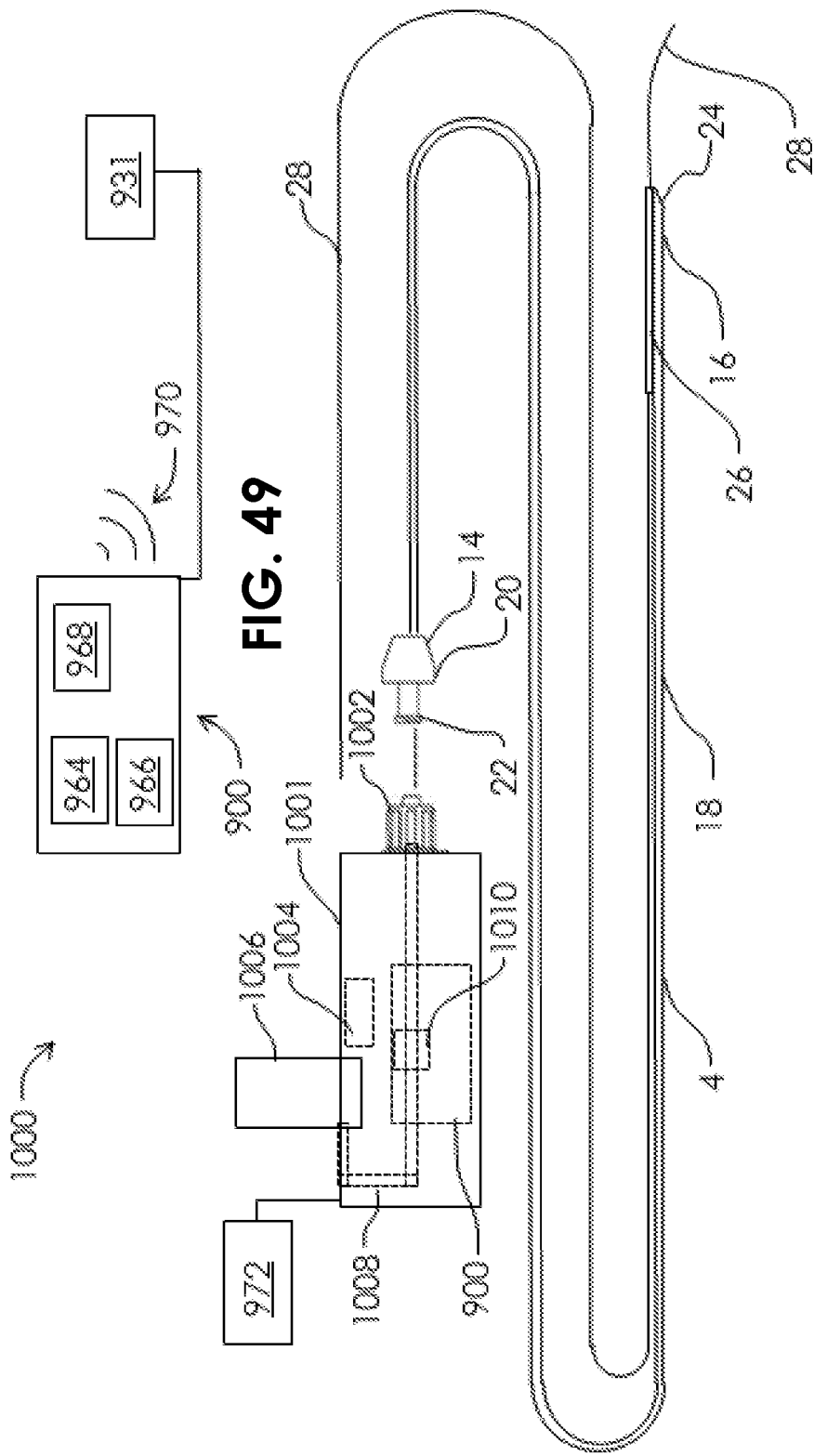

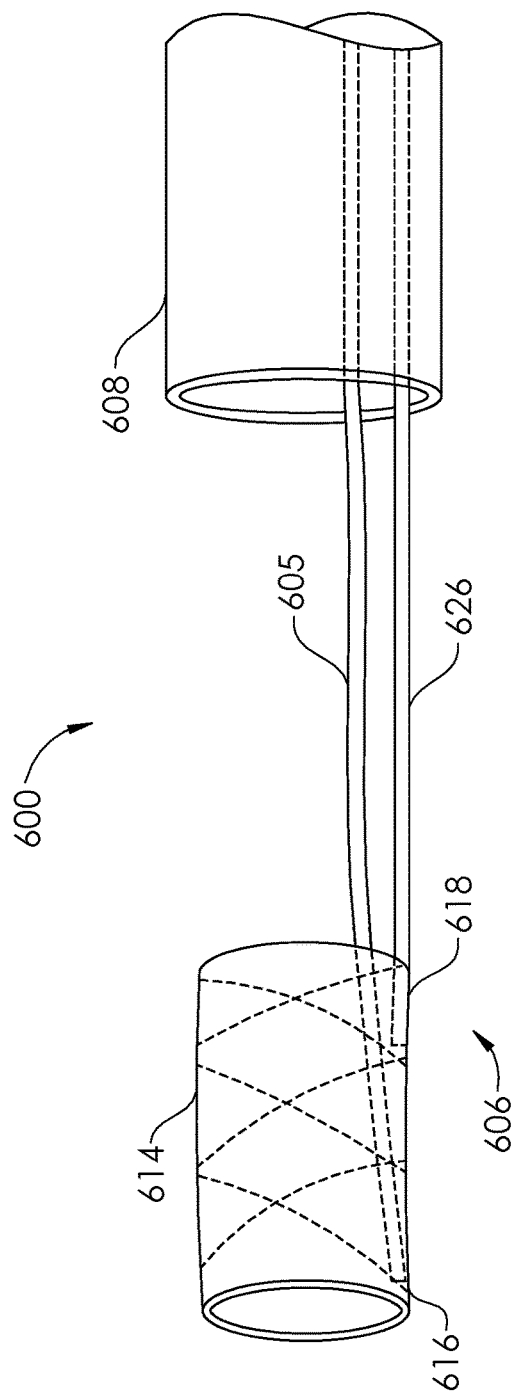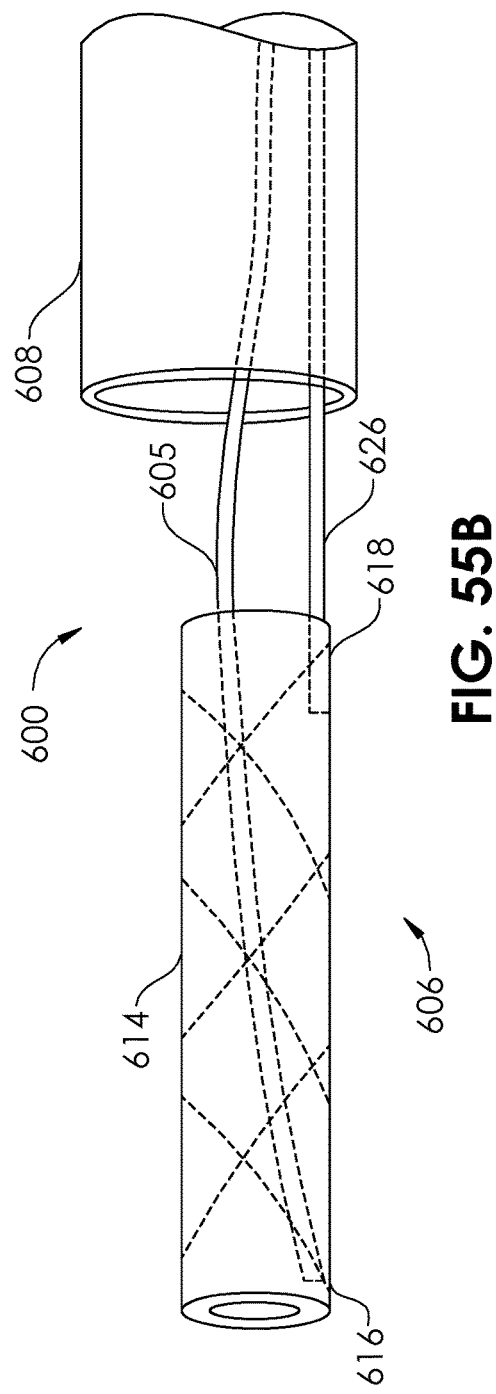

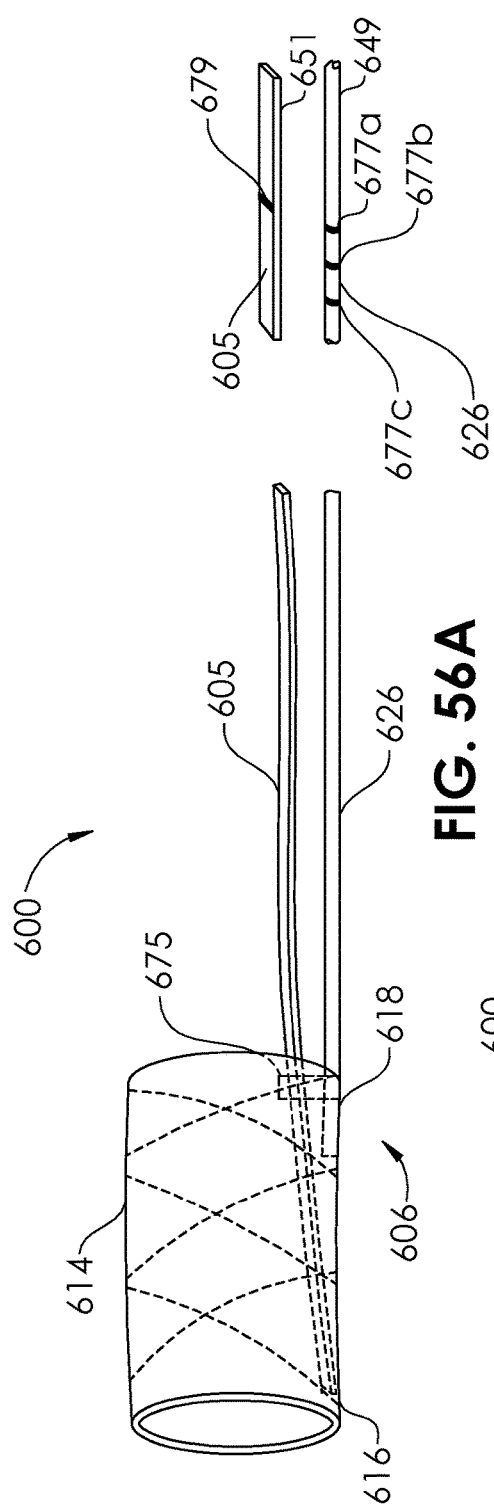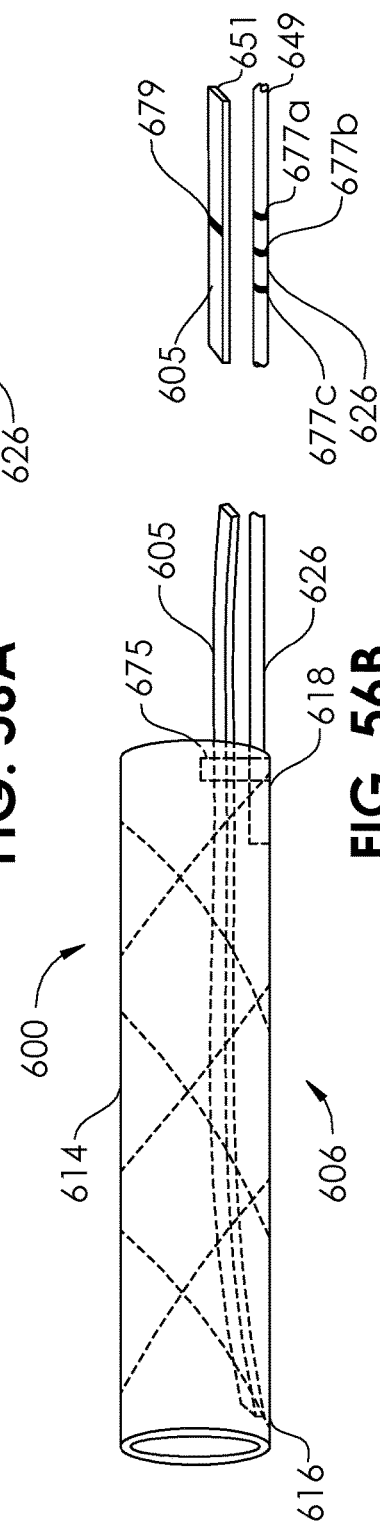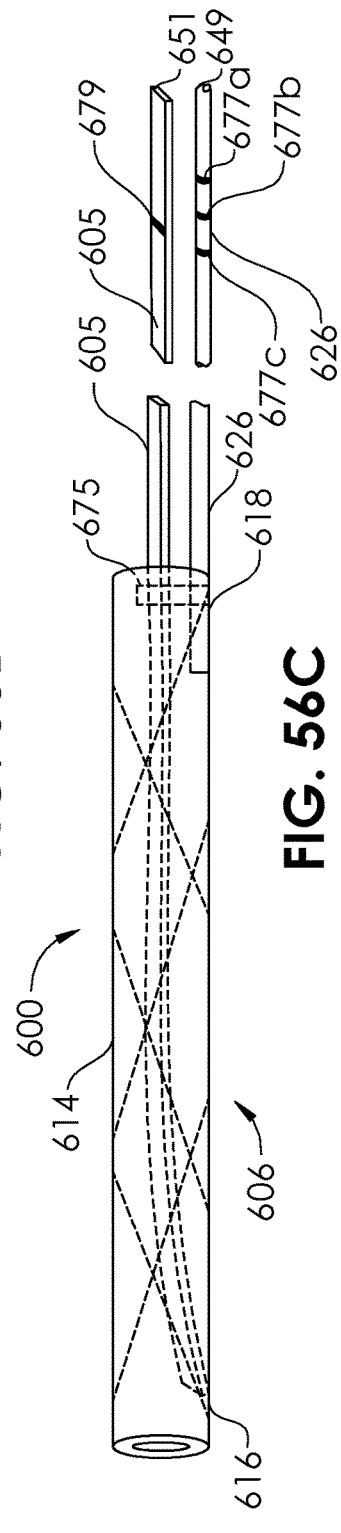

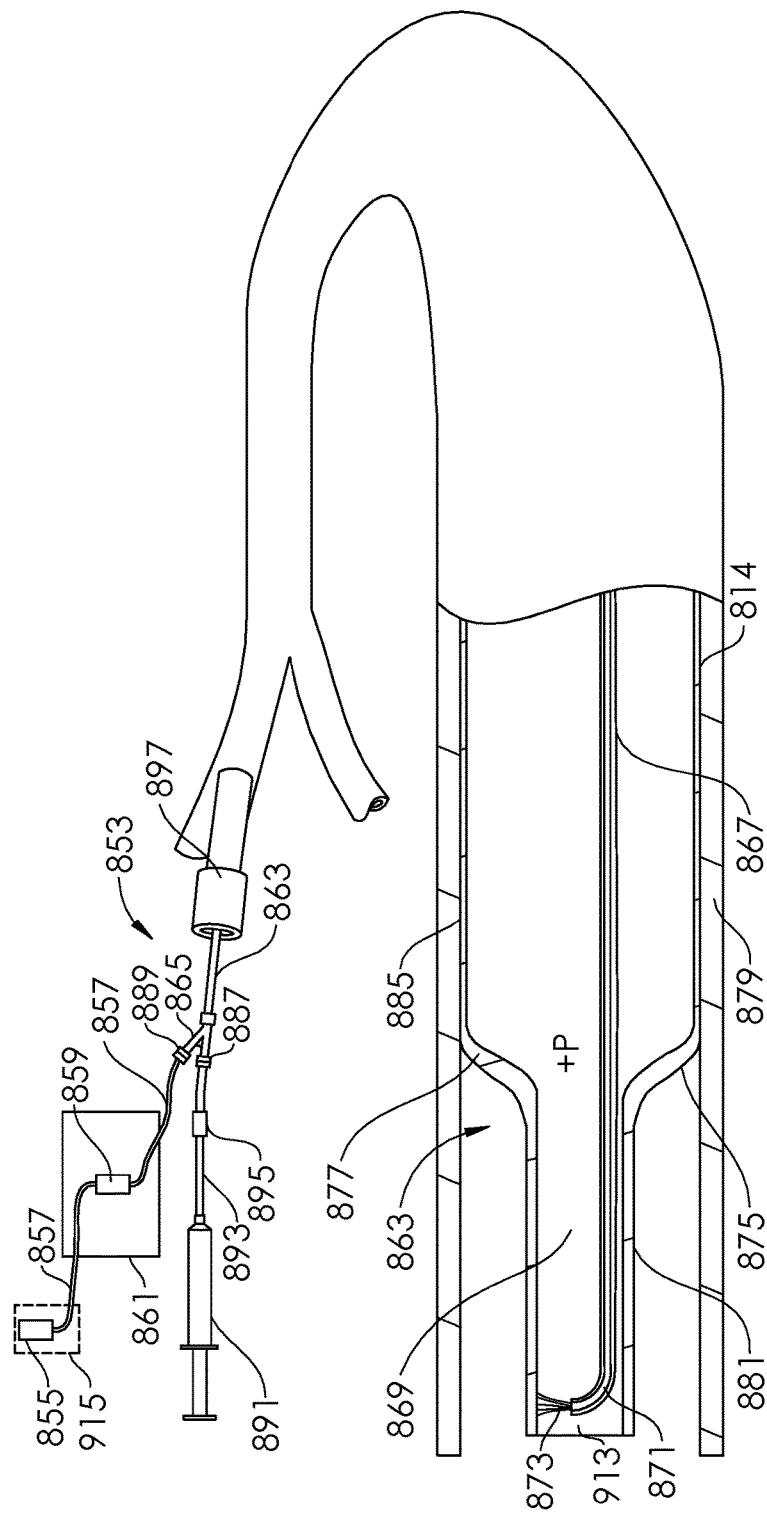
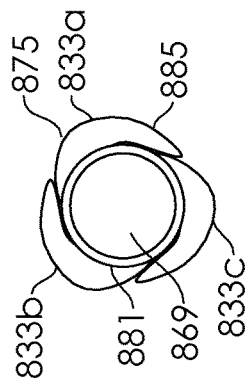
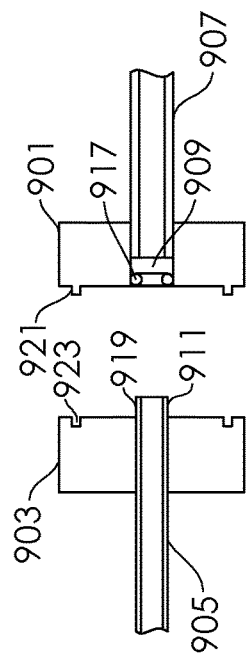
FIG. 69A
FIG. 69B
FIG. 70

SYSTEMS AND METHODS FOR MANAGEMENT OF THROMBOSIS

INCORPORATION BY REFERENCE TO ANY PRIORITY APPLICATIONS

This application is a continuation of U.S. patent application Ser. No. 15/288,527, filed on Oct. 7, 2016, now abandoned, which claims the benefit of priority to U.S. Provisional Patent Application No. 62/239,795, filed on Oct. 9, 2015, and U.S. Provisional Patent Application No. 62/239,946, filed on Oct. 11, 2015, all of which are incorporated herein by reference in their entireties for all purposes. Priority is claimed pursuant to 35 U.S.C. § 120 and 35 U.S.C. § 119.

FIELD OF THE INVENTION

The field of the invention generally relates to an aspiration system for removing, by aspiration, undesired matter such as a thrombus from a fluid carrying cavity, duct, or lumen of the body, such as a blood vessel.

BACKGROUND

Thrombosis is managed by pharmacologic means and by interventional means. These include thrombectomy, and combinations of thrombectomy with pharmacologic agents.

Thrombectomy methods include breaking up and in many cases removing thrombus from a patient having thrombosis. Thrombectomy may be mechanical or non-mechanical, and may use catheter-based cutting or macerating elements, saline jets or aspiration of the thrombus.

A treatment method for removing undesired matter such as thrombus from a blood vessel of a patient involves use of an aspiration catheter having elongate shaft formed with an aspiration lumen extending therein. An aspiration catheter may also include a guidewire lumen for placement of a guidewire, which is used to guide the aspiration catheter to a target site in the body. By applying a vacuum (i.e. negative pressure) to a proximal end of the aspiration lumen, for example, with a syringe having a hub that is connected to the proximal end of the aspiration catheter, the matter can be aspirated into an aspiration port at the distal end of the aspiration catheter, into the aspiration lumen, and thus be removed from the patient.

SUMMARY OF THE INVENTION

In one embodiment, an aspiration system for removal of material from a lumen, cavity or duct of a patient includes an aspiration catheter having a proximal end and a distal end and configured to be inserted through a lumen of an elongate tubular member, the elongate tubular member configured for insertion into the vasculature of a subject and having a proximal end, a distal end, the lumen extending from the proximal end to the distal end, and an inner surface defined by the lumen, the aspiration catheter including a tubular aspiration member having a proximal end, a distal end, and a lumen, and configured to at least partially extend out of the lumen of the elongate tubular member at the distal end of the elongate tubular member and into the vasculature of the subject, an elongate support member coupled to the tubular aspiration member and extending between the proximal end of the aspiration catheter and the proximal end of the tubular aspiration member, a high pressure injection lumen extending within the elongate support member and having a proximal end adjacent the proximal end of the aspiration catheter and a distal end adjacent the distal end of the tubular aspiration member, the distal end of the high pressure injection lumen including a curved portion configured to change a direction of fluid flow through the high pressure injection lumen by at least about 90°, at least one orifice located at the distal end of the high pressure injection lumen configured to allow liquid injected through the high pressure injection lumen to be released into the lumen of the tubular aspiration member, and an annular seal carried by the tubular aspiration member and configured to create a liquid seal against the inner surface of the elongate tubular member.

BRIEF DESCRIPTION OF THE DRAWINGS

FIG. 3 is a sectional view of a standard aspiration system during aspiration.

FIG. 4 is a sectional view of the embodiment of FIGS. 1 and 2 during aspiration.

FIG. 5 is a sectional view of a standard aspiration system during aspiration, with a guidewire in place through the lumens.

FIG. 6 is a sectional view of the embodiment of FIGS. 1 and 2 during aspiration, with a guidewire in place through the lumens.

FIG. 15A is a sectional view of an aspiration system according to an embodiment of the disclosure invention.

FIG. 15B is a sectional view of an aspiration system according to an embodiment of the present disclosure.

FIG. 15C is a sectional view of an aspiration system according to an embodiment of the present disclosure.

FIG. 16 is a sectional view of an aspiration catheter according to an embodiment of the present disclosure.

FIG. 17 is a cross-sectional view of the aspiration catheter of FIG. 16, taken through line 17-17.

FIG. 25 is a perspective view of an aspiration system according to an embodiment of the present disclosure in use within a blood vessel.

FIG. 26A is a perspective view of an embodiment of a catheter joint.

FIG. 26B is a perspective view of a component of the catheter joint of FIG. 26A.

FIG. 27. is a perspective view of an aspiration catheter assembled with a dipping process according to an embodiment of the present disclosure.

FIG. 28 is a perspective view of a distal section of an aspiration (thrombectomy) catheter according to an embodiment of the present disclosure.

FIG. 33 is a perspective view of a distal section of a saline aspiration (thrombectomy) catheter according to an embodiment of the present disclosure.

FIG. 34A is a cross-section of the saline injection aspiration (thrombectomy) catheter of FIG. 33, taken along the line 34A-34A.

FIG. 34B is a cross-section of the saline injection aspiration (thrombectomy) catheter of FIG. 33, taken along the line 34B-34B.

FIG. 39. is a top view of a marker band during an assembly process according to an embodiment of the present disclosure.

FIG. 40. is a perspective view of a marker band during an assembly process according to an embodiment of the present disclosure.

FIG. 41. is an end view of a marker band during an assembly process according to an embodiment of the present disclosure.

FIG. 42. is an end view of a marker band during an assembly process using the slotted mandrel of FIG. 37 according to an embodiment of the present disclosure.

FIG. 44B is a view of an aspiration monitoring system according to a second embodiment of the present disclosure.

FIG. 48 is a plan view of a system for aspiration according to another embodiment of the present disclosure.

FIG. 49 is a detailed view of an aspiration monitoring system of the system for aspiration of FIG. 48.

FIG. 55A is a perspective view of an aspiration system according to an embodiment of the present disclosure in a first configuration.

FIG. 55B is a perspective view of the aspiration system of FIG. 55A in a second configuration.

FIGS. 56A-56C are perspective views of an aspiration catheter according to an embodiment of the present disclosure in three different configurations.

FIG. 69A is a view of a system for aspiration or fluid delivery.

FIG. 69B is an end view of the distal end of the aspiration catheter of the system for aspiration or fluid delivery of FIG. 69A.

FIG. 70 is a detail view of the connection of FIG. 69.

DETAILED DESCRIPTION

Figure 1:
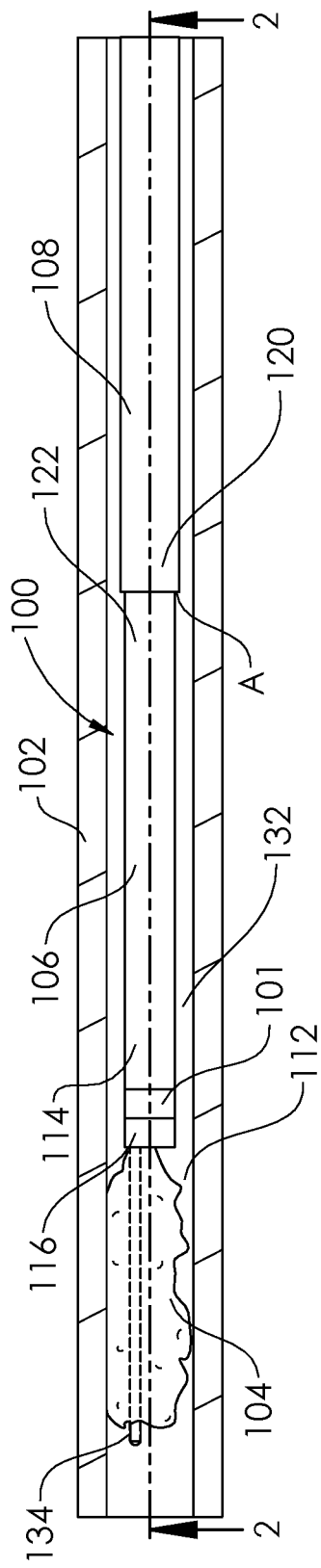
FIG. 1 is a side elevation view of an aspiration system according to an embodiment of the present disclosure.
Figure 2:
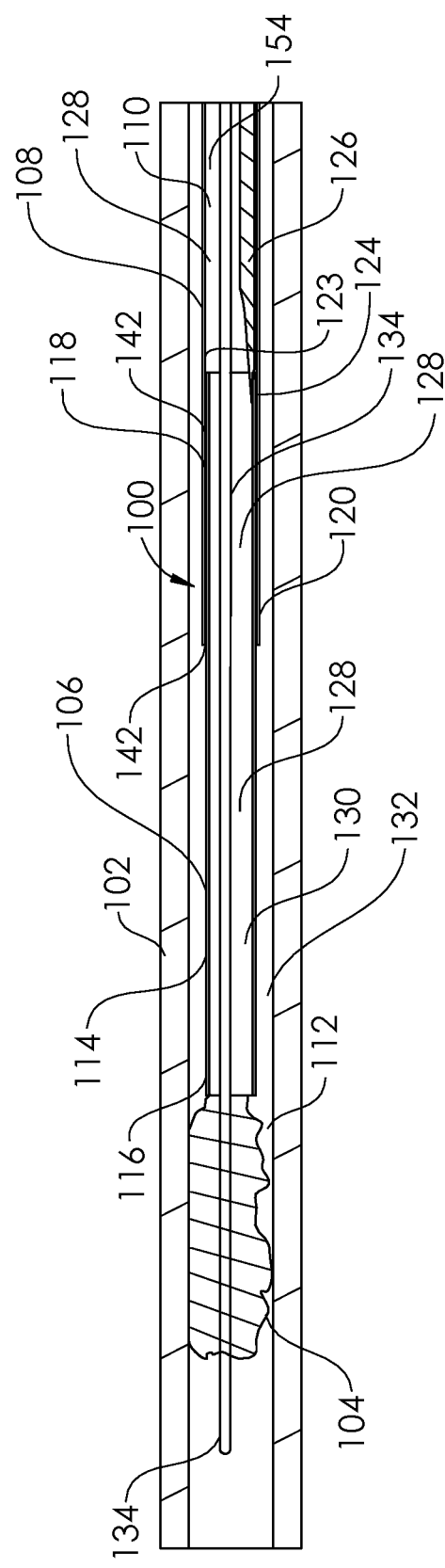
FIG. 2 is a cross-sectional view taken along line 2-2 of FIG. 1.

Referring first to FIGS. 1 and 2, the distal portion of an aspiration or thrombectomy system 100 is shown within a blood vessel 102 of a patient with thrombosis, including at least one thrombus 104. The blood vessel 102 may comprise a vein or an artery. For example, the blood vessel 102 may comprise one or more veins of the legs, including, but not limited to the femoral or iliac veins, or one or more veins of the upper extremities, including, but not limited to the subclavian, internal jugular or axillary veins. The blood vessel 102 may also comprise the inferior vena cava or superior vena cava. The blood vessel 102 may comprise an artery including, but not limited to a pulmonary artery, a coronary artery, a cerebral artery, an internal carotid artery, a femoral artery, an iliac artery, or a renal artery. The thrombectomy system 100 comprises a thrombectomy catheter 106 and a guiding catheter 108. The guiding catheter 108 may, for example, have an outer diameter of 6 French, an inner lumen diameter of approximately 0.183 cm (0.072 inches), and have a total length of approximately 100 cm. The thrombectomy catheter 106 is configured to be placed through the inner lumen 110 of the guiding catheter 108. The guiding catheter 108 may comprise a composite extruded and braided tubular structure, which has sufficient flexibility and pushability to reach a target area 112. The guiding catheter 108 may also have a pre-shaped tip. For example, the tip shape may aid in cannulating coronary arteries. The thrombectomy catheter 106 comprises a distal tube 114 which is configured to be extendable out of the inner lumen 110 of the guiding catheter 108, such that a distal end 116 of the distal tube 114 can be advanced a desired length into the blood vessel 102 so that it can be placed adjacent the target area 112. The proximal end 118 of the distal tube 114 is configured to remain within the inner lumen 110 of the guiding catheter 108, for example, at a region near the distal end 120 of the guiding catheter 108. In some embodiments, the thrombectomy catheter 106 includes a radiopaque marker 101, which may comprise a band secured to the thrombectomy catheter, and made from radiodense material, such as platinum, gold, or other similar materials. In some embodiments, the distal tube 114 may be formed of polymeric materials containing radiopaque material, such as titanium dioxide ($TiO_2$).

A sealing member 124 is carried by the proximal end 118 of the distal tube 114, and may comprise, for example, an annular seal attached to an outer cylindrical surface 122 of the distal tube 114. The thrombectomy catheter 106 also comprises a support member 126, for example a wire, a hypo tube, or a composite shaft, which is secured to the distal tube 114 by adhesive, mechanical attachment or other manners described herein. The support member 126 may be relatively stiff and may have a relatively small outer diameter so that it does not block the lumen 130 of the distal tube 114. The sealing member 124 is configured to seal off an annulus 142 between the distal tube 114 and an inner surface 123 defined by the inner lumen 110 of the guiding catheter 108 so that an extended lumen 128 is created, at least when a negative pressure gradient is placed between the proximal end 144 (FIGS. 4 and 6) of the guiding catheter 108 and the distal end 116 of the distal tube 114. The negative pressure gradient may result by coupling a vacuum source 146 to the proximal end of the guiding catheter 108. For example, a y-connector 148 may be sealingly coupled to the proximal end 144 of the guiding catheter 108, and the support member 126 may extend through the y-connector 148 and be sealed by the proximal seal 150 (e.g. hemostatic valve) of the y-connector 148. The vacuum source 146 may be coupled to the side port 152 (e.g. luer) of the y-connector 148. In some embodiments, the vacuum source 146 may comprise a 20 ml syringe, 30 ml syringe, or a larger syringe, that is lockable in its evacuated condition. An example is the VacLok® syringe sold by Merit Medical Systems, Inc. of South Jordan, Utah. In some embodiments, the syringe may be attached to the side port 152 of the y-connector 148 via extension tubing known in the art. In use, when the distal end 116 of the distal tube 114 is extended out of the distal end 120 of the guiding catheter 108 into the vasculature and adjacent a thrombus 104, and the sealing member 124 is sealingly located within the inner lumen 110 of the guiding catheter 108, the negative pressure gradient caused by the application of the vacuum source 146 causes the thrombus 104, or at least a portion thereof, to be aspirated through the extended lumen 128. While being aspirated, the thrombus 104, or a portion thereof, first enters the lumen 130 of the distal tube 114 and then enters the lumen cross-section 154a, 154b of the inner lumen 110 of the guiding catheter 108, not already taken up by the support member 126 (FIG. 8), or by the support member 126 and a guidewire 134 (FIG. 10), if a guidewire is left in place within the lumens 110, 130. The seal created by the sealing member 124 assures that blood 132 (FIGS. 1 and 2) will not enter into the extended lumen 128 (the combination of lumen 130 and the lumen cross-section 154 of the inner lumen 110) through location A.

Blood has a non-Newtonian viscosity, which is known to vary depending on the shear rate the blood experiences. The mean viscocity of blood can also be varied by factors including the amount of heparinization, or anti-coagulation, employed during an interventional procedure, which may include a thrombectomy procedure. Viscosities of around 0.0025 pascal-seconds (2.5 centipoise) have been measured in heparinized blood, and as heparinization may lower normal blood viscosity, embodiments of a sealing member 124 presented herein substantially prevent a liquid having a viscosity as low as 0.0025 pascal-seconds from passing through the annular space between the guiding catheter 108 and the distal tube 114 in a distal to proximal direction and into the inner lumen 110 of the guiding catheter 108 proximal to the sealing member 124 when a sufficient vacuum pressure is applied to the inner lumen 110 of the guiding catheter 108 to cause at least some aspiration. In some embodiments, the sufficient vacuum pressure may be about −34,474 pascal (−5 pounds per square inch) or lower. In some embodiments, the sufficient vacuum pressure may be about −46,662 pascal (−6.8 pounds per square inch) or lower. In some embodiments, the sufficient vacuum pressure may range between about −82,737 pascal (−12 pounds per square inch) and about −95,526 pascal (−14 pounds per square inch). In some embodiments, the sufficient vacuum pressure may be about −89,631 pascal (−13 pounds per square inch).

Figure 11:
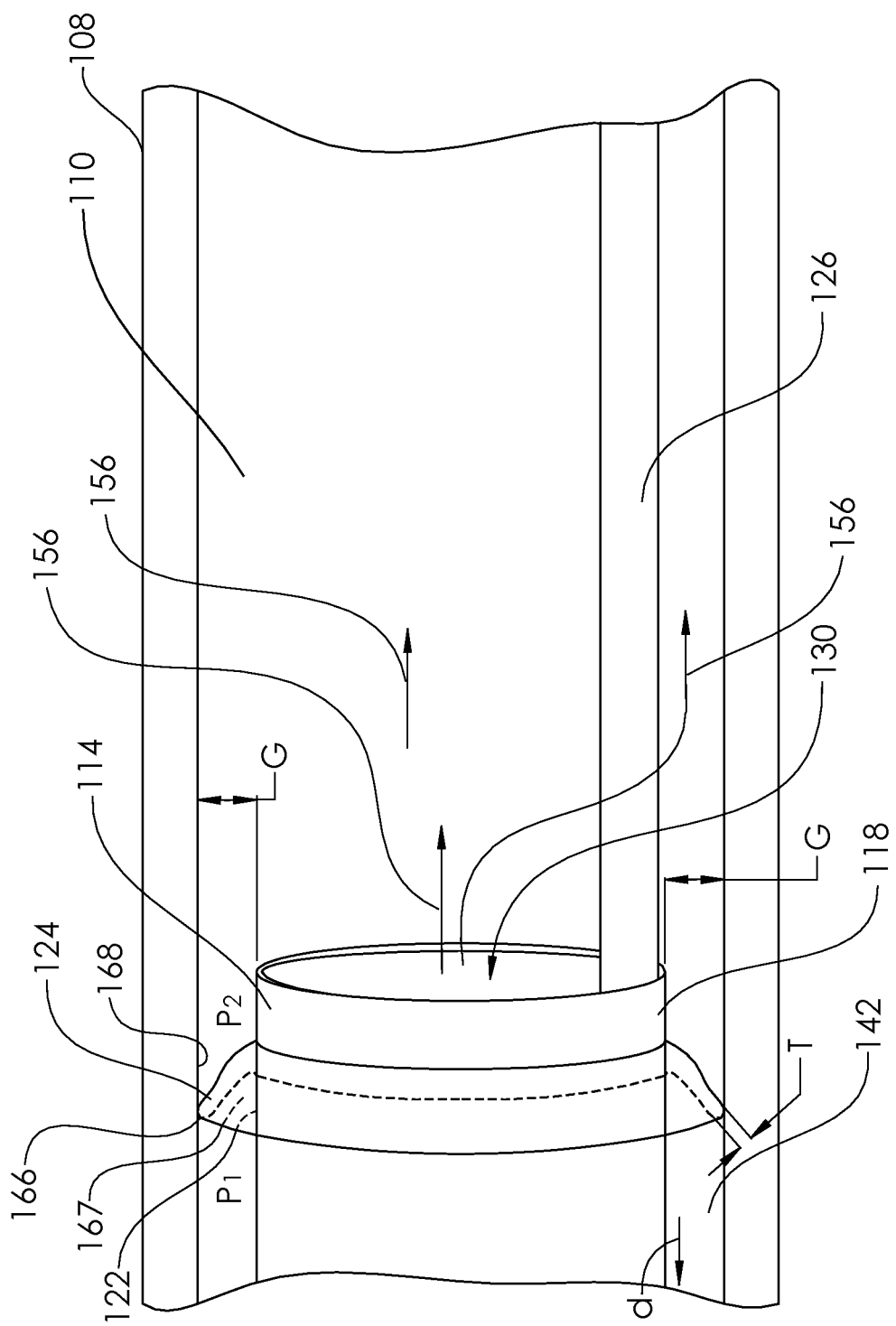
FIG. 11 is a view of an aspiration system according to an embodiment of the present disclosure during aspiration.
Figure 12:
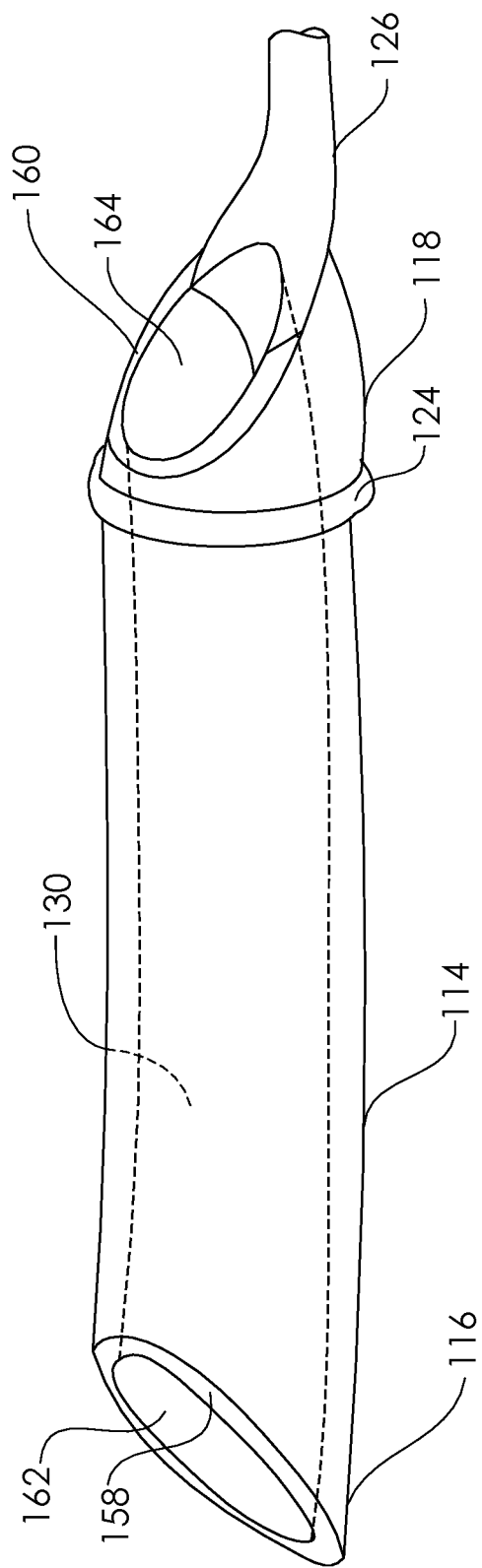
FIG. 12 is a perspective view of a distal section of an aspiration (thrombectomy) catheter according to an embodiment of the present disclosure.

FIG. 11 illustrates the fluid flow 156 (e.g. blood, thrombus, macerated thrombus) out of the proximal end 118 of the distal tube 114 (lumen 130) and through the inner lumen 110 of the guiding catheter 108. In the embodiment of the thrombectomy system 100 illustrated in FIGS. 1 and 2, the distal tube 114 has a lumen 130 configured for tracking over the guidewire 134. The guidewire 134 (e.g. 0.014″ coronary guidewire) may be used to guide the thrombectomy catheter 106 through the blood vessel 102, with the lumen 130 of the distal tube 114 acting as a single-operator exchange lumen. In some embodiments, the length of this lumen 130 may be between 5 cm and 35 cm. In some embodiments, it may be between 10 cm and 30 cm. In some embodiments, it may be between 15 cm and 25 cm. In some embodiments, it may be about 25 cm. As illustrated in FIG. 12, the distal tube 114 may have a skive 158 at its distal end 116 and/or a skive 160 at its proximal end 118. The skives 158, 160 may serve at least two purposes. First they aid in the tracking of the distal tube 114 and thus the thrombectomy catheter 106 through the blood vessel 102, including any thrombus 104 or atherosclerotic plaque (not shown), past the distal end 120 of the guiding catheter 108, and in and out of the y-connector 148, including the proximal seal 150. Second, the skives 158, 160 increase the cross-section area at the entry (or exit) points of the lumen 130 of the distal tube 114, thus lowering resistance to flow, and allowing, for example, relatively larger pieces or portions of thrombus to enter the lumen 130. The distal tube 114 in FIG. 12 is depicted in a slightly curved state so that the openings 162, 164 at either end of the lumen 130 face the viewer, so that the skives 158, 160 may be better appreciated.

Figure 13:
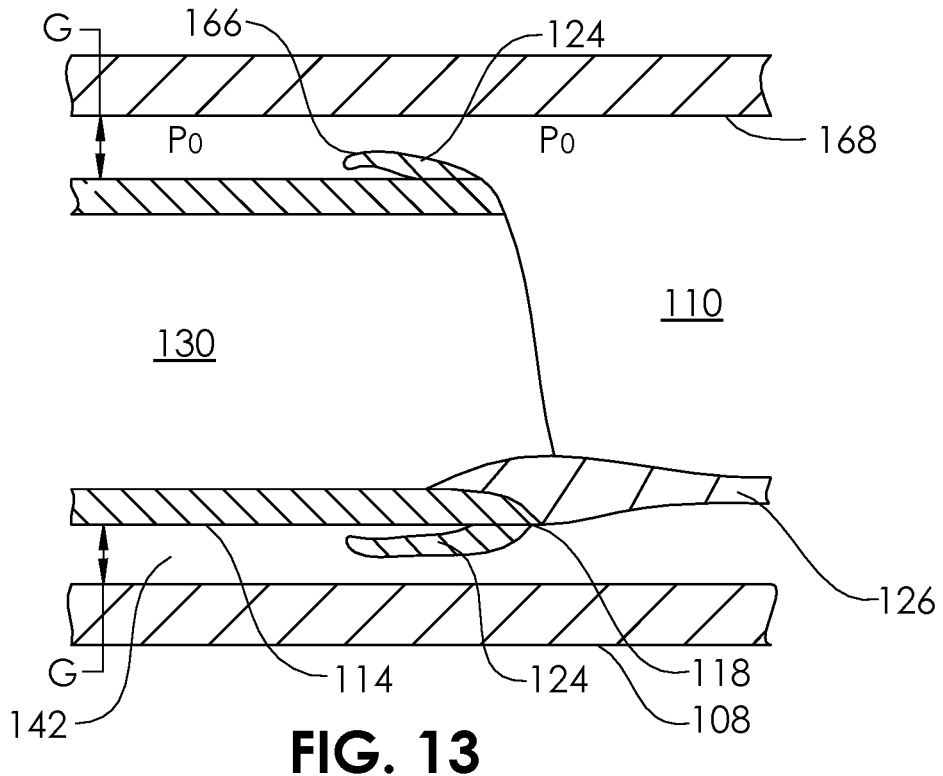
FIG. 13 is a sectional view of an aspiration system according to an embodiment of the present disclosure prior to aspiration.
Figure 14:
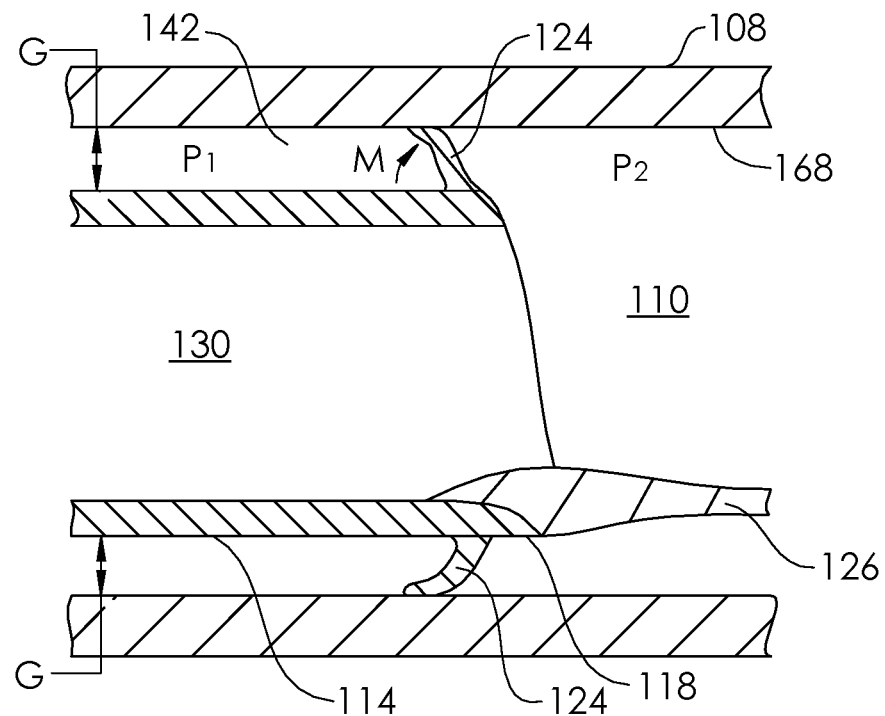
FIG. 14 is a sectional view of an aspiration system according to an embodiment of the present disclosure during aspiration.

Returning to FIG. 11, the sealing member 124 is shown as an annular seal with a distally facing lip 166. An annular concavity 167 extends circumferentially around the distal tube 114 between the distally facing lip 166 and the outer cylindrical surface 122 of the distal tube 114. In some embodiments, the sealing member 124 may be made from a number of elastomeric materials including silicone, EPDM, polyurethane, or thermoplastic elastomers, such as PEBAX or Santoprene®. The thin-walled construction of the distal tube 114 allows a finite gap G between the distal tube 114 and the inner lumen 110 of the guiding catheter 108, while still maintaining a relatively large lumen 130 in the distal tube 114, in some embodiments as large as about 0.152 cm (0.060 inches) or larger (for a 6F guiding catheter compatible thrombectomy catheter 106). In some embodiments, the gap G is 0.003″ or more on each side, and the thin lip 166 may have a thickness T of about 0.000635 cm (0.00025 inches) to about 0.00508 cm (0.0020 inches). In other embodiments, the thickness T may be between about 0.0019 cm (0.00075 inches) and about 0.0038 cm (0.0015 inches). On other embodiments, the thickness T may be between about 0.00254 cm (0.001 inches) and about 0.00317 cm (0.00125 inches). With a gap G on the order of 0.0076 cm (0.003 inches) or more per side, there would be a risk of some movement of thrombus or macerated thrombus through the annulus 142 in direction d, due to agitation, and perhaps into the blood vessel 102, creating a risk of embolization of a loose thrombus. However, the addition of the distally facing lip 166 allows the annulus 142 to be completely sealed whenever the vacuum source 146 (FIGS. 4 and 6) is applied, causing suction within the inner lumen 110 of the guiding catheter, and thus a pressure $P_2$ proximal to the distally facing lip 166 that is less than the pressure $P_1$ distal to the distally facing lip 166. Because the distally facing lip 166 is made from a flexible material, and/or has a relatively small thickness T, the positive pressure gradient from the $P_1$ (distal) side to the $P_2$ (proximal side) ($P_1-P_2>0$) will cause the distally facing lip 166 to be forced against the inner wall 168 of the guiding catheter 108, thus sealing it. The maximum outer diameter of the distally facing lip 166 may actually be smaller than the inner diameter of the inner lumen 110 of the guiding catheter 108, because it will flex (e.g., by moment M) from a first configuration (FIG. 13) to a second configuration (FIG. 14) when activated by the positive pressure gradient ($\Delta P=P_1-P_2$), in order to seal off the annulus 142. The benefit of having a distally facing lip 166 whose maximum outer diameter is smaller than the inner diameter of the inner lumen 110 of the guiding catheter 108 (when not activated by pressure), is that during tracking of the thrombectomy catheter 106, when the vacuum source 146 is not being applied, there is no seal between the distally facing lip 166 and the inner wall 168 of the guiding catheter 108, and thus there is less axial friction, thus making it easier to track and slide the thrombectomy catheter freely (longitudinal translation), providing both low axial resistance to motion (less drag), and high precision of motion (better "feel"). Thus, the distally facing lip 166 only expands when it is needed (i.e. during aspiration). In some embodiments, the distal facing lip 166 may be made using a dipping process. In some embodiments, the dipping process may be a polyurethane dipping process. In some embodiments the distally facing lip 166 may be made from non-elastomeric materials, such polyolefins, nylon, as the pressure-activated sealing does not require elastomeric compression. In some embodiments, the distally facing lip 166 may be bonded to the distal tube 114 with adhesive, epoxy, or by thermal bonding methods. In some embodiments, the seal should be liquid tight, or water tight (saline tight), and in some embodiments need not be air tight (gas tight). In some cases liquid tight may be defined as not allowing any substantial amount of blood to pass through the annulus 142. The sealing may be aided by blood viscosity, the length of the annulus 142 (distal to the sealing member 124), and the dimension of the gap G (FIG. 11). For example, a higher blood viscosity, longer annulus 142 length, and a smaller gap G dimension each serve alone or in combination to increase the sealing capacity (decrease the possibility of fluid passage through the annulus 142).

In some embodiments, the distal facing lip 166 is configured to maintain a seal when a positive pressure gradient ($\Delta P=P_1-P_2$) of about 46,662 pascal (350 mm Hg) or higher is maintained. In some embodiments, the aspiration pressure may be maintained using a vacuum pump as the vacuum source 146. In some embodiments, the vacuum pump provides a relatively constant pressure gradient of about 46,662 pascal (350 mm Hg) to about 53,328 pascal (400 mm Hg).

In some embodiments, a 20 ml to 60 ml syringe is evacuated in order to serve as the vacuum source 146. In some embodiments, a 30 ml syringe is evacuated in order to serve as the vacuum source 146. In some embodiments, the evacuated 30 ml syringe provides a plateau pressure gradient of about 75,993 pascal (570 mm Hg) to about 89,626 pascal (670 mm Hg). As described, heparinized blood tends to have a viscosity of about 0.0025 pascal-seconds (2.5 cP) or higher. In some embodiments, the distally facing lip 166 is configured to seal against the inner wall 168 of the guiding catheter 108 so that a 0.0025 pascal-seconds liquid will not significantly pass distal to proximal when a distal to proximal positive pressure gradient ($\Delta P = P_1 - P_2$) of 46,662 pascal (350 mm Hg) is applied. In some embodiments, the distally facing lip 166 is configured to not seal against the inner wall 168 of the guiding catheter and thus not stop the passage of a liquid from proximal to distal (i.e. through the annulus 142) when a proximal to distal positive pressure gradient ($\Delta P = P_2 - P_1$) of 46,662 pascal (350 mm Hg) is applied.

Figure 7:
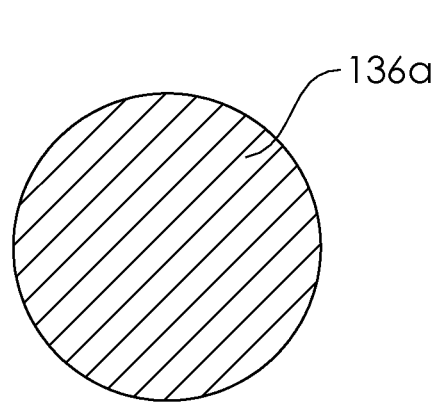
FIG. 7 is a view of the lumen cross-section in a standard aspiration catheter or in the distal tube of the embodiment of FIGS. 1 and 2.
Figure 8:
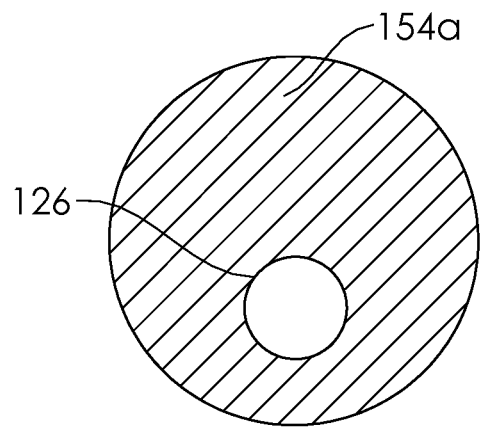
FIG. 8 is a view of the lumen cross section in a portion of a guiding catheter of the embodiment of FIGS. 1 and 2.
Figure 9:
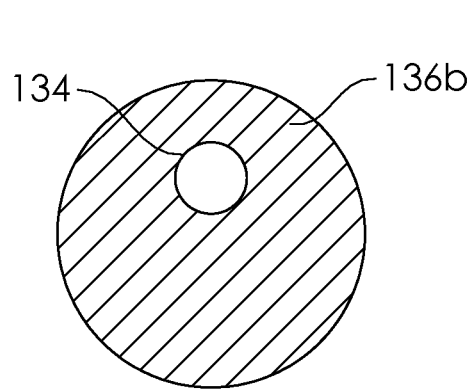
FIG. 9 is a view of the lumen cross-section in a standard aspiration catheter or in the distal tube of the embodiment of FIGS. 1 and 2, with a guidewire in place through the lumen.
Figure 10:
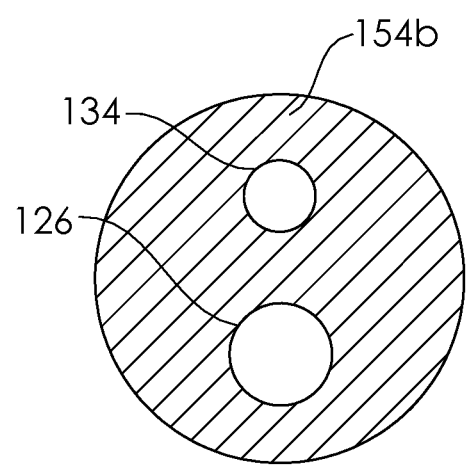
FIG. 10 is a view of the lumen cross section in a portion of a guiding catheter of the embodiment of FIGS. 1 and 2, with a guidewire in place through the lumen.

FIG. 6 illustrates the aspiration flow path and FIGS. 9 and 10 illustrate the lumen cross-sections 136b, 154b if the guidewire 134 is left in place during aspiration. FIG. 4 illustrates the aspiration flow path and FIGS. 7 and 8 illustrate the lumen cross-sections 136a, 154a if the guidewire 134 is not left in place during aspiration, for example, if it is removed. Starting with this latter "no guidewire" condition, FIG. 7 illustrates a lumen cross-section 136a, which may represented by a lumen 138 of a standard thrombectomy catheter 140 in FIG. 3, or by the lumen 130 of the thrombectomy catheter 106 of an embodiment of the present disclosure in FIG. 4. A comparison between the flow characteristics of the standard thrombectomy catheter 140 and the embodiment of the thrombectomy system 100 of FIGS. 1 and 2 is presented below.

The standard Hagen-Poiseuille Law flow equation used to calculate the flow of fluids (e.g. blood and/or macerated thrombus) is:

$$Q = \frac{\Delta P \pi D^4}{128 \,\mu L}$$

where L is the length of a particular flow path, $\Delta P$ is the pressure gradient between one end of the flow path and the other end of the flow path, D is the diameter of the flow path, and $\mu$ is the viscosity of the fluid.

Because luminal cross-sectional areas are often non-circular, the term Hydraulic Diameter ($D_H$) is often substituted for diameter D. Hydraulic Diameter ($D_H$) represents the effective diameter of a circular cross-section that behaves the same as a non-circular cross-section. The Hydraulic Diameter ($D_H$) equation is:

$$H_D = \frac{4A}{p}$$

where A is the cross-sectional area of the lumen, and p is the summation of the perimeter of all of the luminal walls on cross-section.

Combining these two equations, the standard Hagen-Poiseuille Law flow equation for a particular Hydraulic Diameter ($D_H$) is:

$$Q = \frac{\Delta P \pi D_H^4}{128 \,\mu L}$$

Using the Ohm's Law analogy for fluid flow, produces the equation:

$$Q = \frac{\Delta P}{R}$$

where R is the Resistance (to fluid flow), given thus by the equation:

$$R = \frac{128 \,\mu L}{\pi D_H^4}$$

As differing lumen cross-sections 136, 154 are arrayed serially in the systems being discussed, the serial resistance equation will be used, the equation being:

$$R_T = R_1 + R_2 + R_3 + \ldots$$

where $R_T$ is the total resistance, and $R_1$, $R_2$, $R_3$, etc. are individual serial resistances.

The intention is to compare the total (flow) resistance of a first thrombectomy system ($R_{T1}$) with the total resistance of a second thrombectomy system ($R_{T2}$). Thus, the constant $128/\pi$ can be removed from the comparative term, leaving $\mu L/D_H^4$. Additionally, though blood is non-Newtonian, and thus may exhibit variance in viscosity at different shear rates, the variation of the effective viscosity of a thrombus/macerated thrombus/blood slurry is not expected to be significant among the different lumen conditions described. Therefore, the viscosity ($\mu$) term may also be removed from the comparative term. This leaves a comparative term of:

Comparative Flow Resistance ($R_C$) = $L/D_H^4$

Comparative Flow Resistance ($R_C$) can be calculated using the units (l/cm³).

Returning to the standard thrombectomy catheter 140 of FIG. 3, the entire length $L_1$ of the catheter in some models is about 140 cm and has a circular cross-sectional diameter $D_1$ of its lumen 138 of about 0.11 cm (0.042 inches). Because the lumen 138 is circular, 0.11 cm (0.042 inches) is also the Hydraulic Diameter ($D_H$). In comparison, the embodiment of the thrombectomy system 100 of FIG. 4, includes a first length $L_2$ representing the length of the distal tube 114 of the thrombectomy catheter 106, and in one embodiment $L_2$ is about 25 cm. In this particular embodiment, the lumen 130 of the distal tube 114 may have a circular cross-sectional diameter $D_2$ of its lumen 130 of about 0.15 cm (0.060 inches) The thrombectomy system 100 is inserted through a guiding catheter 108 having a lumen inner diameter of about 0.183 cm (0.072 inches) and a length of about 100 cm, thus having a flow length L3 of about 100 cm. Assuming a support member 126 embodiment comprising a substantially rectangular cross-section stainless steel wire having a minor dimension of about 0.0305 cm (0.012 inches) and a major dimension of about 0.0508 cm (0.020 inches), the Comparative Flow Resistance ($R_C$) may be calculated for the standard thrombectomy catheter 140 and the thrombectomy system 100 in their "no guidewire" configurations of FIGS. 3 and 4, respectively. Table 1 demonstrates that the Comparative Flow Resistance ($R_{C1}$) of the thrombectomy system 100 is only about 15% the Comparative Flow Resistance ($R_{C2}$) of the standard thrombectomy catheter 140.

TABLE 1

| Condition | $R_{c1}$ (1/cm³) | $R_{c2}$ (1/cm³) | $R_{c1}/R_{c2}$ |
|---|---|---|---|
| No Guidewire (FIGS. 3 and 4) | 160,822 | 1,080,926 | 0.15 |
| Guidewire (FIGS. 5 and 6) | 320,704 | 1,080,926 | 0.30 |

The standard thrombectomy catheter 140 in FIG. 5 has a guidewire 134 within the length of its lumen 138. The thrombectomy system 100 of FIG. 6 has a 0.014" diameter guidewire 134 (0.036 cm) within the length of the lumen 130 of the distal tube 114 and the inner lumen 110 of the guiding catheter 108. The thrombectomy system 100 of FIG. 6 also has a support member 126 having cross-sectional dimensions of 0.0305 cm×0.0508 cm (0.012 inches×0.020 inches) within the length of the inner lumen 110 of the guiding catheter 108. Table 1 demonstrates that the Comparative Flow Resistance ($R_{C1}$) of the thrombectomy system 100 is only about 30% the Comparative Flow Resistance ($R_{C2}$) of the standard thrombectomy catheter 140. This means that at a particular negative pressure gradient, the aspiration flow rate through the thrombectomy system 100 can be as much as 3.33 times more than the aspiration flow rate through the standard thrombectomy catheter 140.

A test was performed wherein a 30 ml vacuum was locked onto an extraction syringe, and sealed with a closed stopcock. The extraction syringe and stopcock were then attached to a catheter/catheter system and the tip of the catheter placed in a beaker of water. The stopcock was then opened and the time was measured for the 30 ml syringe to fill with water. The data is listed in Table 2.

TABLE 2

| System | Time to fill 30 ml syringe (seconds) |
|---|---|
| Medtronic Export AP | 25 |
| Prototype with 25 cm long, 0.147 cm (.058 inches) ID distal tube, and 0.0305 cm × 0.0508 cm (0.012 inches × 0.020 inches) support member in 0.183 cm (.072 inches) ID × 100 cm long guiding catheter – distal tube extending 25 cm from guiding catheter | 7.2 |
| Prototype with 25 cm long, 0.147 cm (.058 inches) ID distal tube, and 0.0305 cm × 0.0508 cm (0.012 inches × 0.020 inches) support member in 0.183 cm (.072 inches) ID × 100 cm long guiding catheter – distal tube extending 5 cm from guiding catheter | 6.7 |

Published data using a similar 30 ml syringe water vacuum test shows Peak Extraction Rate (ml/sec) for several thrombus aspiration catheters. The peak extraction rate ranged from 0.94 ml/second to 1.71 ml/second (Table 3). Published in "Comparison of Dimensions and Aspiration Rate of the Pronto® V3, Pronto® LP, Export® XT, Export® AP, Fetch®, Xtract™, Diver C.E.™ and QuickCat™ Catheters" (ML1623 Rev. F 12/09 c2009 Vascular Solutions, Inc.) In comparison, the prototype thrombectomy system 100 tested in the two conditions of Table 1, demonstrated an average extraction rate of 3.6 ml/second to 4.0 ml/second, 2.1 to 2.3 times the peak extraction rate of the highest performing catheter (Pronto V3) in the published data set. And it should be mentioned that the designs of the thrombus aspiration catheters of the Table 3 test data are such that there is no guidewire within their lumen (as in FIG. 3) during aspiration, and the prototype thrombectomy system 100 tested also did not have a guidewire within its lumens during testing (as in FIG. 4). In use, for aspirating body fluids and materials such as blood and thrombus, embodiments of the thrombectomy system 100 of the present disclosure have significantly higher potential to remove thrombus more quickly and more completely than a standard thrombectomy catheter 140, such as those represented in the published data. The amount of vacuum present at the lumen 130 at the distal end 116 of the distal tube 114 may be up to twice that (or more) of the amount of vacuum present at the distal tip of the lumen 138 of a standard thrombectomy catheter 140, which attests to larger forces pulling the thrombus 104 into the lumen 130.

TABLE 3

| System | Peak Extraction Rate (ml/sec) of water evacuated by 30 ml syringe |
|---|---|
| Pronto ® V3 (Vascular Solutions, Inc.) | 1.71 |
| Pronto ® LP (Vascular Solutions, Inc.) | 0.94 |
| Export ® XT (Medtronic, Inc.) | 1.27 |
| Export ® AP (Medtronic, Inc.) | 1.44 |
| Fetch ® (Medrad/Possis) | 1.55 |
| Xtract ™ (Volcano/Lumen Biomedical) | 1.24 |
| Diver C.E. ™ (Invatec) | 1.04 |
| QuickCat ™ (Spectranetics) | 1.11 |

FIG. 15A illustrates an embodiment of the thrombectomy system 100, wherein the thrombectomy catheter 106 includes a sealing member 124 that is an o-ring 174 having a custom cross-section having a wider base portion 170 having a width W and a wiper blade portion 172 having a width w, that is smaller than width W. Though the maximum outer diameter of the o-ring 174 of this embodiment should be larger than the inner diameter of the inner lumen 110 of the guiding catheters 108 with which it is compatible (for sealable coupling), the thinner the width w of the wiper blade portion, the less drag and the greater feel is achieved. The distal tube 114 includes an annular groove 180, having a width large enough to seat the base portion 170 of the o-ring 174. In FIG. 15A, the distal tube 114 of the thrombectomy catheter 106 is shown with a distal skive 158, but without a proximal skive (160 in FIG. 12). As mentioned, numerous combinations of the skives 158, 160 are contemplated and are not limiting. FIG. 15B illustrates a closeup of an embodiment of the thrombectomy system 100, wherein the thrombectomy catheter 106 includes a sealing member 124 that is an o-ring 174 having an x-shaped cross-section 178. FIG. 15C illustrates a closeup of an embodiment of the thrombectomy system 100, wherein the thrombectomy catheter 106 includes a sealing member 124 that is an o-ring 174 having a circular cross-section 176. Numerous other o-ring cross-sections are contemplated. The annular groove 180 has enough width to seat the corresponding o-ring cross-sections 176, 178 of the embodiments of FIGS. 15B and 15C. A lip, such as the distally facing lip 166 of the embodiment of the thrombectomy system 100 of FIG. 11, or a seal, such as the o-ring 174 having a wiper blade portion 172 of FIG. 15A, may have several optional embodiments in which their maximum outer diameter is constructed to different diameters in relation to the inner diameter of the guiding catheter 108. For example, in some embodiments, the outer diameter may be in rubbing relation to the inner diameter of the guiding catheter 108. In some embodiments, the outer diameter may be in touching relation to the inner diameter of the guiding catheter 108. In some embodiments, the outer diameter may be in close clearance relation to the inner diameter of the guiding catheter 108. In some embodiments, the outer diameter may be in a non-touching relation to the inner diameter (inner wall 168) of the guiding catheter 108. In some embodiments, there may me multiple features, having a combination of these relationships (rubbing, touching, etc.). In some embodiments, the sealing member 124 may be an inflatable balloon, whose diameter and/or inflation pressure may be controlled.

An alternative thrombectomy system 105 is illustrated in FIGS. 16-17 and comprises an aspiration catheter 111. The aspiration catheter 111 includes a distal tube 107 coupled to a support member 109. The aspiration catheter 111 is configured to be placed through a guiding catheter or any elongate tubular member, with the support member 109 extending proximally from the guiding catheter such that the support member 109 may be grasped and manipulated by a user, to move the aspiration catheter 111. An annular seal 103 is configured to provide a liquid seal between the distal tube 107 of the aspiration catheter 111 and an internal wall in the lumen of a guiding catheter, such as the inner wall 168 of the guiding catheter 108 in FIG. 15A. In the embodiment of FIGS. 16-17, the annular seal 103 comprises an o-ring 113 which is carried on an external surface 115 of the distal tube 107 of the aspiration catheter 111. In some embodiments, the o-ring 113 has an initial unstressed inner diameter which is less than an outer diameter of the distal tube 107. The o-ring 113 comprises an elastic material, and thus, the o-ring 113 is distended and placed over the external surface 115 of the distal tube 107. The o-ring 113 is thus carried by the distal tube 107 in a stressed state which forms a seal between the o-ring 113 and the external surface 115 of the distal tube 107. The o-ring 113 may additionally be secured to the external surface 115 of the distal tube 107 so that it cannot be significantly moved longitudinally in relation to the distal tube 107, for example, with adhesive or epoxy, or bookended between two separate lengths of shrink tubing that is shrunk over the distal tube 107. In some embodiments, the o-ring 113 in its distended state may add between about 0.003 inches (0.076 mm) to about 0.008 inches (0.203 mm) over the outer diameter of the distal tube 107. In some embodiments, an elastomeric coating 117 may be applied over the o-ring 113 and the external surface 115 of the distal tube 107. The elastomeric coating 117 may comprise a dip coating, such as a dip-coatable polyurethane, and may be applied to cover the external surface 115 at a first side 119 adjacent the o-ring 113, and to a second side 121 adjacent the o-ring 113. The elastomeric coating may have a thickness to of 0.001 inches (0.025 mm) or less, or about 0.0007 inches (0.018 mm), thus increasing the diameter over the external surface 115 or the outer diameter of the o-ring 113 by 0.002 inches (0.051 mm) or less, or by about 0.0014 inches (0.036 mm). In some embodiments, the distal tube 107 has an outer diameter of between about 0.065 inches (1.65 mm) and about 0.069 inches (1.75 mm), or about 0.067 inches (1.70 mm). In some embodiments, the addition of both the o-ring 113 and the elastomeric coating 117, creates an annular seal 103 having an unstressed (uncompressed) outer diameter of between about 0.070 inches (1.78 mm) and about 0.074 inches (1.88 mm), or about 0.072 inches (1.83 mm). These particular embodiments may be appropriate for applications in the coronary arteries. Further embodiments are contemplated that are appropriate for other portions of the vascular anatomy, including blood vessels that on the average are larger or even smaller than the coronary blood vessels. The dimensions of the components described (o-ring 113, elastomeric coating 117, etc.) may be scaled accordingly. The range of catheter sizes may include catheter diameters of between about 2 French and about 12 French.

The elastomeric coating 117 may be applied to the distal tube 107 and o-ring 113 by dip coating in some embodiments, prior to the attachment of the support member 109 to the distal tube 107. For example, a mandrel may be placed within the lumen 125 of the distal tube 107 to support the structure of the distal tube 107 and the preclude the dip coating material from being applied to an inner surface 127 of the lumen 125 of the distal tube 107. The proximal end 129 of the distal tube 107 may then be dipped into the dip coating material up to a depth $d_d$. The dipped distal tube 107 and o-ring 113 may then be removed from the container of dip coating material so that a relatively thin layer of the elastomeric coating 117 may be allowed to form. In some embodiments, a two-part mixture is formed to initiate polymerization of the final elastomeric coating 117. In other embodiments, a polymer may be dissolved or within a solvent, so that the solvent may evaporate from the material to form the elastomeric coating 117. The elastomeric coating 117 serves to adhere to the distal tube 107 on either end of the o-ring 113, and to secure the o-ring 113 to the distal tube. Suitable o-ring 113 materials include EPDM, silicone, Buna-N. Suitable elastomeric coatings 117 include polyurethane, santoprene. A significantly large range of durometers may be chosen for both the o-ring 113 and the elastomeric coating 117. In some embodiments, the o-ring 113 may even be a substantially non-elastomeric material, as the elastomeric coating 117 may be configured to provide sufficient compliance and/or elasticity. After the elastomeric coating 117 cures, forms or solidifies, the mandrel may be removed, and the support member 109 secured to the distal tube 107. In some embodiments, a mandrel having a non-circular cross-section may be configured to be placed in the lumen 125 after the support member 109 has already been secured to the distal tube 107, so that the elastomeric coating 117 may be subsequently applied without dip coating material being applied to an inner surface 127 of the lumen 125 of the distal tube 107. The depth $d_d$ may vary from between 0.150 inches (0.38 cm) and the entire length of the distal tube 107, which may be between about 2 cm and about 20 cm. An annular seal 103 that comprises both the o-ring 113 and the elastomeric coating 117 has a more gradual change in outer diameter than an annular seal 103 comprising only the o-ring 113. A first diametric transition 131 and a second diametric transition 133 are shown in FIG. 16, and can allow smooth longitudinal motion during engagement of the annular seal 103 with the inner wall 168 of the guiding catheter 108 (FIG. 15A). In addition, the elastomeric coating 117 maintains the o-ring 113 securely on the external surface 115 of the distal tube 107, and has good adherence to the external surface 115 because of a relatively large cylindrical adhesion or engagement area over the length equal to the dipping depth $d_d$. In some embodiments, the elastomeric coating 117 may be instead replaced by a shrink tube that is shrunk over the o-ring and at least a portion of the external surface 115 of the distal tube 107. The shrink tubing may comprise relatively low durometer PEBAX® shrink tubing.

In one embodiment, an aspiration system for removal of material from a lumen, cavity or duct of a patient includes an aspiration catheter having a proximal end and a distal end and configured to be inserted through a lumen of an elongate tubular member, the elongate tubular member configured for insertion into the vasculature of a subject and having a proximal end, a distal end, the lumen extending from the proximal end to the distal end, and an inner surface defined by the lumen, the aspiration catheter including a tubular aspiration member having a proximal end, a distal end, and a lumen, and configured to at least partially extend out of the lumen of the elongate tubular member at the distal end of the elongate tubular member and into the vasculature of the subject; an elongate support member coupled to the tubular aspiration member and extending between the proximal end of the aspiration catheter and the proximal end of the tubular aspiration member; and an annular seal carried by the tubular aspiration member and configured to create a liquid seal against the inner surface of the elongate tubular member, wherein the annular seal comprises an o-ring. In some embodiments the o-ring has an unstressed inner diameter and is carried by an external portion of the tubular aspiration member having an external diameter, and wherein the unstressed inner diameter of the o-ring is less than the external diameter of the external portion of the tubular aspiration member. In some embodiments, the annular seal further comprises an elastomeric coating covering an external portion of the o-ring and an external portion of the tubular aspiration member adjacent the o-ring. In some embodiments, the elastomeric coating comprises polyurethane. In some embodiments, the elastomeric coating is a dip coating. In some embodiments, the elastomeric coating has a thickness of less than 0.001 inches (0.025 mm). In some embodiments, the elongate support member comprises a metallic material. In some embodiments, the elongate support member comprises a hypo tube. In some embodiments, wherein the inner surface of the elongate tubular member is located adjacent the distal end of the elongate tubular member. In some embodiments, the elastomeric coating has a longitudinal length that is less than the longitudinal length of the tubular aspiration member.

Figure 18:
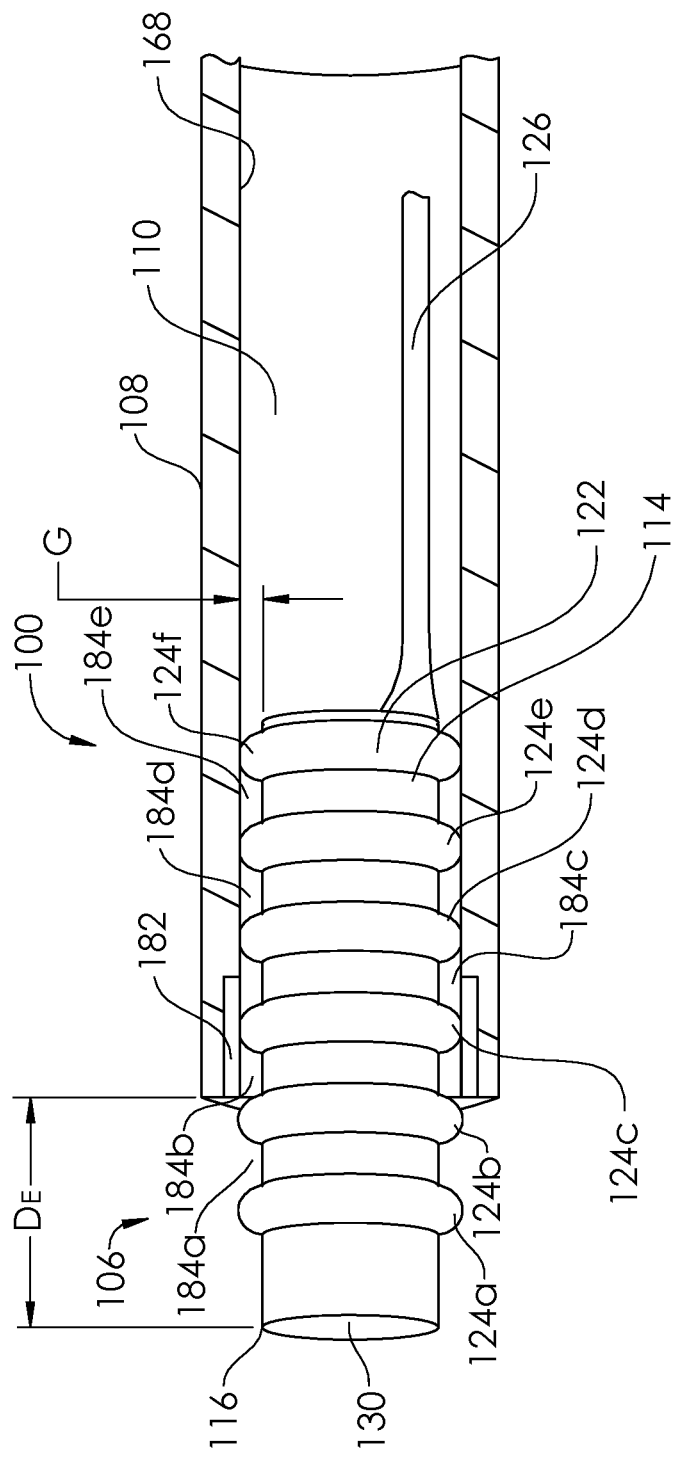
FIG. 18 is a partially sectional view of an aspiration system according to an embodiment of the present disclosure.

FIG. 18 illustrates an embodiment of a thrombectomy system 100 having multiple sealing members 124, denoted by 124a, 124b, 124c, 124d, 124e, and 124f. In some embodiments, the sealing members 124a-f may be annular seals, such as any of the embodiments described herein. In some embodiments, the guiding catheter 108 may be from a different or unknown supplier and it may be difficult to know the true inner diameter of the inner lumen 110 along a significant length of the distal portion of the guiding catheter 108. However, it may be possible for the user to measure the inner diameter at a distal portion 182 of the guiding catheter 108 (for example, using sterile pin or plug gauges). The multiple sealing members 124a-f make it possible to adjust the distance $D_E$ that the inner tube 114 extends from the guiding catheter 108, while assuring a sealing relationship between the particular sealing member 124a-f and the inner diameter of the guiding catheter 108 at the distal portion 182. For example, when sealing member 124a is sealingly engaged with the inner diameter of the guiding catheter 108 at the distal portion 182, $D_E$ is much shorter than when sealing member 124f is sealingly engaged with the inner diameter of the guiding catheter 108 at the distal portion 182. Thus, in use by the physician, the distal end 116 of the distal tube 114 can be brought into ideal position in relation to the thrombus 104 (FIGS. 1 and 2), for example, just proximal to the thrombus 104. Additionally, the short axial length of contact of each of the sealing members 124a-f with the inner wall 168 of the guiding catheter 108 summed together is much less than if the entire outer cylindrical surface 122 of the distal tube 114 were a cylindrical seal, and this lowers the drag and increases the feel. Multiple axial spaces 184a-e, located between the sealing members 124a-f, represent the majority of the length of the distal tube 114, and thus gap G can be large enough (e.g. 0.0076 cm (0.003 inches) or greater per side) so that even in tortuosities of the blood vessel 102, where the catheters may be curved or angled, the drag is not unacceptably increased and the feel is not unacceptably decreased.

Figure 19:
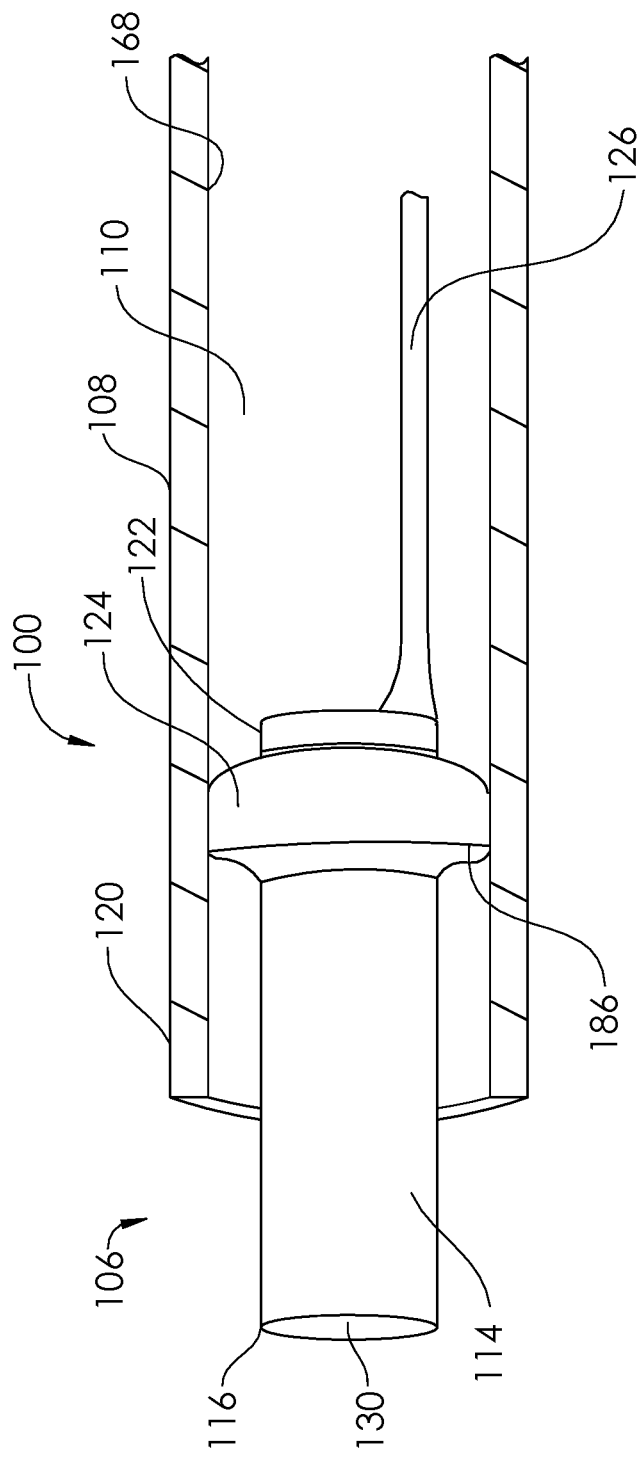
FIG. 19 is a partially sectional view of aspiration system according to an embodiment of the present disclosure.

FIG. 19 illustrates an embodiment of a thrombectomy system 100 having one or more sealing members 124 comprising a hydrogel 186 annularly attached around the outer cylindrical surface 122 of the distal tube 114 of the thrombectomy catheter 106. In some embodiments, the maximum outer diameter of the sealing member 124 comprising a hydrogel 186 may be less than the inner diameter of the inner lumen 110 of the guiding catheter when the hydrogel is in a non-hydrated or substantially non-hydrated state. The maximum outer diameter of the sealing member 124 comprising a hydrogel 186 may become greater than the inner diameter of the inner lumen 110 of the guiding catheter when the hydrogel is in a partially hydrated, substantially hydrated, or fully hydrated state. This feature allows the thrombectomy catheter 106 to be advanced with little drag down the guiding catheter 108 while the sealing member 124 comprising a hydrogel 186 is becoming hydrated. As the sealing member 124 comprising a hydrogel 186 becomes substantially hydrated, the sealing member 124 will likely be already placed at the location of choice in relation to the distal end 120 of the guiding catheter 108. In this position, the larger maximum outer diameter of the sealing member 124 will seal against the inner wall 168 of the inner lumen 110 of the guiding catheter. In some embodiments, the hydrogel 186 has high lubricity in order to allow movement with minimal drag while the sealing member 124 is in sealing relationship against the inner wall 168 of the inner lumen 110 of the guiding catheter. In some embodiments, the high lubricity is achieved by the hydrogel having a higher water holding capacity. In some embodiments, the hydrogel 186 has relatively lower lubricity in order to minimize accidental axial movement of the sealing member 124 in relation to the guiding catheter. In some embodiments, the high lubricity is achieved by the hydrogel having a lower water holding capacity. In some embodiments, the hydrogel comprises p-HEMA.

Figure 20:
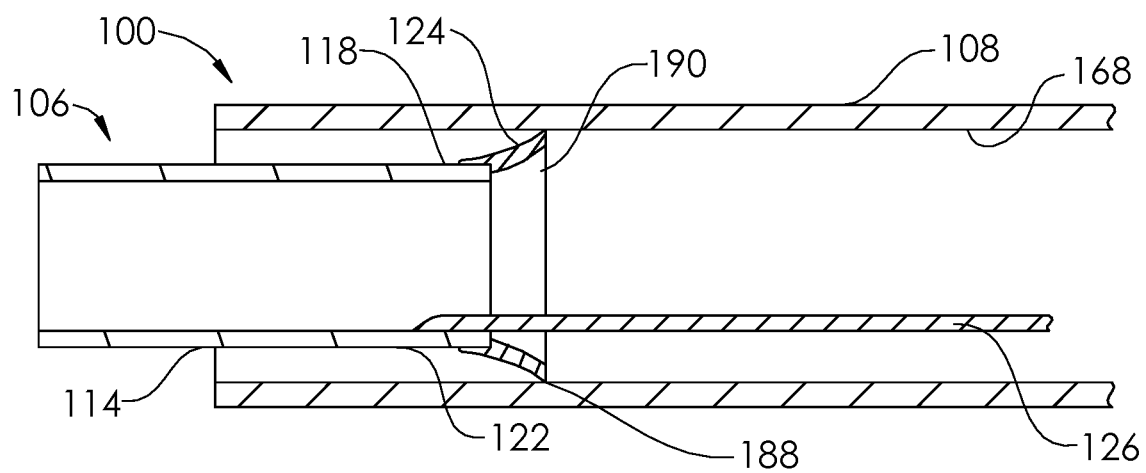
FIG. 20 is a sectional view of an aspiration system according to an embodiment of the present disclosure.

FIG. 20 illustrates an embodiment of a thrombectomy system 100 having one or more sealing members 124 coupled to the proximal end 118 of the distal tube 114 of the thrombectomy catheter 106. In some embodiments, the one or more sealing member 124 is secured to the outer cylindrical surface 122 of the distal tube 114. In some embodiments, the sealing member 124 is a cone-shaped or bowl-shaped membrane 190 configured to seal against the inner wall 168 of the guiding catheter 108 at the wipe end 188.

Figure 21:
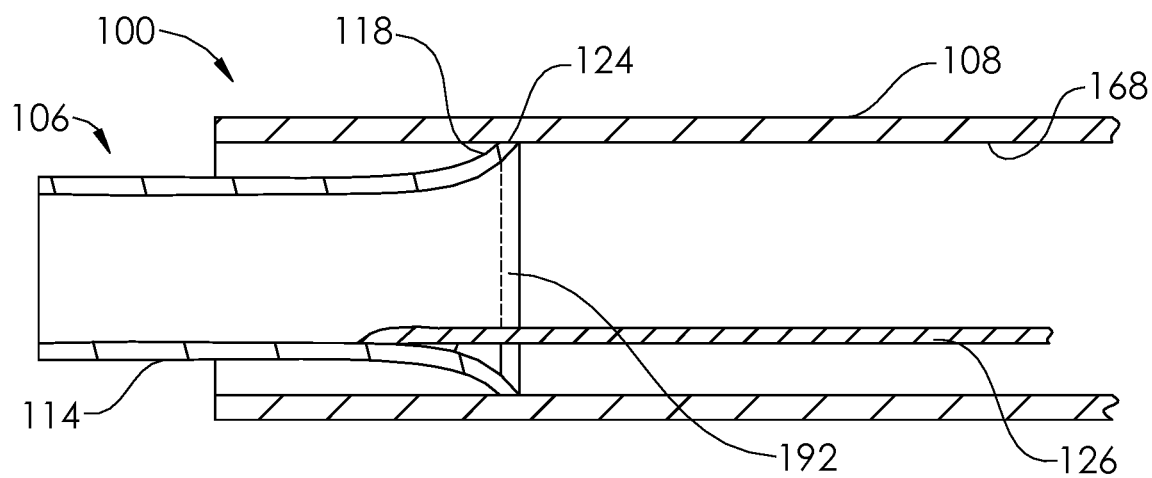
FIG. 21 is a sectional view of an aspiration system according to an embodiment of the present disclosure.

FIG. 21 illustrates an embodiment of a thrombectomy system 100 having a sealing member 124 which is formed from the proximal end 118 of the distal tube 114 of the thrombectomy catheter 106. In some embodiments, the sealing member 124 is formed by flaring the proximal end 118 of the distal tube 114, so that a seal ring 192 is created, for sealing against the inner wall 168 of the guiding catheter 108.

Figure 22:
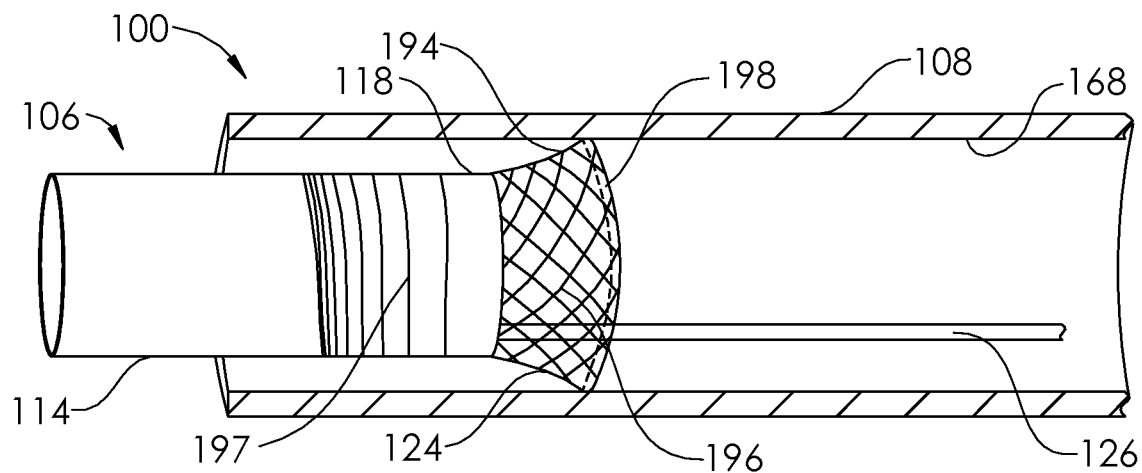
FIG. 22 is a partially sectional view of an aspiration system according to an embodiment of the present disclosure.

FIG. 22 illustrates an embodiment of a thrombectomy system 100 having a sealing member 124 coupled to the proximal end 118 of the distal tube 114 of the thrombectomy catheter 106. In some embodiments, the sealing member 124 may comprise a cone-shaped or bowl-shaped structure 194. In some embodiments, the structure 194 may be formed from a tubular braid 196. In some embodiments, the tubular braid 196 may be braided from metallic wires. In some embodiments, the tubular braid 196 may be braided from Nickel-Titanium wires. In some embodiments, the tubular braid 196 may be heat set into a cone shape or a bowl shape. In some embodiments, the tubular braid 196 may be dip coated. In some embodiments, the tubular braid 196 may be dip coated after having been heat set. In some embodiments, the tubular braid 196 may be dip coated with polyurethane. In some embodiments, the tubular braid 196 may be dip coated with silicone. In some embodiments, the dip coating material may form a seal ring 198 for sealing against the inner wall 168 of the guiding catheter 108. In some embodiments, the tubular braid 196 is formed so that the seal ring 198 is forced against the inner wall 168 of the guiding catheter 108. In some embodiments, the dip-coated, formed tubular braid 196 is sufficiently compressible that it can be pushed through the inner lumen 110 of a guiding catheter 108. FIGS. 20-22 illustrate embodiments of a thrombectomy catheter 106 in a condition when it is at least partially extended axially out of the inner lumen 110 of the guiding catheter 108. In some embodiments, a stiffness transition member 197 (FIG. 22) may be incorporated into the distal tube 114. In some embodiments, the stiffness transition member 197 may comprise a hypo tube that is spiral cut (e.g. laser cut) with decreasing pitch moving distally. Other cut patterns may be used, such as a series of partial circumferential cuts, or a zig-zag cut. A number of other methods known in the art may be used to create a transition in stiffness, such as use of composite materials, a transition of polymeric materials, or transitioning braids or coils.

Figure 23:
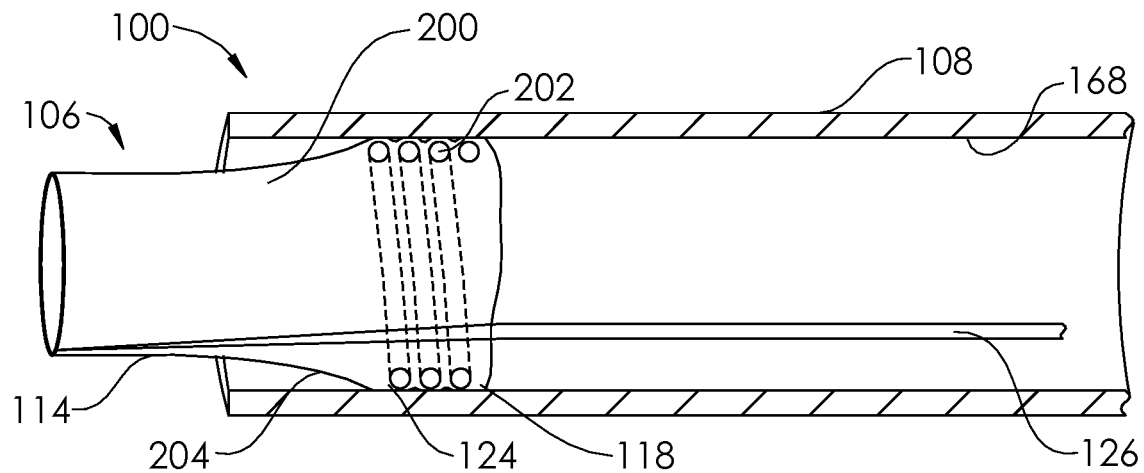
FIG. 23 is a partially sectional view of an aspiration system according to an embodiment of the present disclosure.

FIG. 23 illustrates an embodiment of a thrombectomy system 100 having a sealing member 124 which is the proximal end 118 of the distal tube 114 of the thrombectomy catheter 106. In some embodiments, the entire distal tube 114 comprises a windsock-like-member 200 having a tapered portion 204. The proximal end 118 has an increased diameter and is supported radially by a stent section 202. In some embodiments, the stent section 202 is a coil. In some embodiments, the stent section 202 is a laser machined metal tube. In some embodiments, the stent section 202 is a tubular braid.

Figure 24:
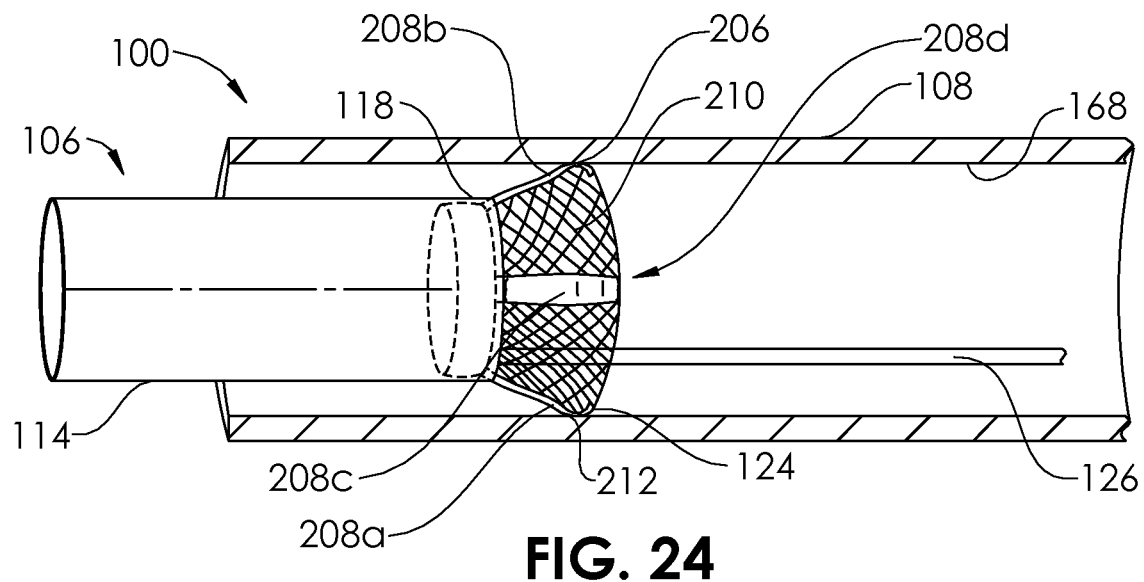
FIG. 24 is a partially sectional view of an aspiration system according to an embodiment of the present disclosure.

FIG. 24 illustrates an embodiment of a thrombectomy system 100 having a sealing member 124 which is coupled to the proximal end 118 of the distal tube 114 of the thrombectomy catheter 106. A structure 206 comprising two or more fingers 208a-d is secured to the proximal end 118 of the distal tube 114. In some embodiments, the structure 206 is welded or secured using other methods to the support member 126. In some embodiments, the structure 206 is flared outwardly towards the proximal end, leading to a sealing ring 212. In some embodiments, the structure 206 includes a covering 210 over the fingers 208a-d. In some embodiments, the covering 210 is a membrane.

FIG. 25 illustrates an embodiment of a thrombectomy system 100 of the present disclosure being used in conjunction with the deployment of a stent 214. In the method for performing this procedure with the thrombectomy system 100, the interventionalist (physician) places a guiding catheter 108 into the blood vessel 102. For example, the interventionalist may place the distal end 120 of the guiding catheter 108 into the ostium of a coronary artery. The interventionalist may next place a guidewire 134 across an atherosclerotic lesion 218, which may or may not have thrombus 104. The interventionalist next tracks an embodiment of the thrombectomy catheter 106 of the present disclosure over the guidewire 134 and through the guiding catheter 108, until the distal end 116 of the distal tube 114 exits the guiding catheter. The interventionalist the tracks the distal end 116 of the distal tube to a target area 112, for example, just proximal to the location of the atherosclerotic lesion 218. The sealing member 124 is positioned within the guiding catheter 108, so that it will be sealingly coupled to the guiding catheter at least while aspiration is being performed. The interventionalist then tracks a dilatation catheter 216 over the guidewire 134, through the guiding catheter 108, and across the atherosclerotic lesion 218. The vacuum source 146 (FIGS. 1 and 2) is coupled to the side port 152 of the y-connector 148, and the stent 214 is expanded by the dilatation balloon of the dilatation catheter 216 while the thrombectomy system performs aspiration. This lowers the possibility that residual thrombus (clot) is carried downstream, causing potential complications. It also lowers then possibility that residual thrombus remains trapped between the stent 214 and the now dilated atherosclerotic lesion 218. When the interventionalist deems the result satisfactory, the interventionalist takes final fluoroscopic (or other) images, and then removes the devices.

FIGS. 26A-26B illustrate an attachment joint 228 and method for joining/coupling the support member 126 to the distal tube of a thrombectomy catheter 106 according to an embodiment of the present disclosure. A tapered half-pipe member 220 comprising a partial cylinder is secured at its large end 222 to the proximal end 118 of the distal tube 114 by adhesive, epoxy, welding, soldering, embedding or other attachment methods. The small end 224 of the tapered half-pipe member 220 is secured to the support member 126 by adhesive, epoxy, welding, soldering, embedding or other attachment methods. Though the skives 158, 160 are not pictured in FIG. 26, they are compatible with this joining embodiment and method. The tapered half-pipe member 220 allows for a gradual transition that provides an open area 226, so that flow is not compromised. In some embodiments, the outer radius 227 of the tapered half pipe member 220 is configured to substantially match the inner diameter of the distal tube 114. In some embodiment, the inner radius 229 of the tapered half pipe member 220 is configured to substantially match the outer diameter of the distal tube 114. These embodiments enable a close fit and thus a relatively low profile.

FIG. 27 illustrates a dipping process for an attachment joint including but not limited to the attachment joint 228 of FIG. 26. After the attachment joint 228 is assembled, a first dipping step 230 is performed over the majority of the length of the distal tube 114. In some embodiments, the distal tube 114 may comprise a lubricious inner tube layer, such as PTFE, and a spring coil inner layer around the PTFE inner tube layer. In some embodiments, a medium durometer dipping material, such as polyurethane or PEBAX, is applied to the distal tube. In some embodiments, the medium durometer material may have a durometer of about 63D. A second dipping step 232 is performed with a low durometer material, such as polyurethane of PEBAX, to form a "Soft" tip 234. In some embodiments, the low durometer material may have a durometer of about 55D. A third dipping step 236 is performed with a high durometer material over the attachment joint 228. In some embodiments, the third dipping step 236 is performed over most or all of the length of the support member 126. In some embodiments, the high durometer material may have a durometer of about 72D. The result is a stiff, pushable catheter 106 that has a smooth transition at the attachment joint 228, a flexible distal tube 114 for tracking through the blood vessel 102 (FIGS. 1, 2 and 25) and a soft tip 234 for atraumatic characteristics within the blood vessel 102. A maximized lumen 130 cross-section area may be achieved in any of the embodiments resented herein by minimizing wall thickness and/or minimizing the thickness of any coating. Ultra-thin wall hypo tubes or polyimide tubes may be used in some embodiments. A dip coating of less than about 0.005 cm (0.002 inches) may be applied, and may include polyurethane. A dip coating of less than about 0.0025 cm (0.001 inches), or about 0.0018 cm (0.0007 inches) may be applied, and may include polyurethane.

FIG. 28 illustrates an embodiment of a thrombectomy catheter 106 of the thrombectomy system 100 having a sealing member 124 that is radially compressed over a compressible section 242 of the distal tube 114 during delivery through the guiding catheter 108 (FIG. 1). The compressible section 242 is held in a compressed state by a delivery sheath 238. In some embodiments, the delivery sheath 238 has a sheath push and pull rod 240 coupled to a portion thereof. In use, the thrombectomy catheter 106 is delivered through the guiding catheter 102 and into the blood vessel 102 by pushing the support member 126 and/or the sheath push and pull rod 240. When the distal end 116 of the distal tube 114 of the thrombectomy catheter 106 is located adjacent the target area 112 and the proximal end 118 of the distal tube 114 is within the inner lumen 110 of the guiding catheter 108 (FIG. 2), traction (tension) is applied on the sheath push and pull rod 240 while compression is applied on the support member 126, thus causing the delivery sheath 238 to be pulled proximally, and removed from the compressible section 242 of the distal tube 114, thus allowing the compressible section 242 to expand, and seal against the inner wall 168 (FIG. 15A) of the guiding catheter 108. In some embodiments, the delivery sheath 238 may be retracted completely and removed completely from the guiding catheter 108. Though a guidewire 134 is not depicted in FIG. 28, this embodiment, like the other embodiments, may be used with a guidewire 134, as known in the art. In some embodiments, the support member 126 may be coupled to the distal tube 114 via a ring 244. In some embodiments, the ring 244 may be closer to the distal end 116 of the distal tube 114 than the proximal end 118.

Saline Injection Aspiration

Figure 29:
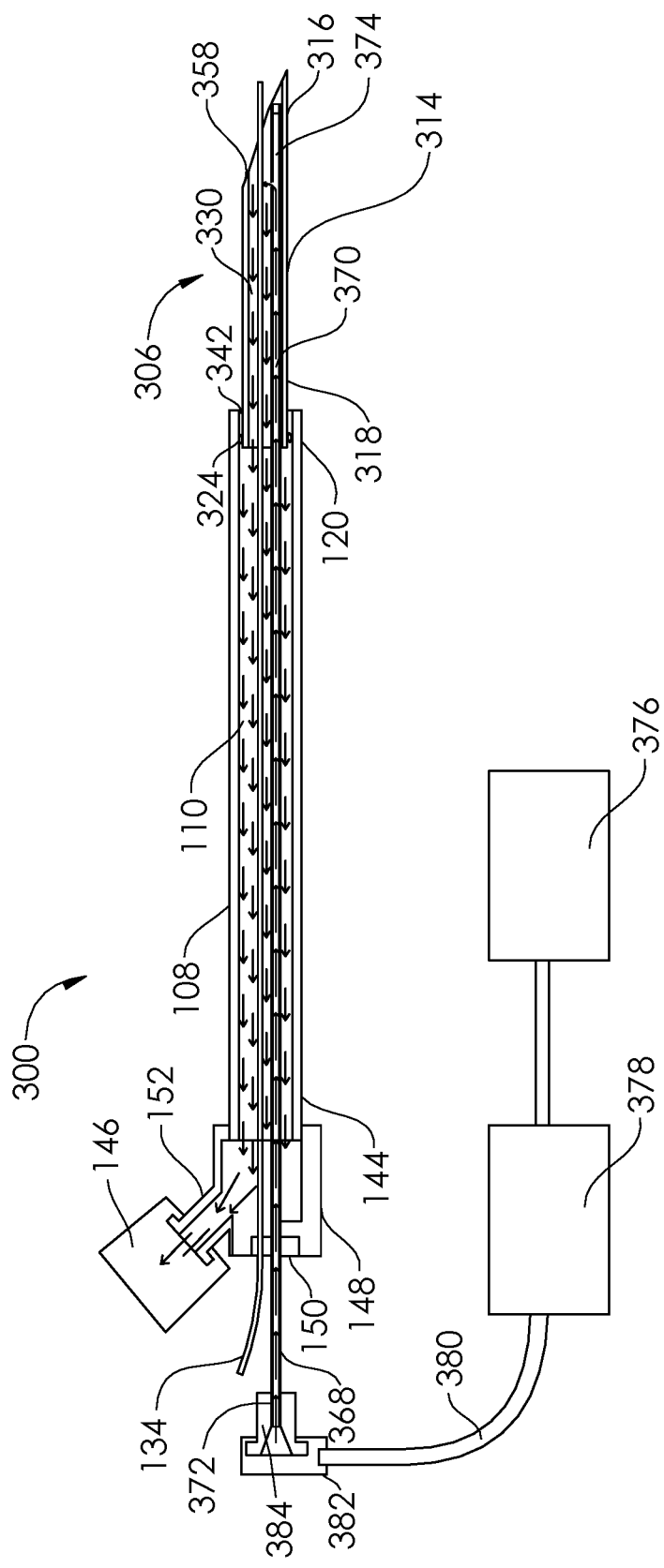
FIG. 29 is a sectional view of an embodiment of a saline injection aspiration (thrombectomy) catheter according to an embodiment of the present disclosure, with a guidewire in place through the lumens.

FIG. 29 illustrates a thrombectomy system 300 which incorporates the high pressure injection of a liquid, for example sterile saline solution, in order to macerate and aspirate thrombus 104 (FIG. 1). A guiding catheter 108 and a y-connector 148 having a proximal seal 150 and a sideport 152 are coupled to a vacuum source 146, as described in relation to the prior embodiments. A thrombectomy catheter 306 comprises a distal tube 314 having a distal end 316 and a proximal end 318, the proximal end 318 incorporating one or more sealing members 324 for sealing off an annulus 342 between the guiding catheter 108 and the distal tube 114, as described in relation to the prior embodiments. The distal tube 314 has an aspiration lumen 330. A support/supply tube 368, having a lumen 370, is coupled to the distal tube 314. The support/supply tube 368 serves the same purpose as the support member 126 of the prior embodiments, but is also a conduit (via the lumen 370) for high pressure saline, which is injected from the proximal end 372 to the distal end 374. The saline is supplied from a saline source 376 (e.g. saline bag, bottle) and pressurized by a pump 378, through a supply tube 380 and through a luer connector 382 which is connected to a luer hub 384 coupled to the support/supply tube 368. In some embodiments, the support/supply tube 368 comprises a hypo tube. In some embodiments, the support/supply tube 368 comprises stainless steel or nitinol.

Figure 30:
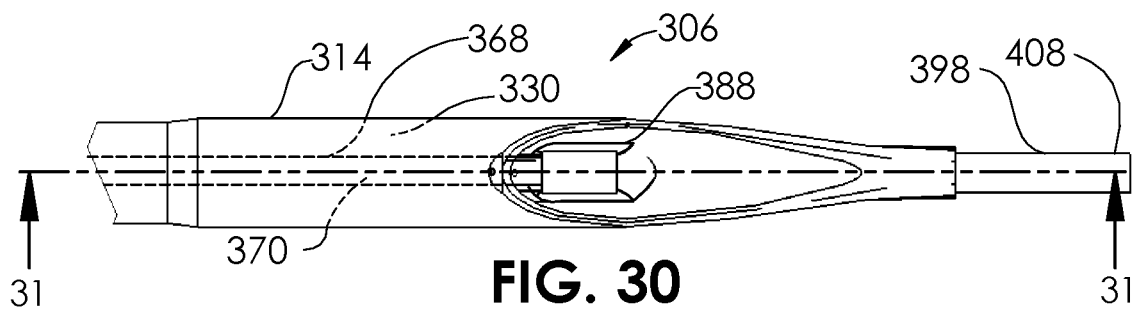
FIG. 30 is a plan view of a distal end of an alternative embodiment of the saline injection aspiration (thrombectomy) catheter of FIG. 29.
Figure 31:
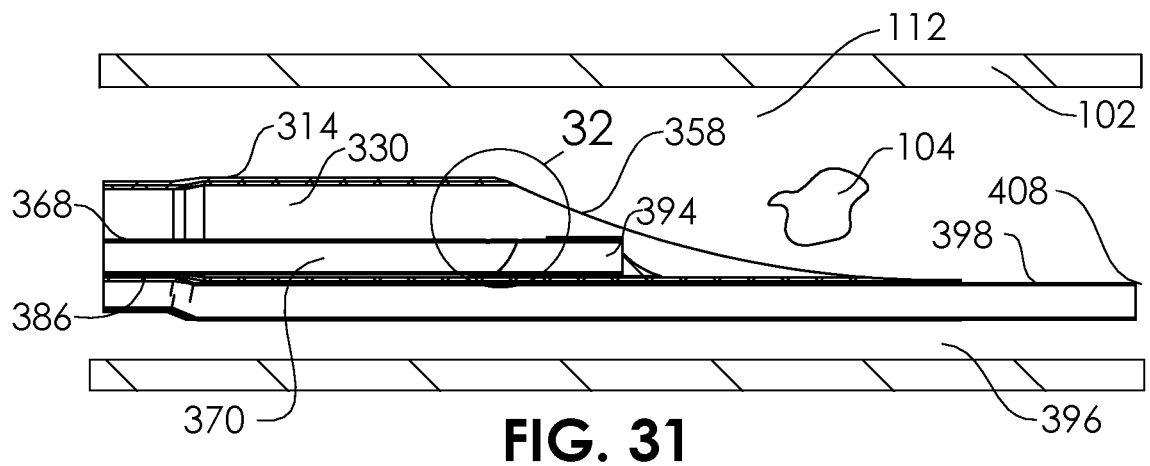
FIG. 31 is a sectional view of the saline injection aspiration (thrombectomy) catheter of FIG. 30, taken along the line 31-31.
Figure 32:
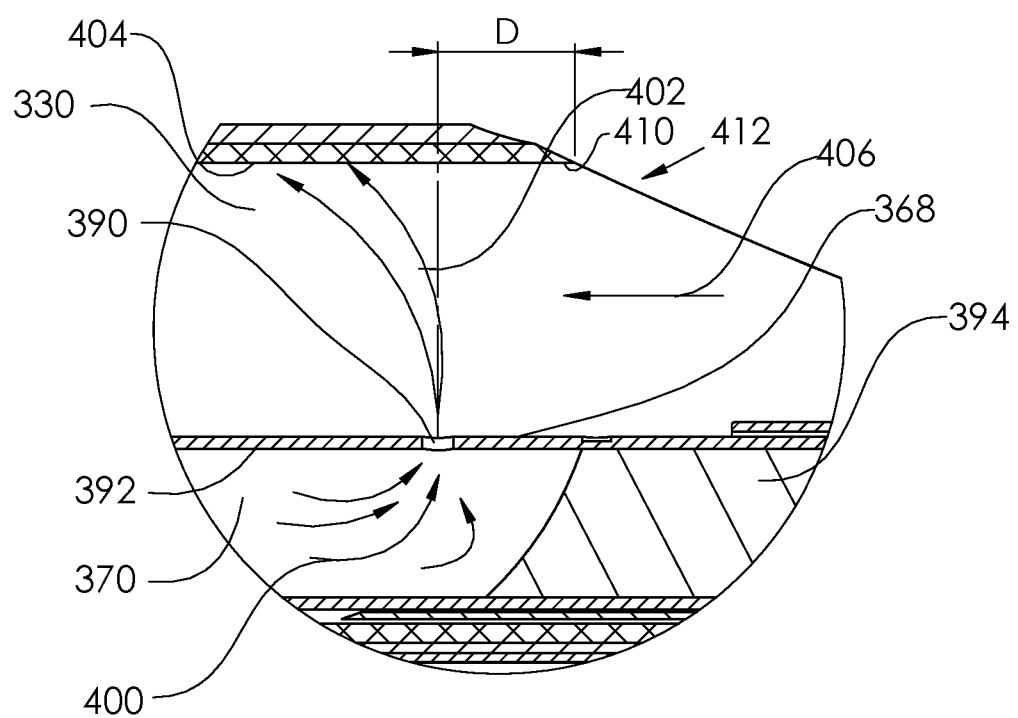
FIG. 32 is a detail view of the saline injection aspiration (thrombectomy) catheter of FIG. 31 within circle 32.

Turning to FIGS. 30-32, in some embodiments, the support/supply tube 368 may be coupled to the distal tube 314 by attachment materials 386, 388, including adhesive, epoxy, or melted/molded polymer materials. In some embodiments, the support/supply tube 368 has a closed distal end 394, and has one or more orifices 390 in its wall 392. In some embodiments, a rapid exchange tube 398 having a guidewire lumen 396 and a distal tip 408 may be coupled to the side of the distal tube 314, as seen in FIGS. 30 and 31, although the embodiment of FIG. 29 is shown with the guidewire 134 extending through the aspiration lumen 330 and the inner lumen 110.

After the user tracks the thrombectomy catheter 306 through the guiding catheter 108 and to the target area 112 in the blood vessel 102, the pump 378 is operated to inject high pressure saline through the support/supply tube 368. When the saline reaches the orifice (arrows 400), the saline is forced through the one or more orifices 390 and into the aspiration lumen 330. In some embodiments, the saline forms one or more jets 402 that impinge upon in inner wall 404 of the aspiration lumen 330, adjacent the one or more orifices 390. A high pressure is thus created in the aspiration lumen 330 adjacent the skive 358, forcing thrombus 104 into the aspiration lumen 330 in a direction generally shown by arrow 406. The thrombus 104 is then carried by the positive pressure gradient from distal to proximal from the aspiration lumen 330 into the inner lumen 110 of the guiding catheter 108 and out the sideport 152 of the y-connector 148 towards the vacuum source 146. In some embodiments, the one or more jets 402 serve to break up and macerate the thrombus 104, aiding in its subsequent passage through the lumens 330, 110. The mixing of the saline with the broken up thrombus 104 serves to lower its bulk viscosity, and thus aid in its passage through the catheter lumens with less resistance. In some embodiments, the one or more orifices 390 are located a distance D from the most proximal portion 410 of a distal opening 412 formed in the aspiration lumen 330 by the skive 358. In some embodiments, the distance D between the axial center of an orifice 390 and the most proximal portion 410 of the distal opening 412 is about 0.0508 cm (0.020 inches), or in some embodiments is 0.0508 cm±0.0076 cm (0.020 inches±0.003 inches).

FIGS. 33-34B illustrate an alternative embodiment of the support/supply tube 368, wherein the support/supply tube 368 couples to the distal tube 314 at the proximal end 318 of the distal tube 314. The distal tube 314 includes a wall 416 having a lumen 414. The support/supply tube 368 is coupled to the lumen 414 so that saline supplied through the support/supply tube 368 then passes through the lumen 414 distally, and exits the one or more orifices 390. In some embodiments, the lumen 414 may be provided by a separate polyimide tube that is embedded in the wall 416. In some embodiments, a proximally facing lip 246, for example, an annular seal extending in both a radial and proximal direction, is sealingly coupled to the distal tube 314. The high pressure saline injection through the lumen 370 of the support/supply tube 368, in combination with the vacuum source 146 (FIGS. 3-6), causes aspiration in a direction generally shown by arrow 406. The high pressure saline injection also creates an internal pressure $P_1$ within the inner lumen 110 of the guiding catheter 108 that is higher than the ambient pressure PA outside the distal end 120 of the guiding catheter 108. Because $P_1$>PA, the proximally facing lip 246 is forced against the inner wall 168 of the inner lumen 110 of the guiding catheter 108, sealing the annulus 142. In some embodiments, the proximally facing lip 246 is thin and made from a flexible material (as in the distally facing lip 166 of FIG. 11), thus aiding is ability to be forced against the inner wall 168. In some embodiments, other embodiments of the sealing member 124 may be used, including, but not limited to, o-rings and hydrogel seals. In some embodiments, as seen in FIG. 34B, the distal end of the support/supply tube 368 may have an oval, elliptical or rectangular shape in order to allow a connection to the lumen 414 of the distal tube 314 that does not significantly compromise the size of the aspiration lumen 330 of the distal tube 314.

Figure 71:
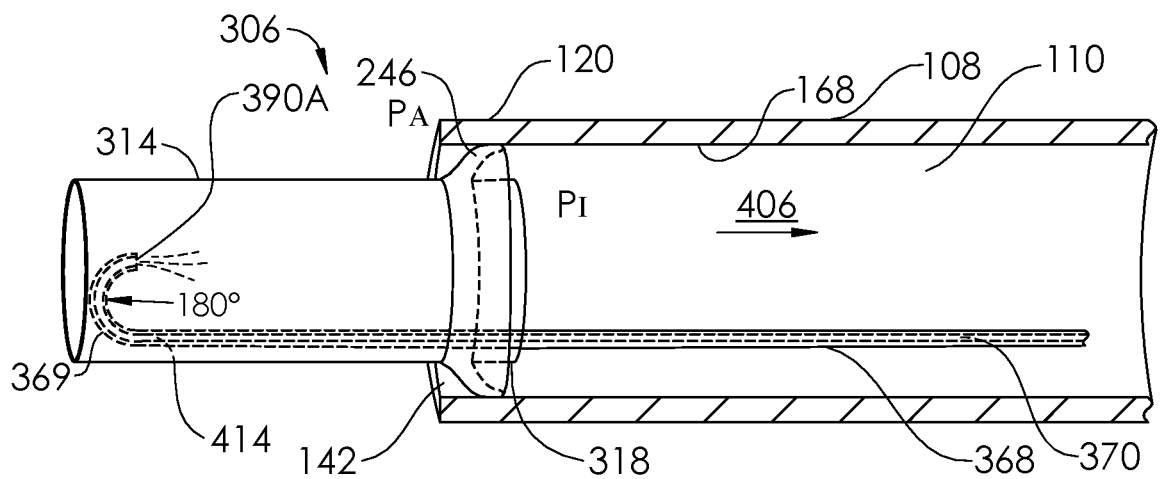
FIG. 71 is an alternative embodiment of the aspiration catheter of FIG. 33.
Figure 72:
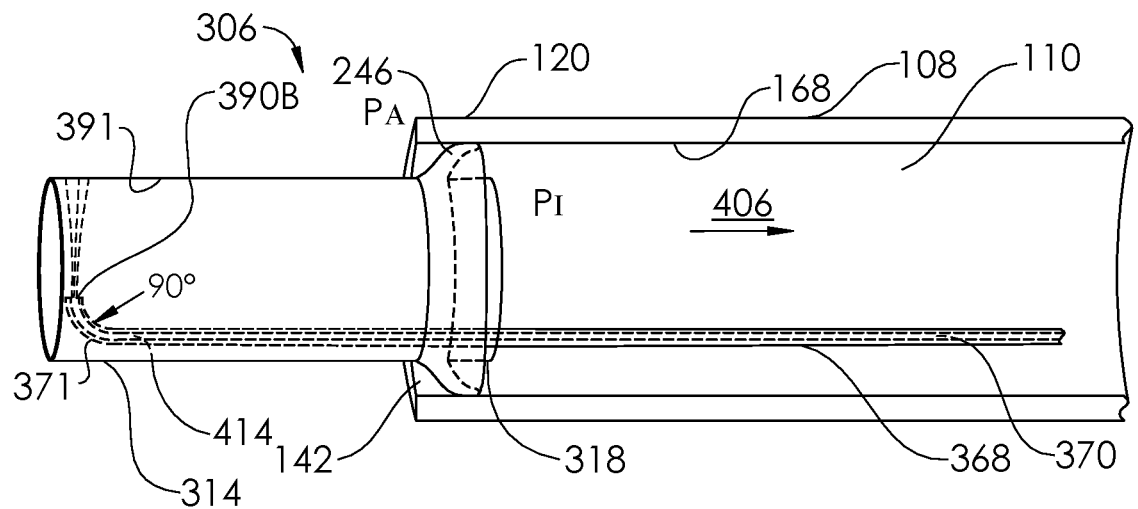
FIG. 72 is an alternate embodiment of the aspiration catheter of FIG. 33.
Figure 73:
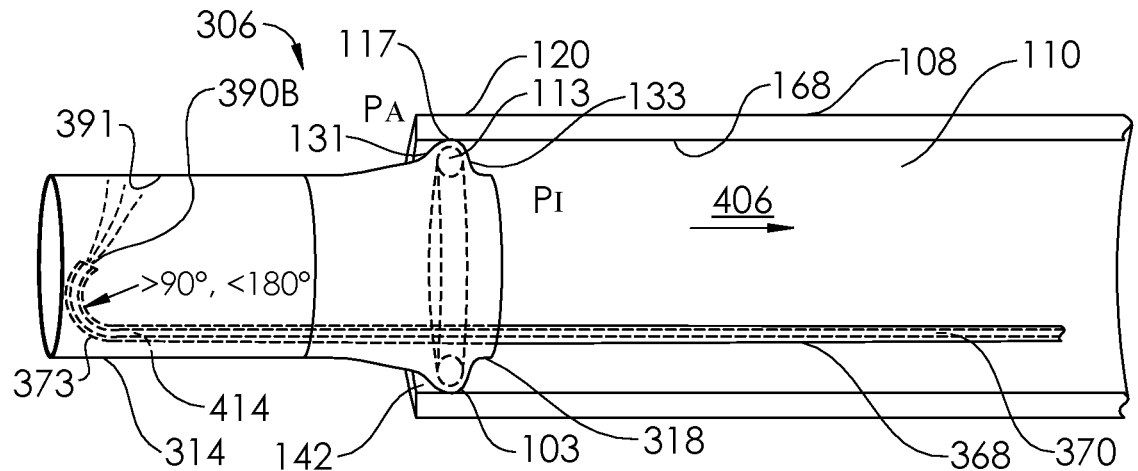
FIG. 73 is an alternate embodiment of the aspiration catheter of FIG. 33.

FIG. 71 is an alternate embodiment of a thrombectomy catheter 306 with the support/supply tube 368 of FIG. 33 having a full distal curve 369 that reverses itself, such that the orifice 390A causes fluid to exit in a reverse direction. In some cases, the full distal curve may be approximately 180°. The full distal curve 369 is a continuous curve that gradually changes the direction of fluid that is flowing through the lumen 370 of the support/supply tube 368. "Direction of fluid" is defined as the direction that the majority of the fluid generally travels. In some embodiments, the reverse direction of exit is along the longitudinal axis in a proximal direction, as generally shown in FIG. 71. The saline ejected from the orifice 390A may push and lubricate thrombus that is sucked into the distal tube 314, thus maintaining continued aspiration. FIG. 72 is an alternate embodiment of the support/supply tube 368 of FIG. 33 having an approximately 90° curve 371 that has an orifice 390B pointing towards the inner wall 391 of the distal tube 314. In a further alternate embodiment illustrated in FIG. 73, a curve 373 in the support/supply tube 368 is between about 90° and about 180°. In actuality, an angle anywhere between 90° and 180°, even including 90° or 180°, may be chosen. The angle of the particular curve 373 in FIG. 73 is between 120° and 150°, or about 135°. The saline ejected from the orifice 390B may macerate the thrombus against the inner wall 391 of the distal tube 314, thus maintaining continued aspiration. In some embodiments, the orifice 390A, 390B may have an inner diameter of less than about 0.02 cm (0.008 inches), or about 0.0075 cm (0.003 inches) to about 0.01 cm (0.004 inches). In some embodiments the curve 369, 371 may span about one centimeter or about one centimeter or less of longitudinal catheter length. The proximally facing lip 246, shown in the embodiments of FIGS. 71 and 72, may be replaced by other annular seals disclosed herein. For example, the proximally facing lip 246 in the embodiments of FIGS. 71 and 72 may be replaced by the annual seal 103 of FIGS. 16-17. For example, FIG. 73 illustrates an annular seal 103 comprising an o-ring 113 and having an elastomeric coating 117. The elastomeric coating 117 covering the o-ring 113 forms a first diametric transition 131 and a second diametric transition 133.

Figure 35:
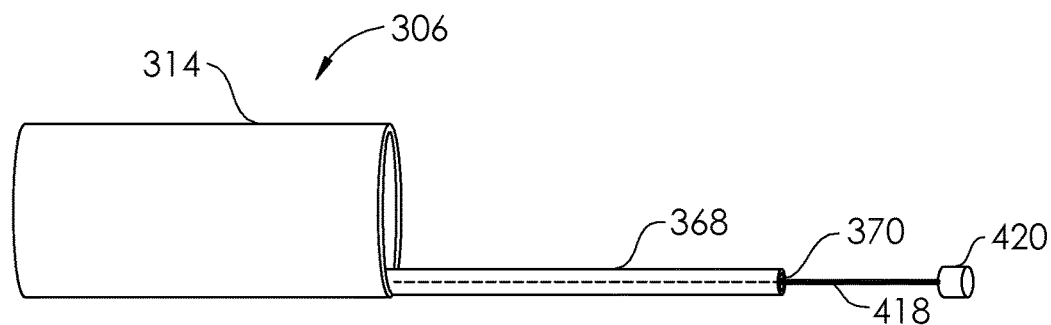
FIG. 35 is a perspective view of a proximal section of a saline aspiration (thrombectomy) catheter according to an embodiment of the present disclosure.

FIG. 35 illustrates an embodiment of the thrombectomy catheter 306 wherein the lumen 370 of the support/supply tube 368 may be decoupled from the luer hub 384 (FIG. 29) so that a stylet 418 may be inserted down the lumen 370 in order to impart additional stiffness and pushability. In some embodiments, the stylet 418 comprises stainless steel. In some embodiments, the support/supply tube 368 is a circular cross-section hypo tube and has an outer diameter of about 0.0549 cm (0.0216 inches) and an inner diameter of about 0.0483 cm (0.019 inches). In some embodiments, the stylet 418 has a circular cross-section and has an outer diameter of between about 0.038 cm (0.015 inches) and about 0.0457 cm (0.018 inches). In some embodiments, the stylet 418 may have a hub 420 at its proximal end, in order to aid handling of the stylet 418 during insertion and removal.

Figure 36:
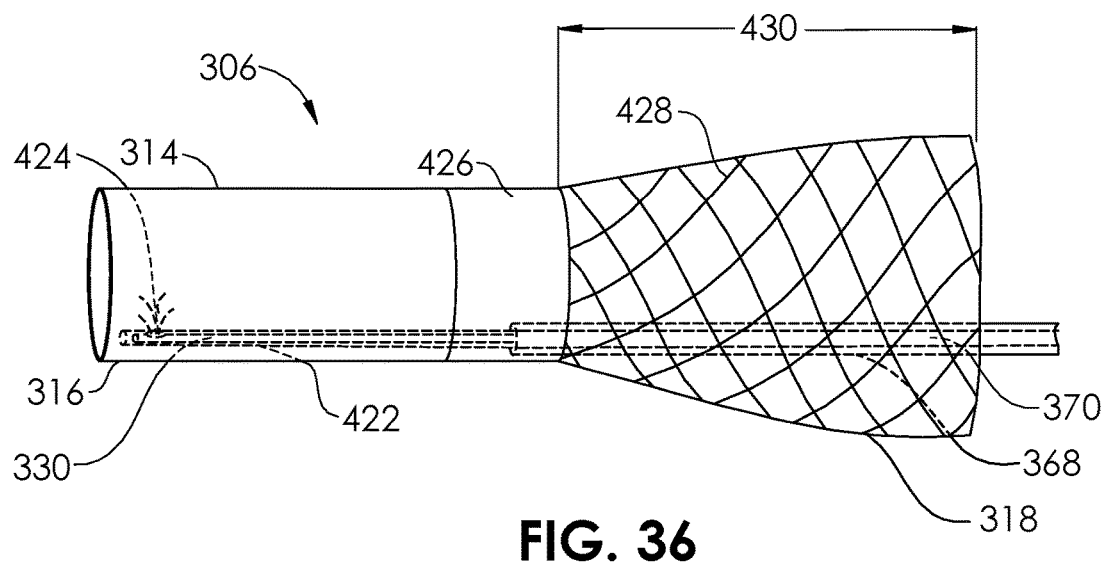
FIG. 36 is a perspective view of a distal section of a saline aspiration (thrombectomy) catheter according to an embodiment of the present disclosure.

FIG. 36 illustrates an embodiment of the thrombectomy catheter 306 wherein the lumen 370 of the support/supply tube 368 is coupled to a smaller tube 422 within the aspiration lumen 330 of the distal tube 314. In some embodiments, the smaller tube 422 is a polyimide tube. In some embodiments, the smaller tube 422 is a tapered polyimide tube, tapering to a smaller diameter as it extends distally to its orifice 424. The support/supply tube 368 is also secured to a ring 426, which in some embodiments is closer to the distal end 316 than the proximal end 318 of the distal tube 314. The ring 426 is also secured to the distal tube 314. When the user pushes on the support/supply tube 368 at its proximal end, the force that in turn is applied to the ring 426 serves to "pull" the proximal end 318 of the distal tube 314, thus lessening the chances of compressing or deforming it. The proximal end 318 of the distal tube 314 includes an expandable section 430 which may include a tubular mesh 428. The tubular mesh 428 may be encapsulated, for example by dipping in polyurethane of silicone, in order to create a sealed aspiration lumen 330 that exends from the distal end 316 to the proximal end 318. In some embodiments, the ring 426 may be constructed from a metal material, such as stainless steel or nitinol. In some embodiments, the ring 426 may include radiopaque material, such as platinum, for visualization on fluoroscopy or x-ray. The ring 426, and its use as the point of application of pushing or pulling, may be incorporated into one of the embodiments of the thrombectomy catheters 106 that do not have high pressure saline injection, but only aspiration. In this case, the support/supply tube 368 need not be a tube or hypo tube, but may also be a solid round wire flat wire.

Because of their use of the inner lumen 110 of the guiding catheter 108 as a portion of the extended lumen 128 (FIG. 2), any of the thrombectomy systems 100, 300 presented include the feature that one length (model) the thrombectomy catheter 106, 306 may be used on a variety of patient sizes and/or target area 112 depths. A single model of thrombectomy catheter 106, 306 may be adjusted to the desired depth in the blood vessel 102 so that it is adjacent to the target area 112, but the vacuum source 146 is still coupled at the same location, on the side port 152 of the y-connector 148. A large range of models (e.g. different lengths) of the thrombectomy catheter 106, 306 is not required. In some cases, this may mean that a single model of thrombectomy catheter 106 and/or a single model of thrombectomy catheter 306 may satisfy the majority of thrombectomy procedures performed in a particular catheterization laboratory or other health care facility, thus requiring a smaller area of shelf space.

Figure 38:
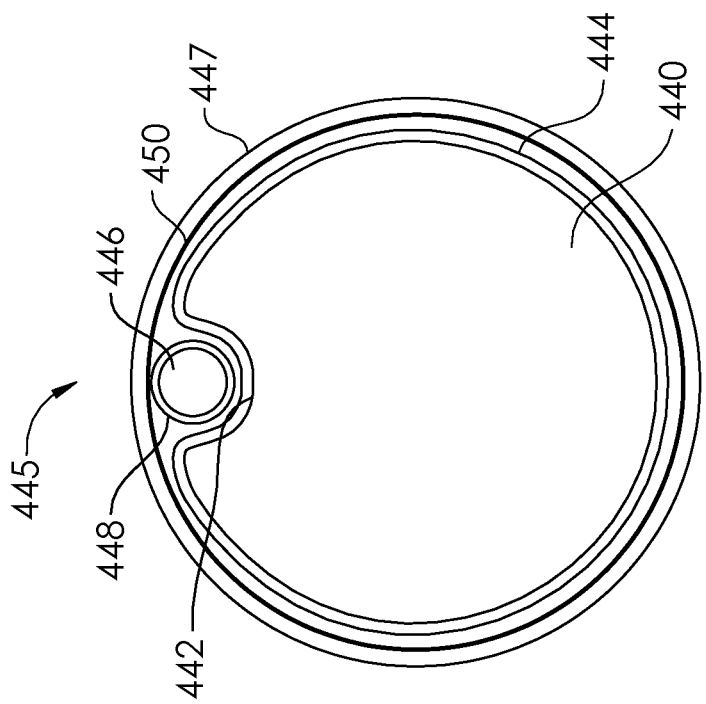
FIG. 38 is a cross-sectional view of the slotted mandrel of FIG. 37 as used in a dipping process according to an embodiment of the present disclosure.
Figure 37:
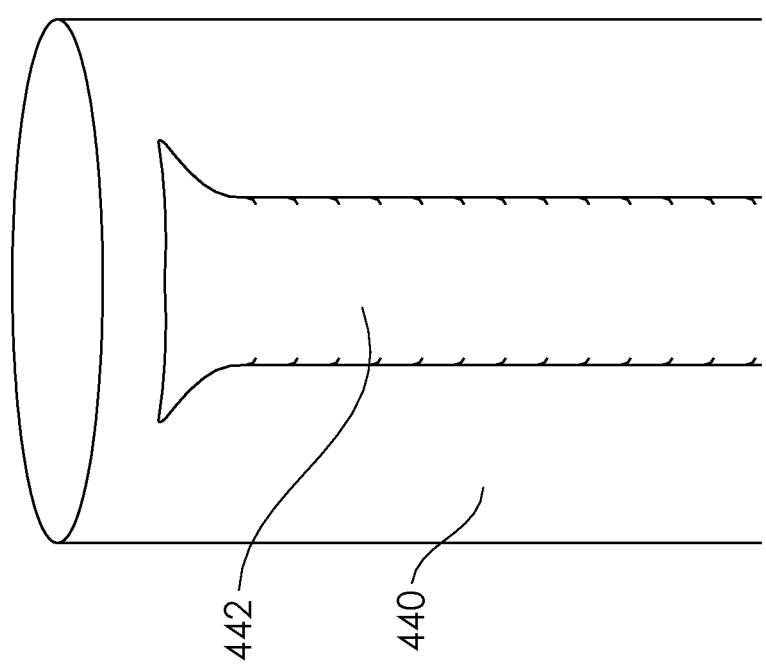
FIG. 37 is a perspective view of a slotted mandrel according to an embodiment of the present disclosure.

An assembly process for an embodiment of a thrombectomy catheter 306 is illustrated in FIGS. 37-42. A slotted mandrel 440 having a longitudinally extending slot 442 is shown in FIG. 37. FIG. 38 illustrates a cross-section of the slotted mandrel 440 and several components placed over it during a placement step, in the following radial order: liner tube 444, saline lumen tube 448 having a saline lumen 446, and a support layer 450. In some embodiments, the orifice may be pre-cut into the saline lumen tube 448 and may be aligned during the placement step. In some embodiments, the liner tube 444 may comprise PTFE or other fluropolymers. In some embodiments, the saline lumen tube 448 may comprise a polyimide tube. In some embodiments, the support layer 450 may comprise a tubular braid, one or more coils or a laser machined hypo tube. The slotted mandrel 440 with the components 444, 448, 450 placed over it, is dipped into a polyurethane, silicone, or other material to coat and set, during a dipping process, creating a composite structure 445 having an outer layer 447. The slotted mandrel 440 is then removed, during a removal step, and the ends of the saline lumen tube 448 may be cut clean. As seen in FIGS. 39-42, a radiopaque marker band 452 may be incorporated as part of the assembly by bonding the radiopaque marker band 452 to the saline lumen tube 448 with an adhesive 454 or epoxy, aligning the saline lumen tube 448 as in FIG. 42, and then completing the assembly and the dipping process as described in relation to FIG. 38.

Clog Detection/Clot Detection

Clogging of aspiration catheters, for example by large pieces of thrombus, is a common concern for users. Techniques to avoid clogging/choking of material within the catheter often involve rapidly, aggressively advancing the aspiration catheter or gently plucking at edges of a thrombus to insure only small pieces or portions are introduced at a time, pieces which are small enough to not clog or occlude the aspiration lumen. When a device becomes clogged during use, the potential for inadvertent dislodgment of thrombus downstream increases; this is referred to as distal embolism. As aspiration procedures of this type are often used in highly technical emergent settings, early clog detection of the aspiration catheter for the user during aspiration can contribute to the success of the procedure and clinical outcome. Some sources have reported that up to 50% of aspiration catheters used get clogged during use.

The user may have difficulty determining whether there is a vacuum in the system or not. For example, the user may have difficulty determining whether the vacuum has been applied or not (e.g., the vacuum source has been turned on or off). Additionally, the user may have difficulty determining whether there has been a loss of vacuum in the system, for example because of the syringe (or other vacuum source) being full of fluid or because of a leak in the system. Blood is relatively opaque and can coat the wall of the syringe, thus making it difficult to determine when the syringe becomes full. This makes it difficult to determine whether sufficient vacuum is being applied to the aspiration catheter. The vacuum level may change to an unacceptable level even before the syringe becomes full. Extension tubing or other tubing may also cause a loss in vacuum in the system. Certain tubing kinks may be difficult for a user to see or identify. It is also difficult to determine whether there is an air leak in the system, which can be another cause for a loss of vacuum even before the syringe becomes full of the aspirated fluid.

During the aspiration of thrombus with an aspiration catheter, it is difficult to identify when thrombus is actively being aspirated or when only blood is being aspirated. Typically, it is desired to not aspirate sizable quantities of normal blood from blood vessels, because of the importance of maintaining normal blood volume and blood pressure. However, when tracking the tip of an aspiration catheter in proximity to a thrombus, it is difficult to know whether the aspiration catheter has actively engaged a thrombus, whether it has aspirated at least a portion of the thrombus, or whether it is not engaged with the thrombus, and is only aspirating blood. Though some aspiration catheters, such as those used in the peripheral blood vessels or in an arteriovenous fistula, may be around 50 cm or even less, the tip of an aspiration catheter may in same cases be more than 90 cm from the hands of the user, or as much as 135 cm from the hands of the user, or in some cases as much as 150 cm, and the particular status of vacuum at the tip of the catheter is often not known by the user. A user may thus be essentially plunging a catheter blindly without significant, usable sensory feedback. The catheter may have an outer diameter up to or even greater than 6 French, and may be as high as 10 French or greater. The increased catheter outer diameter can cause some concern of potential trauma inside a blood vessel. The use of aspiration catheters can therefore be inefficient, and cause more blood removal than desired, causing a user to minimize the length of the therapy and in severe cases necessitating blood transfusion. An increased volume of normal blood being aspirated also means that the vacuum source (e.g. syringe) will fill in a shorter amount of time, thus required more frequent replacement of the vacuum source. Distal embolism may occur if the vacuum pressure is not sufficient, and yet the user is not aware.

In some cases, a syringe that is completely or mostly full or blood and/or thrombus may continue to be used, though in this state, there is not sufficient pressure to effectively aspirate thrombus or unwanted material, thus causing inefficient use of time, and lengthening the procedure. In some cases, the user may not realize the plunger of the syringe has mistakenly not been pulled back (to evacuate the syringe). In some cases, the syringe itself may be defective, and a proper vacuum may not be achieved, without the user being aware. In some cases, kinked tubing, lines, or catheters may go unnoticed, because of bad visibility in a procedural laboratory, or simply from the extent of concurrent activities being performed. In many cases, the user's eyes are oriented or focused on a monitor, for example a fluoroscopic monitor or other imaging monitor, or a monitor with patient vital data. Though the user may be able to view flow through transparent or partially transparent lumens (such as extension tubing), in dim lighting with intermittent viewing, it is difficult for the user's mind to process flow of an opaque liquid (such as blood/thrombus). Even in good lighting with a focused eye, the movement of fluid through extension tubing may not present an accurate picture of the aspiration status, as the visual flow effect may be delayed in relation to the applied vacuum. More than one medical device personnel may be sharing sensory information with each other to attempt to build a current status in each other's minds of the aspiration procedure. When a user relies on another's interpretation, especially when either are multitasking, a false sense of the status may occur. A syringe attached to the aspiration catheter may cause kinking, for example, if placed on an uneven surface. The distal opening in an aspiration lumen of an aspiration catheter may be prone to aspirating directly against the wall of a blood vessel, thus being temporarily stuck against the vessel wall, and stopping flow throughout the aspiration lumen. In some cases, a vacuum that is too large may be accidentally or inappropriately applied to the aspiration lumen of the aspiration catheter, limiting effectiveness (for example, if it causes the walls surrounding the aspiration lumen to collapse and thus, cut off the significantly decrease the flow through the aspiration lumen). The syringes which are sometimes used as a vacuum source to connect to an aspiration lumen of an aspiration catheter may malfunction, and not be fully actuated/evacuated. But, even when the syringe is functioning correctly, it will tend to fill up at difficult to predict moments, and thus commonly have periods of no applied vacuum. In the cases wherein a portion of clot/thrombus is being aspirated through the aspiration lumen, a significant pressure drop may occur at the current position of the thrombus, and thus, a sufficient vacuum may only exist from the proximal end of the aspiration lumen and distally up to the point of the thrombus. Thus, an insufficient vacuum may exist at the distal end of the aspiration lumen, e.g., at the distal end of the aspiration catheter. The same situation may occur if there is an actual clog at some intermediate point within the aspiration lumen. In either of these conditions, because of the insufficient vacuum at the distal end of the aspiration lumen, there may be a risk of thrombus or emboli being send distally in the vasculature, which may cause occlusion, stroke, pulmonary embolism, or other disorders, depending upon the location of the intervention. With current apparati and techniques, these situations are very difficult to detect when they occur. It has been estimated that in as many as 50% of thrombus aspiration procedures, some sort of failure occurs.

Figure 43:
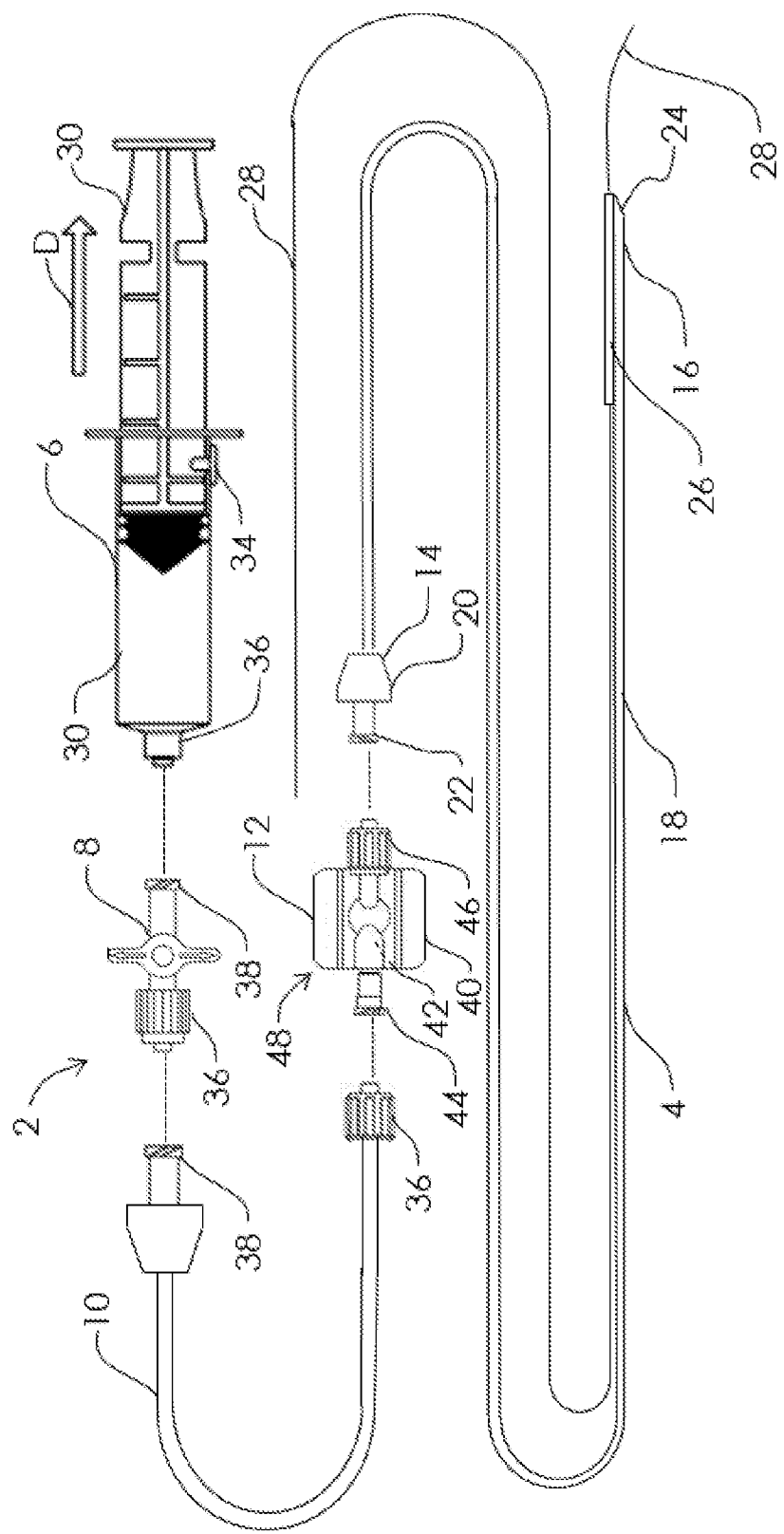
FIG. 43 is a plan view of a system for aspiration according to an embodiment of the present disclosure.

An aspiration system 2 is illustrated in FIG. 43 and is configured to allow real time monitoring of catheter aspiration. The aspiration system 2 comprises an aspiration catheter 4, a vacuum source 6, a valve 8, extension tubing 10, and an aspiration monitoring system 48 including an in-line pressure transducer 12. The aspiration catheter 4 has a proximal end 14 and a distal end 16 and an aspiration lumen 18 extending from the proximal end 14 to the distal end 16. The aspiration lumen 18 may be sized for aspiration of thrombus, and in some embodiments may have an inner diameter of between about 0.38 millimeter (0.015 inches) and about 2.54 millimeters (0.100 inches). The aspiration catheter 4 includes a hub 20 at its proximal end which may include a female luer connector 22. The aspiration lumen 18 at the distal end 16 of the aspiration catheter 4 may include an angled orifice 24, which aids in the tracking through tortuous or occluded vasculature. In some embodiments, a guidewire lumen 26 is coupled to the distal end 16 of the aspiration catheter 4, and is configured to track over a guidewire 28. The vacuum source 6 may comprise a syringe, and may be sized between 5 ml and 100 ml, or between 20 ml and 60. The vacuum source 6 may comprise a VacLok® syringe, made by Merit Medical, South Jordan, Utah. The vacuum source 6 may include a barrel 30 and plunger 32, with a lock 34 which is configured to retain the plunger 32 in position in relation to the barrel 30, for example, when the plunger 32 is pulled back in direction D to create a negative pressure (vacuum) inside the barrel 30. In some embodiments, the vacuum source 6 may comprise any other type of evacuatable reservoir, or may comprise a vacuum pump. The vacuum source 6 is connected to the aspiration lumen 18 of the aspiration catheter 4 via the extension tubing 10 and the valve 8. In some embodiments, the vacuum source 6 may be connected directly to the aspiration lumen 18 of the aspiration catheter 4. Male luer connectors 36 and female luer connectors 38 are indicated in FIG. 43. The valve 8 may be a standard two-way stopcock, as illustrated.

Figure 44A:
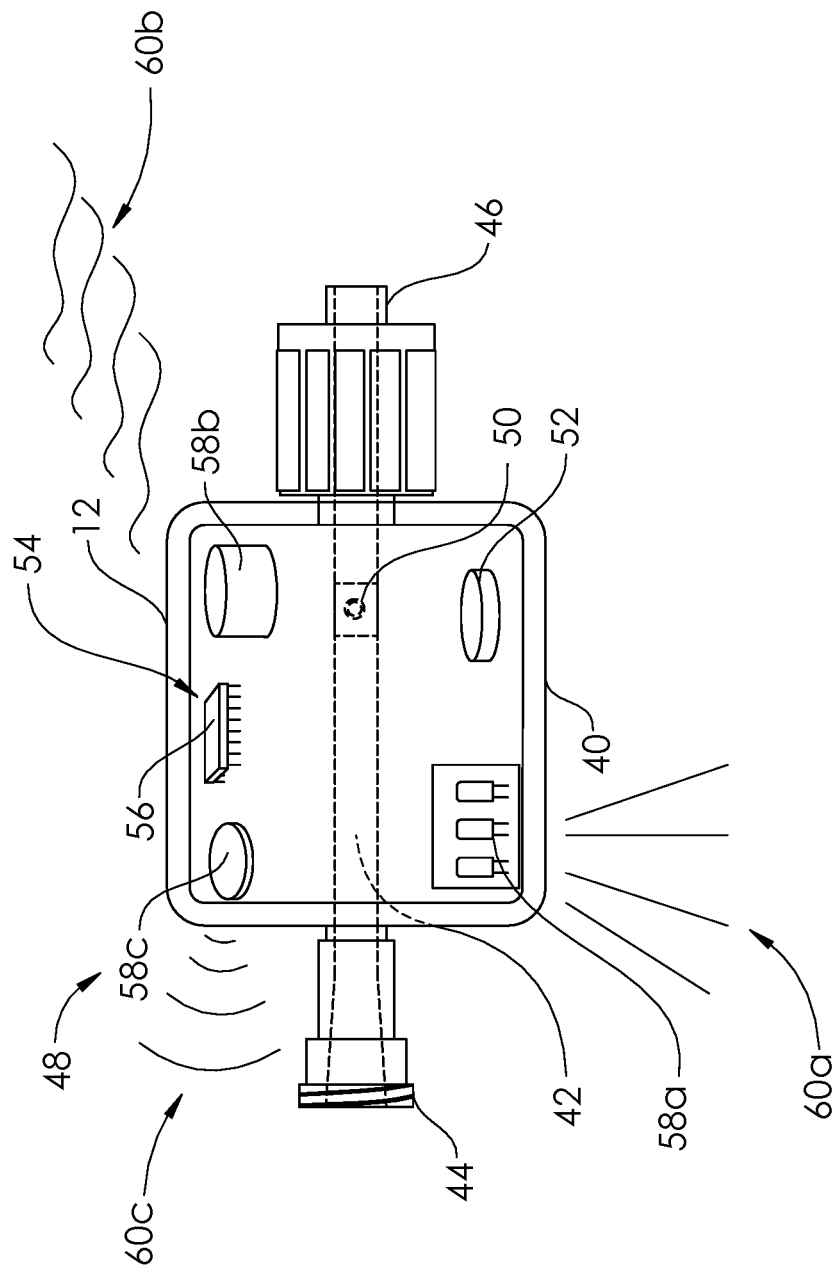
FIG. 44A is a detailed view of an aspiration monitoring system according to a first embodiment or the present disclosure.

The pressure transducer 12 of the aspiration monitoring system 48 is configured to be fluidly coupled between the vacuum source 6 and the aspiration catheter 4. In FIG. 44A, the aspiration monitoring system 48 is illustrated as a self-contained device of a first embodiment. The pressure transducer 12 comprises a housing 40 having a cavity 42 extending between a first port 44 and a second port 46. In some embodiments, the first port 44 comprises a female luer and the second port 46 comprises a male luer. In some embodiments, the first port 44 comprises a female luer lock and the second port 46 comprises a male luer lock, each of which is attachable to and detachable from a corresponding luer lock of the opposite gender. The first port 44 is configured to be coupled to the vacuum source 6, either directly, or with the valve 8 and/or extension tubing 10 connected in between. The second port 46 is configured to be coupled to the aspiration lumen 18 of the aspiration catheter 4, for example, by coupling the second port 46 directly or indirectly to the hub 20 of the aspiration catheter 4. When the aspiration system 2 is used to aspirate body fluids and/or materials, for example blood and/or thrombus, the body fluids and/or materials are aspirated through the aspiration lumen 18 of the aspiration catheter 4 from the angled orifice 24 at the distal end 16 to the female luer connector 22 at the proximal end 14, then pass through the second port 46 of the pressure transducer 12 first, through the cavity 42, and then through the first port 44. Depending on the amount of amount of vacuum (negative pressure) applied by the vacuum source 6, and the amount of flow resistance and resulting pressure drop along the aspiration system 2, the pressure within the cavity 42 will vary. For example, a more viscous fluid like blood, or a fluid having solid, semi-solid, or gel-like particles or portions, will cause more flow resistance through the relatively small aspiration lumen 18 of the aspiration catheter 4 than would water or normal saline solution. Thus the pressure within the cavity 42 of the pressure transducer 12 will decrease (the amount of vacuum will increase) as the flow resistance in the aspiration lumen 18 increases.

For definition purposes, when speaking of the amount of vacuum, a pressure of, for example, −15,000 pascal (−2.18 pounds per square inch, or psi) is a "larger vacuum" than −10,000 pascal (−1.45 psi). Additionally, −15,000 pascal is a "lower pressure" than −10,000 pascal. Furthermore, −15,000 pascal has a larger "absolute vacuum pressure" than does −10,000 pascal, because the absolute value of −15,000 is larger than the absolute value of −10,000. In FIG. 44A, a vacuum sensor 50 is disposed within the cavity 42 of the housing 40 and is in fluid communication with fluid that passes through the cavity 42. The vacuum sensor 50 may be a standard pressure sensor or transducer, including a pressure sensor designed primarily for measuring positive pressure. It may use any type of pressure sensing technology known in the art, including MEMS Technology. In some embodiments, the vacuum sensor 50 is configured for highest accuracy and/or precision within the range of pressures between about 0 pascal to about −101,325 pascal (−14.70 psi), or between about −45,000 pascal (−6.53 psi) and about −90,000 pascal (−13.05 psi), or between about −83,737 pascal (−12 psi) and about −96,527 pascal (−14 psi). In some embodiments, the power requirement for the vacuum sensor may range from 2.5 volts DC to 10 volts DC. In some embodiments, the vacuum sensor 50 may be an analog gauge with an output voltage. In the self-contained embodiment of the FIG. 44A, the vacuum sensor 50 is powered by one or more battery 52. Based on the power requirements of the vacuum sensor 50, and the power requirements of other components of the aspiration monitoring system 48 described herein, in some embodiments the one or more battery 52 may range between 1.5 volts and nine volts. Also contained within the housing is a measurement device 54, which in some embodiments may comprise a microprocessor. The measurement device 54 is coupled to the vacuum sensor 50 and receives signals from the vacuum sensor 50 indicative of real time measured pressure. In some embodiments, the measurement device 54 includes a memory module 56 in which information is stored that may be used by the measurement device 54, for example, in calculations. Information may include, for example, an array of one or more pressure values. In some embodiments, the array of one or more pressure values may be correlated with one or more different corresponding system models or catheter models. The vacuum sensor 50 may be used in some cases for detecting the presence or amount of vacuum alone, for the purpose of monitoring whether the vacuum source 6 (e.g., syringe) is significantly full, and thus needs to be changed. The vacuum sensor 50 may be used in some cases for detecting whether there is a vacuum in the system or not. For example, whether the vacuum has been applied or not (e.g., the vacuum source has been turned on or off).

One or more communication devices 58a, 58b, 58c are included within the aspiration monitoring system 48 and are coupled to the measurement device 54. Each of the one or more communication devices 58a-c are configured to generate a type of alert comprising an alert signal 60a-c, in response at least in part to activity and output of the measurement device 54. In some embodiments, the communication device 58a may include one or more LEDs (light emitting diodes) configured to generate a visible alert via a visible alert signal 60a, such as light that is continuously illuminated, or is illuminated in a blinking pattern. In some embodiments, the LEDs may be oriented on multiple sides of the communication device 58a, so that they may be easily seen from a variety of different locations. In some embodiments, lights other than LEDs may be used. Light pipes or other lighting conduits may also be incorporated in embodiments, to further place visual indicators at multiple locations and/or orientations. In some embodiments, the communication device 58b may include one or more vibration generators configured to generate a tactile alert via a tactile alert signal 60b, which may include, but is not limited to, vibration or heat. In some embodiments, the vibration device may be similar to a video game controller. In some embodiments, the vibration generator may comprise a piezoelectric device which is configured to vibrate when a voltage is applied. In some embodiments, the communication device 58c may include one or more sound generating devices configured to generate an audible alert via an audible alert signal 60c, such as a continuous noise, or a repeating noise. The communication device 58c in some embodiments may comprise a loudspeaker for generation of any variety of sounds, at any variety of frequencies (Hz) or sound pressures (dB) within the human audible range and/or human tolerance range. The communication device 58c may even be configured to generate sounds that are outside the human audible range in embodiments wherein the signal is intended to be felt as a vibration or other tactile sensation, instead of an audible sensation. In some embodiments, the sound generating device may comprise a buzzer which is configured to sound one or more audible pitches when a voltage is applied. In some embodiments a piezoelectric device, such as that described in relation to the communication device 58b may also serve as a sound generating device, included as communication device 58c. The alert signal 60a-c can at times serve as a "wake up" alarm for the user, in cases where the user has become too focused on other factors during the procedure. A user of an aspiration system 2 may desire to be notified of several conditions which may occur during use of the aspiration system 2. These potential conditions include, but are not limited to clogging, a loss of vacuum due to filling of the vacuum source 6 and or a breach, break or puncture in the aspiration system 2, and the engagement or aspiration of non-fluid, solid or semi-solid material such as thrombus. The aspiration monitoring system 48 of FIG. 44A is configured to alert users of an aspiration system 2 about real time status of the aspiration system 2, including operational conditions, which include: whether vacuum is being applied or not; flow conditions, which include whether a thrombus is engaged, whether a thrombus is being actively aspirated, whether the system is leaking air, whether the system is clogged, whether the vacuum source 6 is full and/or needs to be changed; or other potential set up issues. The real time feedback provided frees a user or operator from the need of excessive personal monitoring of the vacuum source 6, extension tubing 10, or other portions of the aspiration system 2, for improper or undesired flow or operation conditions, and thus allows the user to focus more attention on the patient being treated. The user is kept aware of whether a clot is being aspirated or has been aspirated, or whether there is a clog. Additionally, the user is kept aware of whether there is too large an amount of blood being removed from the patient, or whether there are fault conditions like system leak or tubing kink. A tubing kink distal to the vacuum sensor 50 may be identified (for example by an increase in measured vacuum) and a tubing kink proximal to the vacuum sensor 50 may be identified (for example, by a loss or degradation of vacuum). In some cases, the user may attempt to operate the catheter with a vacuum source 6 that is already full (and thus has no significant vacuum). In some cases, a user may even forget to open the valve 8 to begin suction, but the aspiration monitoring system, 48 can also identify that the system is not yet functioning, and communicate a list of potential errors or specific errors (for the particular pressure waveform measured). By having the real-time awareness of the many factors related to the operating status, the procedure is made safer, the time of the procedure may be reduced, and blood loss may be reduced.

The pressure transducer 12 of the aspiration monitoring system 48 is configured to continuously measure and monitor the absolute pressure amplitude within the closed system of the aspiration system 2, and also is configured to measure and monitor the relative pressure over time to detect noteworthy flow changes within the flow circuit of the aspiration system 2. Some changes are discernible via absolute pressure measurement, while more subtle pressure deflections may be compared to a stored library in memory. Noteworthy conditions may be signaled to the user when appropriate. In some embodiments, the unfiltered signal may be amplified by an amplifier and filtered by a filter, for example, to increase the signal-to-noise ratio. Examples of the (background) noise 57 in an unfiltered signal can be seen in FIGS. 46A-46D (labeled in FIG. 46A). In some embodiments, one or more algorithms may be used, as described herein, to identify particular conditions of interest.

FIG. 44B illustrates a second embodiment of an aspiration monitoring system 62 having a pressure transducer 12 having a vacuum sensor 50 disposed within the cavity 42 of a housing 40. The vacuum sensor 50 may be powered by at least one battery 52. In some embodiments, the pressure transducer 12 may be reusable, and may be configured to allow charging of the battery 52, or of a capacitor (not shown) by direct charging methods, or by inductive power transfer methods and devices known in the art. Unlike the aspiration monitoring system 48 of FIG. 44A, the aspiration monitoring system 62 of FIG. 44B comprises a measurement device 64, memory module 66, and communication device 68 which are external to the pressure transducer 12. A power module 72, also external, may be used to power any of the measurement device 64, memory module 66, or communication device 68. The communication device 68 may be any of the communication device 58a, 58b, 58c described in relation to the aspiration monitoring system 48 of FIG. 44A, and are configured to product an alert via an alert signal 70. The communication device 68 may be portable so that it may be positioned close to the user.

Figure 44C:
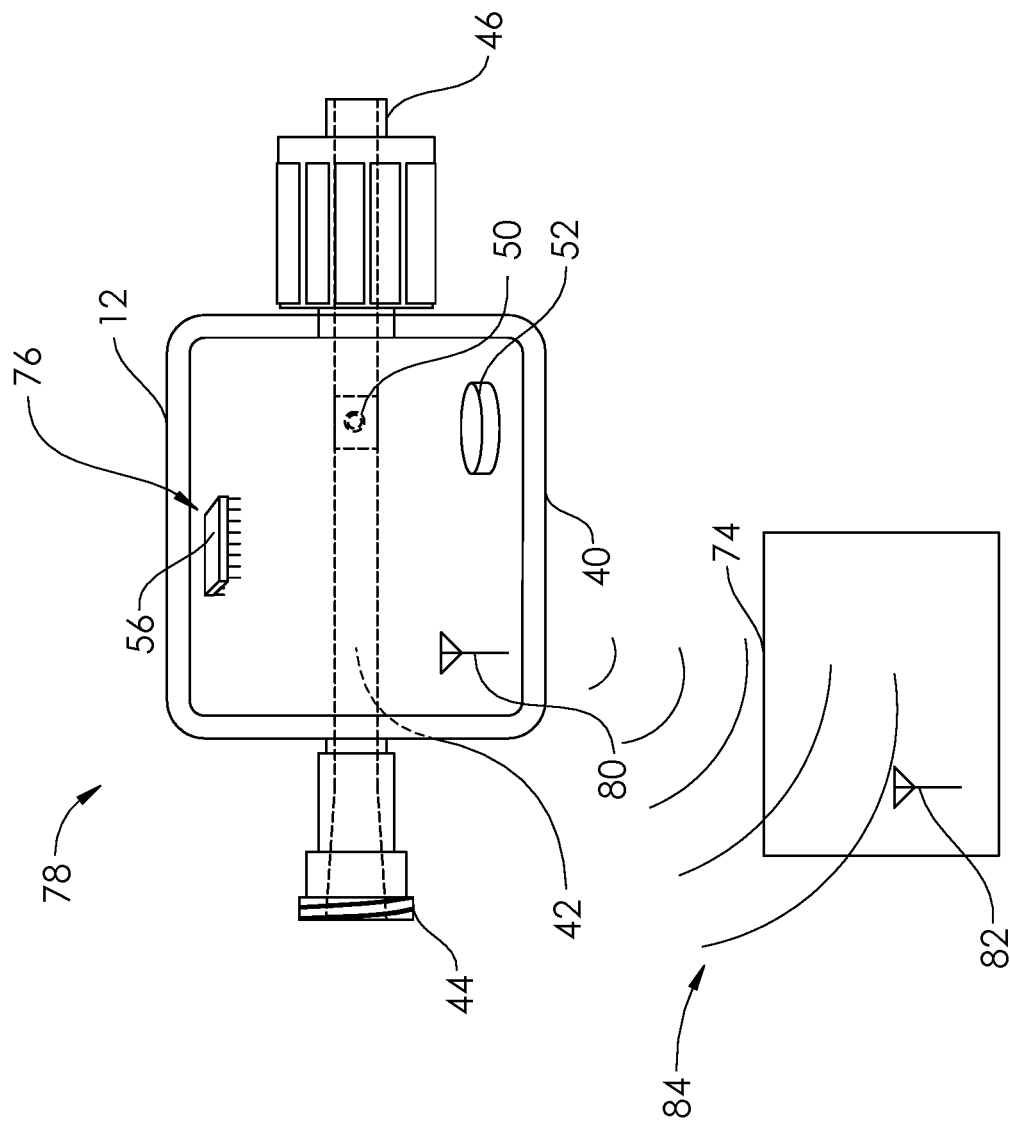
FIG. 44C is a view of an aspiration monitoring system according to a third embodiment of the present disclosure.

In some embodiments, the communication device 68 may be wearable by the user. FIG. 44C illustrates an aspiration monitoring system 78 which includes an antenna 80 coupled to a measurement device 76. The measurement device 76 is similar to the measurement device 54 of prior embodiments, except that it wirelessly sends a communication signal 84 via the antenna 80 to a corresponding antenna 82 of a communication device 74. In some embodiments, the communication device 74 comprises a wristband which the user wears, and which may include a vibration generator or heat generator. In some embodiments, the communication device 74 comprises an audio speaker which may be attached to equipment or even to the patient or user. In some embodiments, the communication device 74 comprises an audio speaker on an earpiece or earbud that the user may wear. In some embodiments, Bluetooth® communication technology may be used. The real time feedback supplied by the aspiration monitoring system 62 may decrease the time that the aspiration system 2 is actively aspirating without being engaged with a thrombus, thus minimizing the amount of nonthrombotic blood lost by aspiration. This may be particularly beneficial in larger bore catheters, for example in catheters having a diameter of 7 French or larger. The real time feedback may also minimize the amount of total time that catheters are tracked back-and-forth through the blood vessels, minimizing potential damage to the intima of the blood vessels, dissection of the blood vessels, or distal embolization. By lowering the risk of the aspiration catheter tip getting caught (via suction) against the blood vessel wall, the distal end of the aspiration lumen may be more aggressively designed for optimized aspiration characteristics. The technique of using the aspiration catheter may additionally be able to be performed in a more sophisticated manner, with continual or continuous knowledge of the vacuum status. For example, a piece of thrombus may be aspirated, followed by a "chaser" of blood aspiration, followed by another piece of thrombus, etc.

Figure 45A:
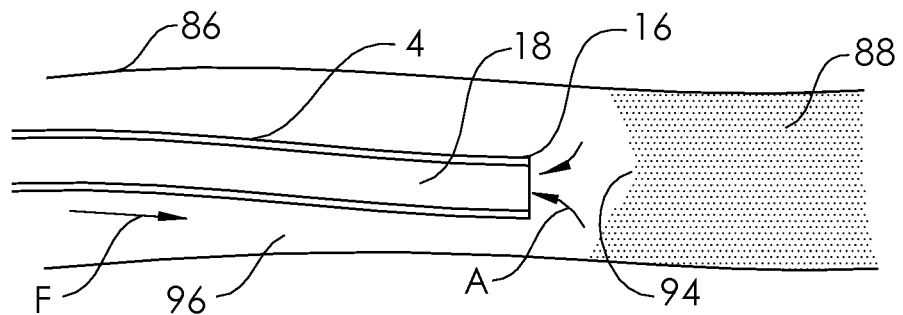
FIG. 45A is a sectional view of an aspiration catheter in a blood vessel prior to contact with a thrombus.
Figure 46A:
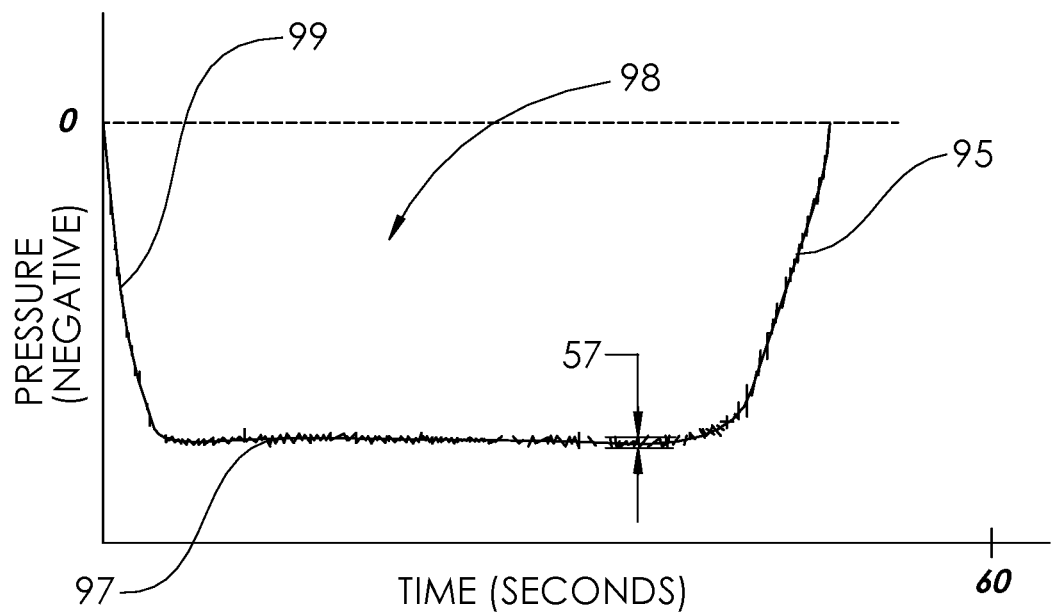
FIG. 46A is a graphic representation of pressure vs. time for the condition of FIG. 45A.

FIG. 45A illustrates the distal end 16 of an aspiration catheter 4 within a blood vessel 86 having at least one thrombus 88. The aspiration catheter 4 is being advanced in a forward direction F, but the distal end 16 of the aspiration catheter 4 has not yet reached the proximal extremity 94 of the thrombus 88. A vacuum source 6 (FIG. 43) has been coupled to the aspiration lumen 18 of the aspiration catheter 4 and activated (i.e. the valve 8 is open) causing blood 96 to be aspirated into the aspiration lumen 18 (arrows A). Turning to FIG. 46A, a corresponding curve 98 is represented for the normal fluid (e.g. blood) vacuum over time for the condition of FIG. 45A. The curve 98 represents vacuum pressure over time sensed by the vacuum sensor 50 of any of the embodiments presented. No leaks are present and no thrombus is being evacuated, and therefore the curve 98 includes a downward slope 99 when the vacuum source 6 increases the vacuum up (lowers the pressure) within the cavity 42 of the pressure transducer 12 to a relatively steady state. The steady pressure curve 97 continues while blood 96 is being aspirated. As the vacuum is decoupled from the aspiration lumen 18, for example by closing the valve 8 or by detaching any two of the ports (e.g. luers), or if the vacuum source 6 fills completely with blood 96, then an upward slope 95 is measured.

The measurement device 54, 64 is configured to compare the curve 97 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Thrombus encountered," or "No thrombus encountered." A different type of sound may be used for each of a plurality of "modes": "Thrombus encountered," "Actively flowing," "No Vacuum." For example, a buzzing sound for "Thrombus encountered," a beep for "No vacuum," etc. The various characteristics of sound that may be varied include, but are not limited to timbre, or sound quality, spectrum, envelope, duration, phase, pitch (frequency), and number of sounds (repetition). Communication device 58c may vibrate or heat in a characteristic pattern, for example, a certain number of repetitions or a certain frequency between repetitions. The user may determine that an additional fluoroscopic image (e.g. angiography) or other imaging modalities may be necessary to better identify the location of the thrombus 88.

Figure 45B:
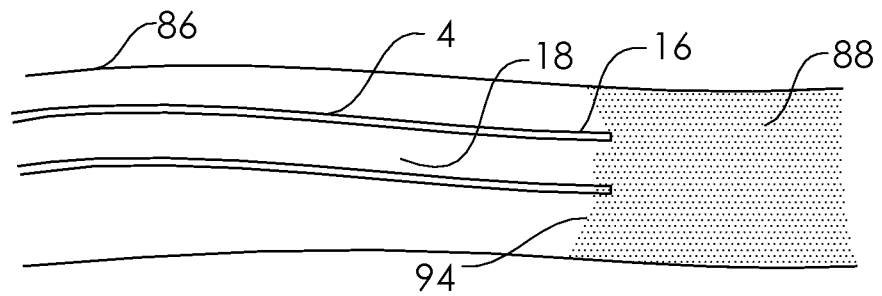
FIG. 45B is a sectional view of an aspiration catheter in a blood vessel upon contact with a thrombus.
Figure 46B:
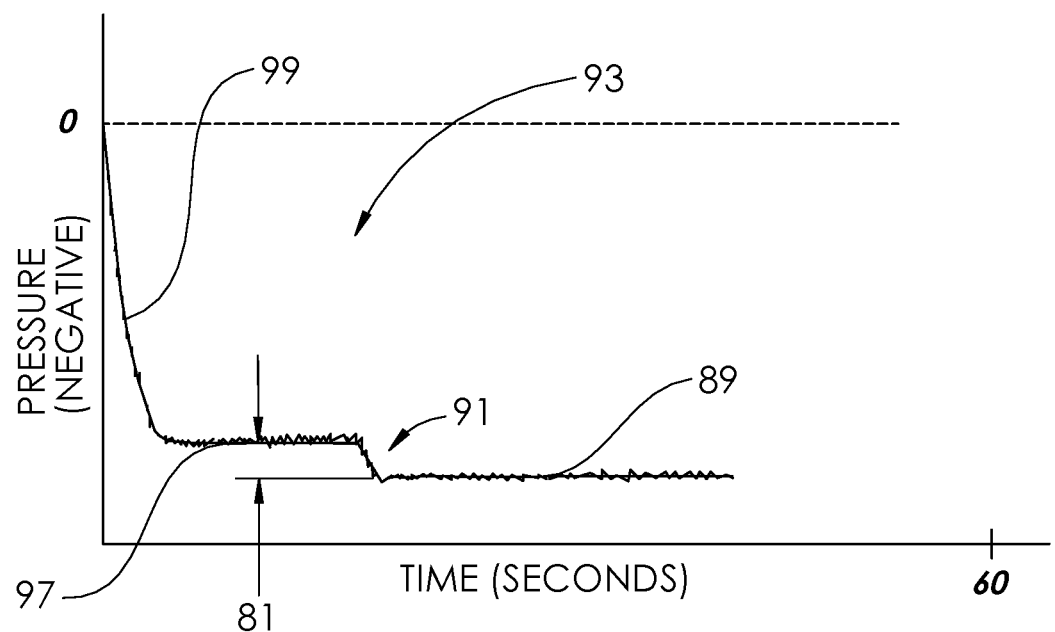
FIG. 46B is a graphic representation of pressure vs. time for the condition of FIG. 45B.
Figure 46C:
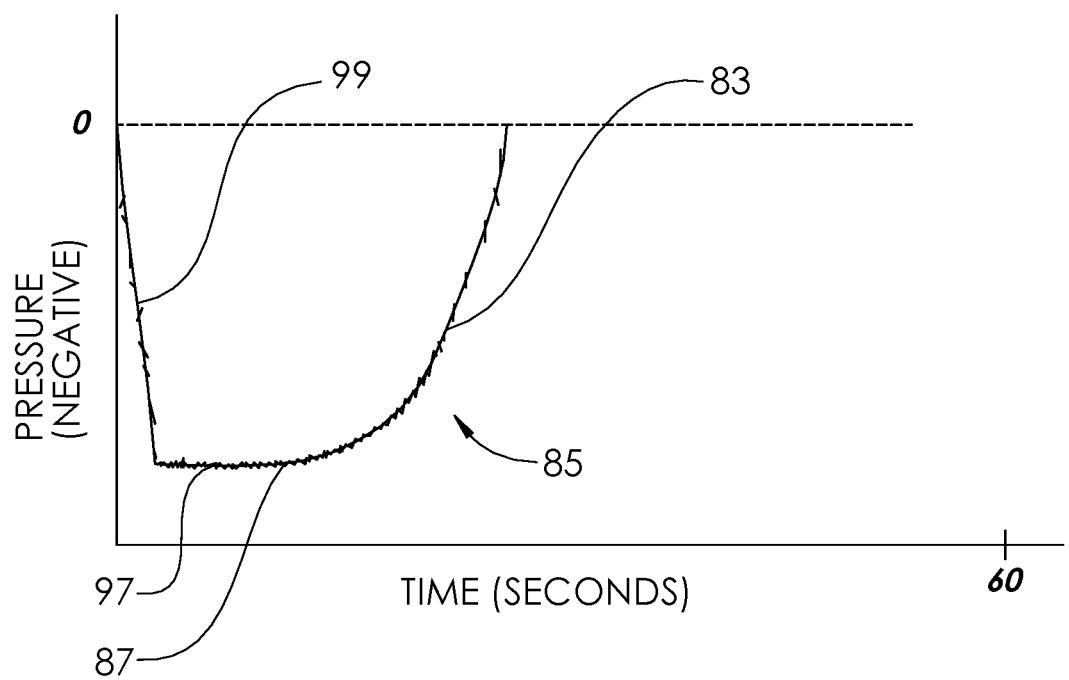
FIG. 46C is a graphic representation of pressure vs. time for the condition of FIG. 45C.

FIG. 45B illustrates the distal end 16 of an aspiration catheter 4 advanced to a position such that the distal end 16 of the aspiration catheter 4 contacts the proximal extremity 94 of the thrombus 88. The corresponding curve 93 in FIG. 46B represents vacuum pressure over time sensed by the vacuum sensor 50 of any of the embodiments presented. The curve 93 initially has a downward slope 99 followed by a steady pressure curve 97, as in the condition of FIG. 45A, graphed in FIG. 46A, however, when the distal end 16 of the aspiration catheter 4 contacts the proximal extremity 94 of the thrombus 88, if the aspiration causes a portion of the thrombus 88 (for example a large or relatively hard portion) to enter and become trapped in the aspiration lumen 18, then a clog condition occurs. A similar condition occurs if the distal end 16 of the aspiration catheter 4 is caught on the thrombus 88 by the vacuum, with virtually nothing flowing through the aspiration lumen 18. In either condition, the curve 93 includes a deviation (or disturbance) in fluid pressure 91. If the clog (or stuck condition) continues, then a flat, depressed pressure 89 is measured.

The measurement device 54, 64 is configured to compare the curve 93 with information stored in the memory module 56, 66 to identify this condition. In some embodiments, the measurement device 54, 64 uses an algorithm to make the comparison. In some embodiments, a pre-set pressure differential $\Delta P_1$ may be stored in the memory module 56, 66 as a threshold, whereby the measurement of a pressure difference 81 less than this threshold does not result in the measurement device 54, 64 commanding the communication device 58a-c, 74 to send an alert signal 60a-c, 70. In some embodiments, when the pressure difference 81 is greater than (or greater than or equal to) the pre-set pressure differential $\Delta P_1$, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "Clog Condition." Communication device 58c may vibrate or heat in a characteristic pattern, for example, a certain number of repetitions or a certain frequency between repetitions. When the user realizes that the clog condition is present, the user may pull on the aspiration catheter 4 and readvance it, in an attempt to contact a portion of the thrombus 88 that can be aspirated. If a portion of the thrombus is clogged in the aspiration lumen 18, and repositioning of the aspiration catheter 4 does not produce good results, the aspiration catheter 4 can be removed and the aspiration system 2 can be repurged, for example by a positive pressurization.

Figure 45C:
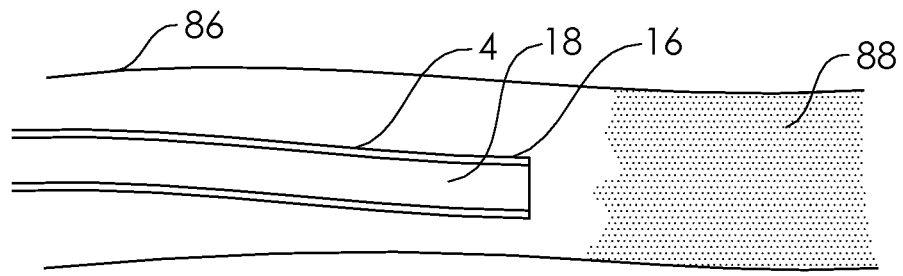
FIG. 45C is a sectional view of an aspiration catheter during a loss of vacuum.

FIG. 45C illustrates the distal end 16 of the aspiration catheter 4 in a general situation during which a breach in the aspiration system 2 has occurred. For example, a break, leak, puncture, pinhole, loosening, or disconnection may cause air to be pulled into the aspiration lumen 18 of the aspiration catheter 4, the cavity 42 of the pressure transducer 12, of the interior of the extension tubing 10, valve 8, or vacuum source 6. As graphed in the curve 85 of FIG. 46C, a downward slope 99 and a subsequent steady pressure curve 97 are measured, but at the point in time of the breach 87 an upward slope 83 begins.

The measurement device 54, 64 is configured to compare the curve 85 with information stored in the memory module 56, 66 to identify this condition. In some embodiments, the measurement device 54, 64 uses an algorithm to make the comparison. In some embodiments, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. Communication device 58b may create a characteristic sound, or may generate an audio message in a number of languages. For example, the audio message may state, "System Leak." Communication device 58c may vibrate or heat in a characteristic pattern, for example, a certain number of repetitions or a certain frequency between repetitions. Upon receiving the alert, the user will check the components of the aspiration system 2 and either fix the breach or replace one or more of the components of the aspiration system 2. For example, in some cases, the communication device 58a-c, 74 may alert the user when the measurement device 54, 64 confirms a loss of vacuum, allowing the user to change or recharge the vacuum source 6, which has become depleted (e.g. by filling with blood and/or thrombus).

Figure 45D:
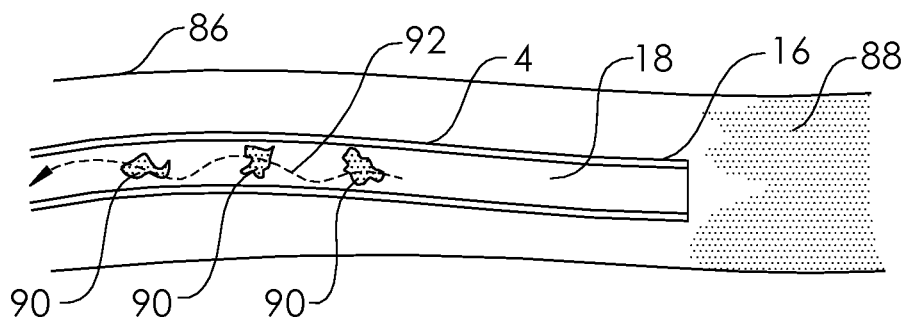
FIG. 45D is a sectional view of thrombi being aspirated through an aspiration catheter.

FIG. 45D illustrates the distal end 16 of the aspiration catheter 4 during the successful aspiration of pieces or portions 90 of the thrombus 88. In some cases, the pieces or portions 90 may follow a tortuous path 92, due to disturbances or collisions with the inner wall of the aspiration lumen 18 while being pulled through the aspiration lumen 18. In some cases, the pieces or portions 90 may catch and slip within the inner wall of the aspiration lumen 18, for example, do to variance of the inner diameter of the aspiration lumen 18 along the length. Either of these situations can cause a corresponding series of increases and decreases in the pressure being sensed by the pressure transducer 12, while the pieces or portions 90 are traveling through the aspiration lumen 18. As graphed in the curve 79 of FIG. 46D, a downward slope 99 and a subsequent steady pressure curve 97 are measured, but as the pieces or portions 90 of thrombus 88 travel down the aspiration lumen 18 of the aspiration catheter 4, a deviation 77 of fluid pressure comprising a one or more decreases and increases in pressure (increases and decreases in vacuum pressure) is measured. As the pieces or portions 90 of thrombus 88 exit the proximal end of the aspiration lumen 18 of the aspiration catheter 4, a second steady pressure curve 75 is measured. The duration 67 of the deviation 77 is the amount of transit of the particular significant pieces or portions 90 of thrombus 88. The duration 67 can range quite a bit, but in some cases may be less than a second or up to about 30 seconds. A single thrombus being aspirated may cause a single decrease in pressure (a blip) which is identified by the measurement device 54, 64. Subsequently, this occurrence may be communicated to the user by the communication device 58a-c, 74. When again additional pieces or portions 90 of thrombus 88 are aspirated into and travel down the aspiration lumen 18 of the aspiration catheter 4, another deviation 73 of fluid pressure comprising a one or more decreases and increases in pressure (increases and decreases in vacuum pressure) is measured. At the end of the curve 79, the vacuum source 6 is shown filling completely with blood 96 and the pieces or portions 90 of thrombus 88, and so an upward slope 95 is measured.

The measurement device 54, 64 is configured to compare the curve 79 with information stored in the memory module 56, 66 to identify when the pieces or portions 90 of thrombus 88 are actively being aspirated, as in deviation 77 and deviation 73, and when the pieces or portions of thrombus 88 are not being actively, or substantially, aspirated, as in steady pressure curve 97, the steady pressure curve 75, and the steady pressure curve 71. In some embodiments, the measurement device 54, 64 uses an algorithm to make the comparison. In some embodiments, a pre-set pressure differential $\Delta P_2$ may be stored in the memory module 56, 66 as a threshold, whereby the measurement of a pressure difference 69 less than this threshold does not result in the measurement device 54, 64 commanding the communication device 58a-c, 74 to send a first type of alert via an alert signal 60a-c, 70. In some embodiments, when the pressure difference 69 is greater than (or greater than or equal to) the pre-set pressure differential $\Delta P_2$, the measurement device 54, 64 then sends a signal to the communication device 58a-c, 74, and the communication device 58a-c, 74 generates an appropriate alert. Communication device 58a, for example a particular color LED, may be illuminated, or an LED may flash in a particular pattern or number of flashes. In some embodiments, the communication device 58a may comprise a light whose intensity increases proportionally with the pressure. Communication device 58b may create a characteristic sound, or may generate an audio message in a number of languages. For example, the audio message may state, "Thrombus being aspirated." In some embodiments, communication device 58b may comprise one or more noises or beeps. In some embodiments, the communication device 58b may comprise a particular series of beeps corresponding to each different condition. For example, three short beeps may correspond to no thrombus being aspirated, while five long, loud beeps may correspond to a system leak. In some embodiments, a plurality of different tones (pitches) may be used to alert a user about different conditions. As an example, a low pitch sound may be used for a first condition (e.g. no thrombus being aspirated) and a second, higher pitch sound may be used for a second condition (e.g. a system leak). In some embodiments, a plurality of different tones may be used to alert a user about a first condition and a second plurality (e.g. in a different combination, or with additional tones) may be used to alert a user about a second condition. Communication device 58c may vibrate or heat in a characteristic pattern, for example, a certain number of repetitions or a certain frequency between repetitions. When the user realizes that the thrombus is being aspirated, the user may choose to advance (or retract) the aspiration catheter 4, for example with fluoroscopic visualization, along the length of the thrombus 88, in an attempt to continue the aspiration of the thrombus 88. In some cases, the user may choose to stop the advancement or retraction of the aspiration catheter 4 at a certain amount of time after the alert is generated, in order to allow the pieces or portions 90 of thrombus 88 to completely exit the aspiration lumen 18. When the measurement device 54, 64 identifies a subsequent steady pressure curve 75, 71 that follows a deviation 77, 73, the measurement device 54, 64 in some embodiments sends a signal that causes the communication device 58*a-c*, 74 to generate a second type of alert via an alert signal 60*a-c*, 70. For example, in some embodiments, communication device 58*b* may send an audio message that states, "Thrombus no longer being aspirated." When the user realizes that the thrombus is no longer being aspirated, the user may advance or retract the aspiration catheter, in an attempt to contact another portion of the thrombus 88 that can be aspirated. In some embodiments, the deviation 77 may be positively identified as a true deviation indicating thrombus being actively aspirated, pressure difference 69 is between about 700 pascal and about 1700 pascal. In some embodiments, the deviation 77 may be positively identified as a true deviation indicating thrombus being actively aspirated, pressure difference 69 is between about 1000 pascal and about 1300 pascal. In some embodiments, the deviation 77 may be positively identified as a true deviation indicating thrombus being actively aspirated, pressure difference 69 is about 1138 pascal. The pressure difference 69 may be measured by determining a baseline pressure 63 and a peak pressure 61 and determining the absolute value difference. For example:

Absolute value difference (AVD)=|(−89,631 pascal)−(−90,769 pascal)|=1138 pascal

Or for example:

Absolute value difference (AVD)=|(−43,710 pascal)−(−45,102 pascal)|=1281 pascal

The pressure difference 81 (FIG. 46B) may also represent a deviation that may be identified in a similar manner, after which the communication device 58*a-c*, 74 generates an appropriate alert, such as, "Clog condition."

Figure 46D:
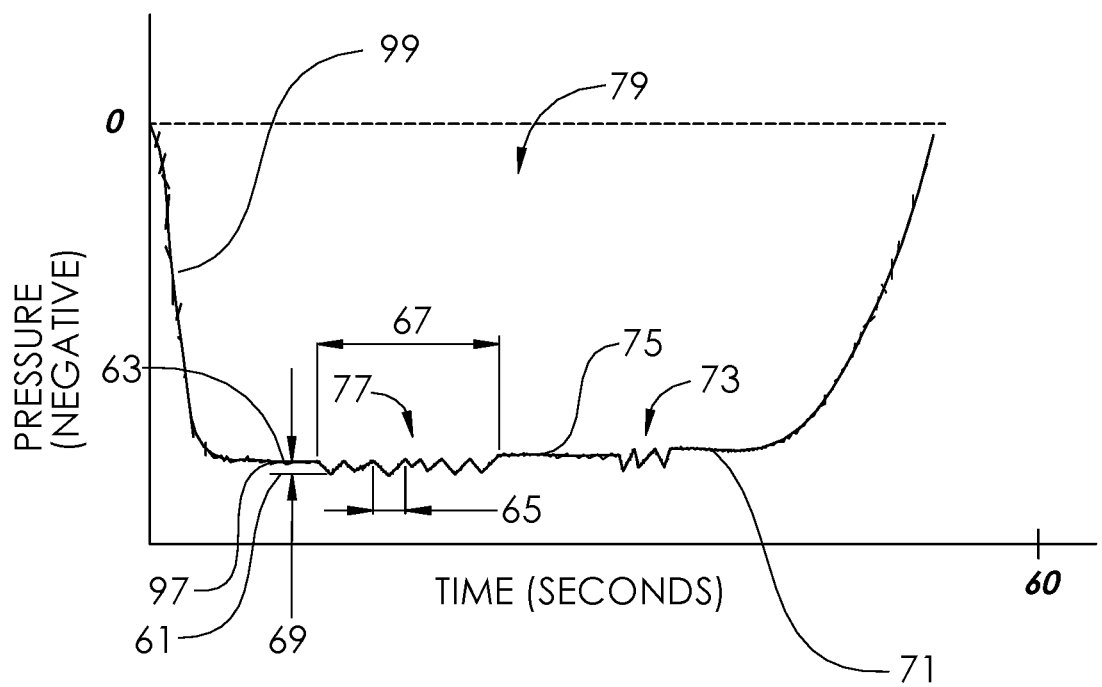
FIG. 46D is a graphic representation of pressure vs. time for the condition of FIG. 45D.
Figure 47:
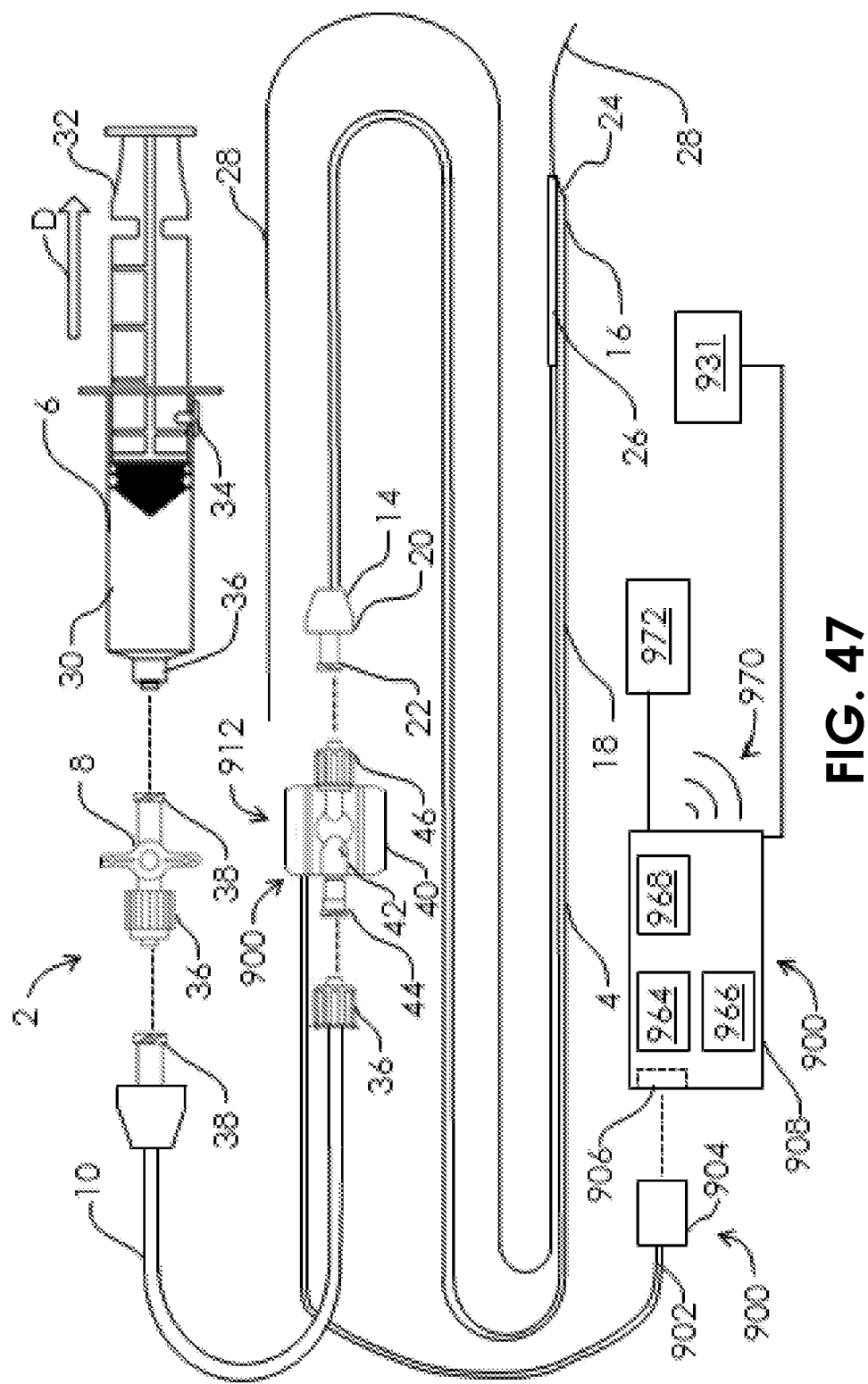
FIG. 47 is a plan view of a system for aspiration according to another embodiment of the present disclosure.
Figures 50, 51:
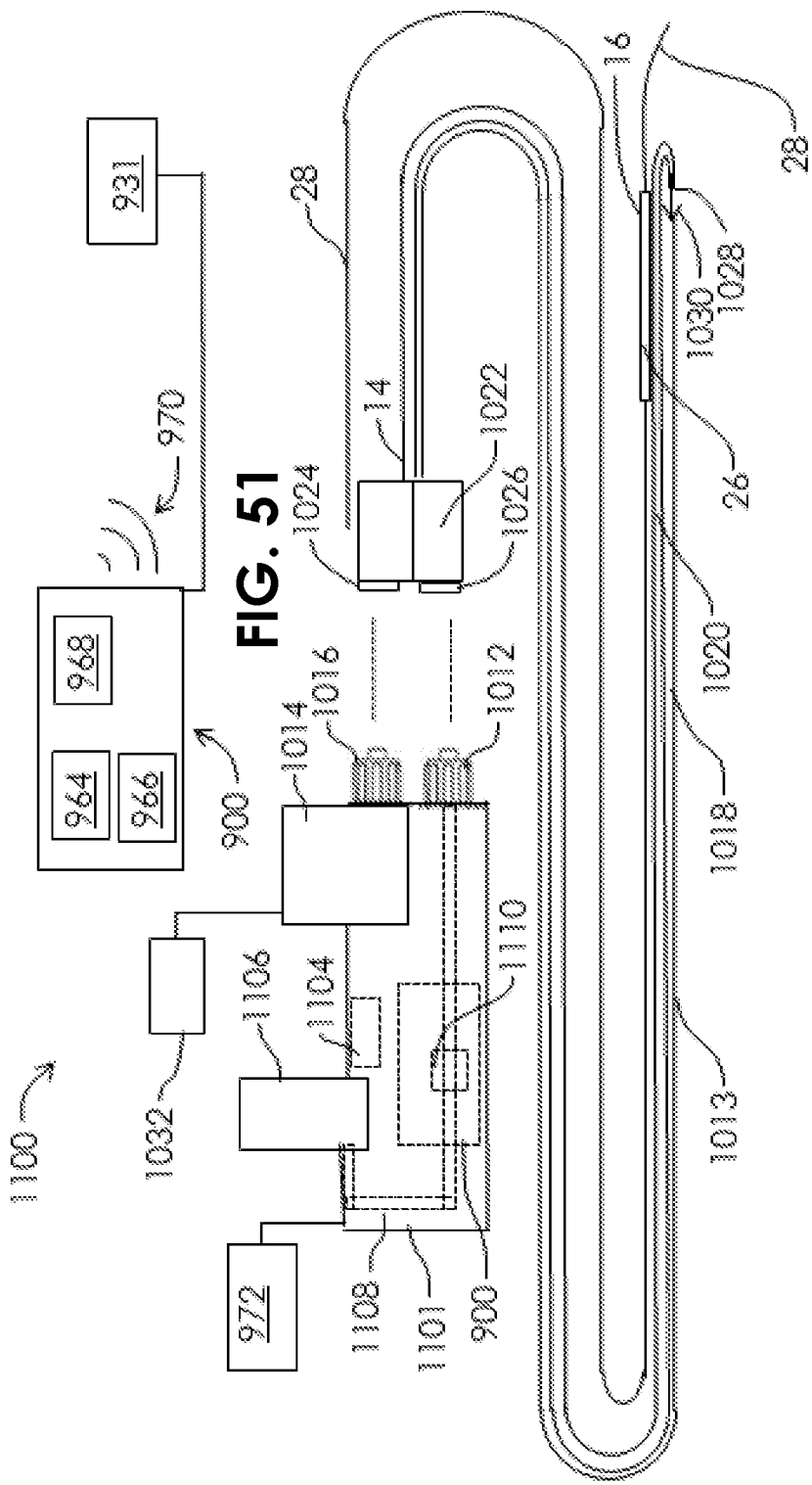
FIG. 50 is a plan view of a system for aspiration according to another embodiment of the present disclosure.
FIG. 51 is a detailed view of an aspiration monitoring system of the system for aspiration of FIG. 50.

Because vacuum pressure is a negative pressure, the peak pressure 61, as shown in FIG. 46D, is actually a lower number than the baseline pressure 63. In some embodiments, the measurement device 54, 64 may also be configured to make a comparison, for example by using an algorithm, between a stored differential time ti and a duration 65 of a single one of the more or more decreases and increases in pressure in the deviation 77. For example, in some embodiments, the deviation may be positively identified as a true deviation indicating thrombus being actively aspirated, if the duration is between about 0.001 seconds and about 0.50 seconds. In some embodiments, the deviation may be positively identified as a true deviation indicating thrombus being actively aspirated, if the duration is between about 0.005 seconds and about 0.10 seconds. In some embodiments, the deviation may be positively identified as a true deviation indicating thrombus being actively aspirated if the duration is between about 0.05 seconds and about 0.20 seconds. In some embodiments, the measurement device 54, 64 is configured to recognize deviation 77 after two or more decreases and increases in pressure are measured. In some embodiments, the measurement device 54, 64 is configured to recognize deviation 77 after five or more decreases and increases in pressure are measured. In some embodiments, the measurement device 54, 64 is configured to recognize deviation 77 after ten or more decreases and increases in pressure are measured.

The baseline pressure 63 may in some embodiments be predetermined and may be stored in the memory module 56, 66. In some embodiments, the baseline pressure 63 may be stored in the memory module 56, 66 during the manufacture of the aspiration monitoring system 48, 62, 78, but the baseline pressure 63 may also be input by the user prior to or during a particular procedure. In some embodiments, the baseline pressure 63 may be determined or otherwise defined by the measurement device 54, 64, 76 based on averaging of a particular number of samples of measured pressure. The baseline pressure 63 may be constructed as a moving average, such as a running average or rolling average. Several types of moving average may be used, including a simple moving average, a cumulative moving average, a weighted moving average, or an exponential moving average. In any of these cases, a threshold may be determined by the measurement device 54, 64, 76 based on the determined baseline pressure 63 and a known pressure differential $\Delta P$. In some cases, a pressure differential $\Delta P$ may even be calculated by the measurement device 54, 64, 76 based on the determined baseline pressure 63 and a known threshold.

Insertion of the pressure transducer 12 in line in either the embodiment of FIG. 44A or the embodiment of FIG. 44B does not measurably change performance characteristics of the aspiration system 2, because the cavity 42 is relatively short and has a relatively large inner diameter, and thus is not a significant source of fluid flow resistance. In some embodiments, the inner diameter may be between about 2.2 mm (0.086 inches) and about 3.2 mm (0.125 inches). In some embodiments, the measurement device 54, 64, 76 need not include a microprocessor, as pre-defined set points (e.g. for certain thresholds) may be included in firmware, microcontroller, or other locations. In some embodiments, including but not limited to the embodiment of FIG. 44B, the pressure transducer 12 may be an off-the-shelf blood pressure monitor system, which is modified or augmented with other components. In some embodiments an off-the-shelf blood pressure monitor system may be used as the output of the aspiration monitoring system 48, 62, 78. In some embodiments, an aspiration catheter 4 may have a pressure transducer in the distal end 16. This pressure transducer may be used as the pressure transducer 12 of the aspiration monitoring system 48, 62, 78. In some embodiments, a pressure sensor may be located within a Tuohy-Borst valve, and introducer sheath, a guiding catheter, or another component of the system through which is in fluid communication with the aspiration lumen 18. In some embodiments, the pressure sensor may be located anywhere within the aspiration lumen of the aspiration catheter.

In some embodiments, instead of an LED, the visual alert is provided by a communication device 58*a* comprising a display which displays visual messages of text in a particular language, for example, "Thrombus encountered," "No thrombus encountered," "Clog condition," "System leak," "Loss of vacuum," "Thrombus being aspirated," or "Thrombus no longer being aspirated." The visual messages may be combined with any of the other alert signals 60*a-c*, 70 described herein. The aspiration monitoring system 48, 62, 78 described herein give real time awareness to users performing aspiration procedures, such as the removal of thrombus via an aspiration system 2. One skilled in the art will recognize that by knowing the real time condition of the aspiration system 2, the user is able to immediately make changes to the procedure in order to optimize results, increase safety for the patient and/or medical personnel, reduce costs (e.g. number of vacuum sources 6 required), and reduce procedure time (also a cost benefit). Because the user is typically performing multiple tasks during an aspiration procedure, the sensory aid provided by the aspiration monitoring system 48, 62, 78 allows the user to focus on these tasks without having to continually attempt to monitor conditions which are often difficult to visually monitor. The user may also modify and control the aspiration monitoring system 48, 62, 78 via an input 59 (FIG. 44B), which may comprise a data entry module, keyboard, or a series of buttons with a display. The input 59 may in some embodiments comprise an auditory input which accepts voice commands. Alternatively, the user may input information and control the aspiration monitoring system, 48, 62, 78 remotely. Some of the alerts which the user may select or deselect in the aspiration monitoring system 48, 62, 78 include, but are not limited to: whether the aspiration system 2 is potentially blocked or clogged, or is flowing normally; whether thrombus has been contacted or not; whether a clog has occurred; whether the vacuum source 6 is adequate, or whether it has been depleted and requires replacement; whether there is a leak in the aspiration system 2; whether setup or connection of the components of the aspiration system 2 was done correctly or incorrectly; whether to advance the catheter distally; whether to retract the catheter; whether to continue moving the catheter at the same speed; whether to increase or decrease the speed of catheter advancement; whether thrombus is actively being aspirated; and whether thrombus stops being actively aspirated. As the user becomes familiar with the aspiration monitoring system 48, 62, 78, the user may even begin to make certain responses to the system subconsciously. For example, a user may automatically pull back the catheter upon hearing a clot warning signal (e.g., three beeps), and may automatically begin advancing the catheter and/or start fluoroscopic visualization upon hearing a free blood flow signal (e.g., two beeps). By being "at one" with the aspiration monitoring system 48, 62, 78 and the catheter, the user optimizes reactions and actions. This may be helpful improving the skill of having the catheter take a small "bite" of thrombus, and following the "bite" with a "chaser" of some fast flowing blood, the clean/open the lumen. This would also help minimize the chance of clogging, and would in turn reduce maintenance or corrections of the system (removing the catheter, flushing the lumen outside of the patient, replacing the catheter). The overall experience for the user is improved, as the user received instant gratification for good results, and is instantly notified of errors or instances for concern.

In some embodiments, alternate power sources may be used, for example, standard AC power with or without an AC/DC convertor; direct connection to existing equipment (e.g. vacuum pumps, etc.); solar power. The aspiration monitoring system 48, 62, 78 may be packaged sterile or may be resterilizable by techniques known by those skilled in the art. In some embodiments, flow or volume gauges may be used in conjunction with or instead of the pressure gauge 12, in order to determine, for example, a clog, or a change in the amount of vacuum. In some embodiments, the input 59, power module 72, measurement device 64, memory module 66, and communication device 64 (e.g., of FIG. 44B) may all be incorporated into a single external device, which may in some cases be sold separately. In some embodiments, the external device may also have other functions, such as providing aspiration and/or injection (negative pressure and/or positive pressure) to a catheter. In other embodiments, the external device may comprise some, but not all of the input 59, power module 72, measurement device 64, memory module 66, and communication device 68. For example, in some embodiments, a communication device 58 (FIG. 44A) may replace the external communication device 68, and may be carried on the aspiration monitoring system 48, while the input 59, power module 72, measurement device 64, memory module 66 (FIG. 44B) are incorporated into a single external device. A number of combinations are possible, as described in more detail herein.

Though aspiration of thrombus has been described in detail, the aspiration monitoring system 48, 62, 78 has utility in any aspiration application wherein heterogeneous media is being aspirated. This may include the aspiration of emboli (including not thrombotic emboli) from ducts, vessels, or cavities of the body, or even from solid or semi-solid portions of the body, including, but not limited to, portions of fat, breasts, and cancerous tissue.

In some embodiments, the aspiration system 2 is be provided to the user as a kit with all or several of the components described, while in other embodiments, only the aspiration monitoring system 48 is provided. Though discussion herein includes embodiments for aspiration of thrombus and blood, the definition of the word "fluid" should be understood throughout to comprise liquids and gases. A pressure transducer of an embodiment of the aspiration monitoring system presented herein may be located at a point along the aspiration lumen or any extension of the aspiration lumen (tubes, connectors, etc.).

In some embodiments, an additional or alternate sensor may be used to monitor flow conditions for the notification of the user, including, but not limited to: a Doppler sensor, an infrared sensor, or a laser flow detection device. In some embodiments, an externally-attached Doppler sensor may be employed. In some embodiments, an infrared sensor or a laser flow detection device may be employed around the extension tubing 10.

Assisted Aspiration

Figure 52:
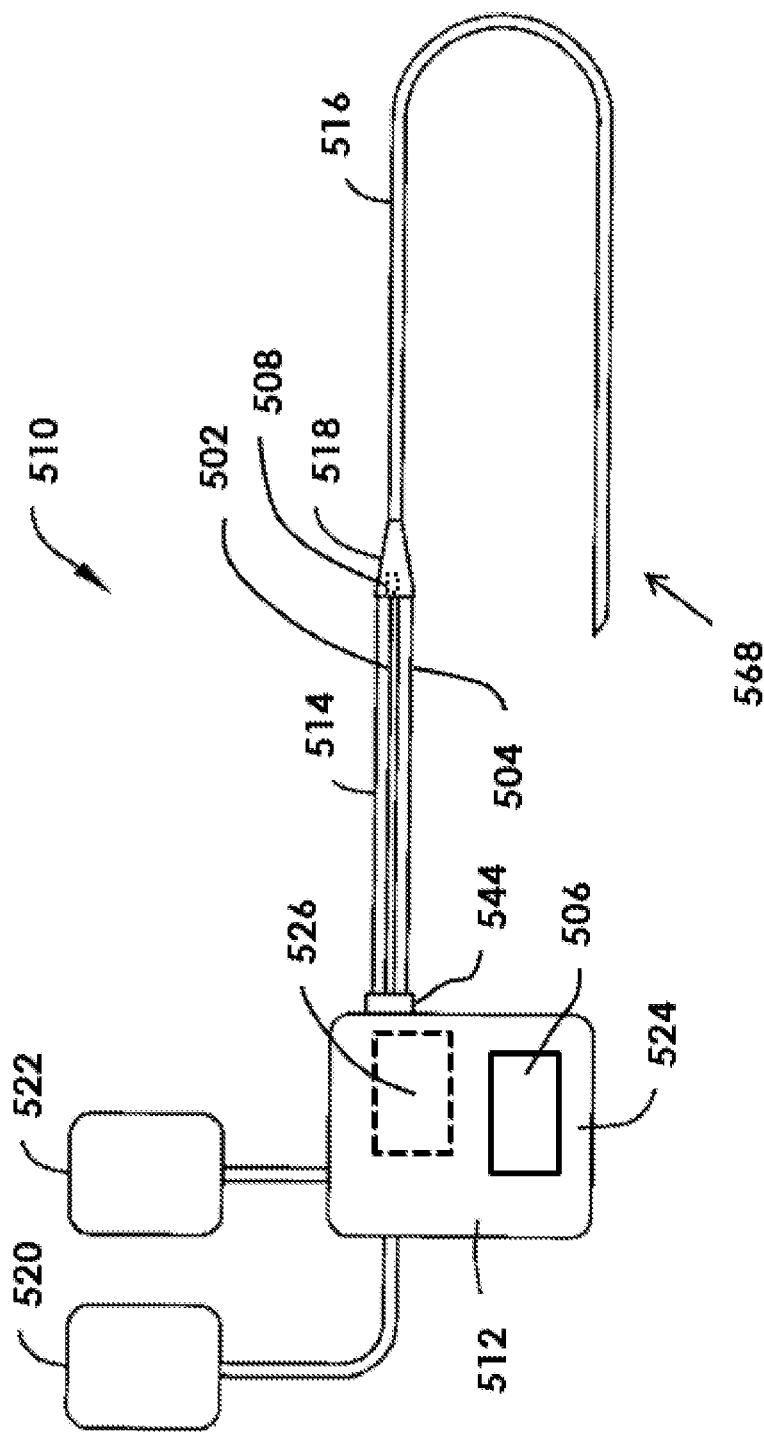
FIG. 52 is a diagrammatic view of a system for aspirating thrombus according to an embodiment of the present disclosure.

FIG. 52 is a diagrammatic figure depicting an assisted aspiration system 510. The aspiration system 510 includes a remote hand piece 512 that contains a fluid pump 526 and an operator control interface 506. In one contemplated embodiment, the system 510 is a single use disposable unit. The aspiration system 510 may also include extension tubing 514, which contains a fluid irrigation lumen 502 and an aspiration lumen 504, and which allows independent manipulation of a catheter 516 without requiring repositioning of the hand piece 512 during a procedure performed with the aspiration system 510. Extension tubing 514 may also act as a pressure accumulator. High pressure fluid flow from the pump 526, which may comprise a displacement pump, pulses with each stroke of the pump 526 creating a sinusoidal pressure map with distinct variations between the peaks and valleys of each sine wave. Extension tubing 514 may be matched to the pump 526 to expand and contract in unison with each pump pulse to reduce the variation in pressure caused by the pump pulses to produce a smooth or smoother fluid flow at tip of catheter 516. Any tubing having suitable compliance characteristics may be used. The extension tubing 514 may be permanently attached to the pump 526 or it may be attached to the pump 526 by a connector 544. The connector 544 is preferably configured to ensure that the extension tubing 514 cannot be attached to the pump 526 incorrectly.

Figure 54:
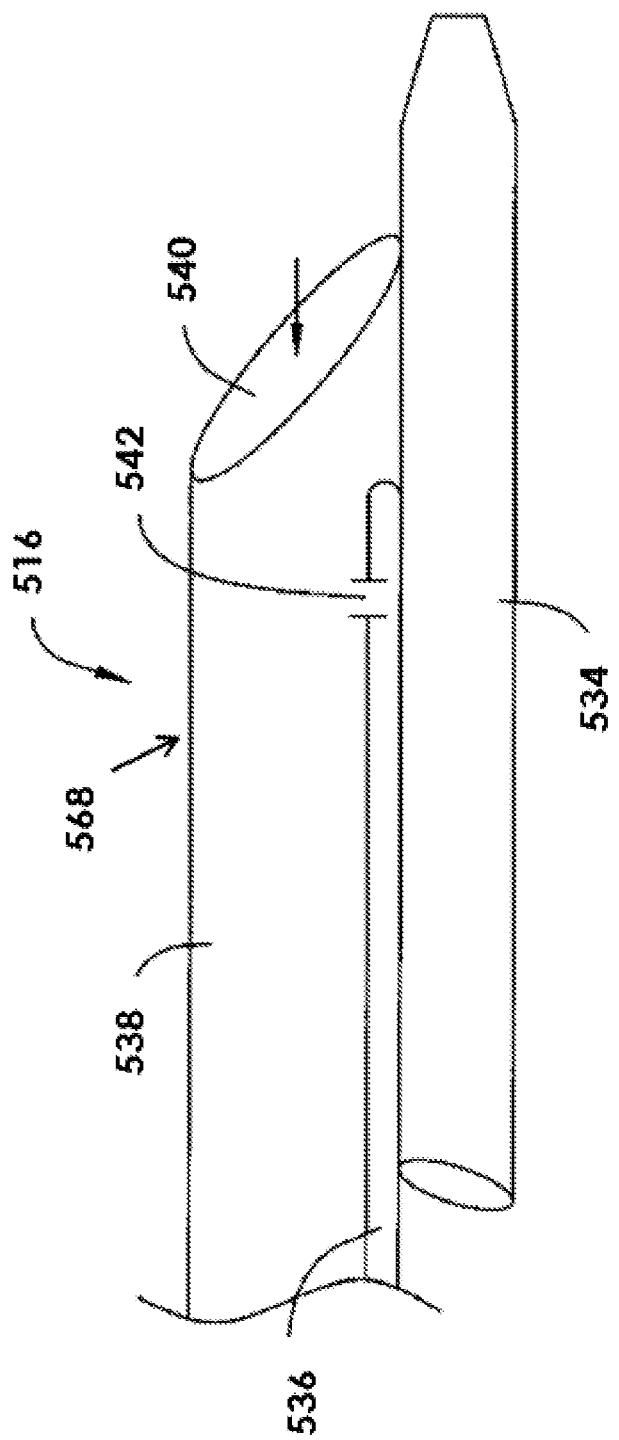
FIG. 54 is a diagrammatic view of the distal end portion of the system for aspirating thrombus of FIG. 52.

An interface connector 518 joins the extension tubing 514 and the catheter 516 together. In one contemplated embodiment, the interface connector 518 may contain a filter assembly 508 between high pressure fluid injection lumen 502 of the extension tubing 514 and a high pressure injection lumen 536 of the catheter 516 (FIG. 54). The catheter 516 and the extension tubing 514 may be permanently joined by the interface connector 518. Alternatively, the interface connector 518 may contain a standardized connection so that a selected catheter 516 may be attached to the extension tubing 514. In some embodiments, the filter assembly 508 may be removably coupled to the extension tubing 514 by a quick disconnect connection.

Attached to the hand piece 512 are a fluid source 520 and a vacuum source 522. A standard hospital saline bag may be used as fluid source 520; such bags are readily available to the physician and provide the necessary volume to perform the procedure. Vacuum bottles may provide the vacuum source 522 or the vacuum source 522 may be provided by a syringe, a vacuum pump or other suitable vacuum source. The filter assembly 508 serves to filter particulate from the fluid source 520 to avoid clogging of the high pressure injection lumen 536 and an orifice 542 (FIG. 54). As described herein, distal sections of the high pressure injection lumen 536 may be configured with small inner diameters, and to the filter assembly 508 serves to protect their continuing function. By incorporating one of a variety of catheters 516 into the assisted aspiration system 510, for example with varying lumen configurations (inner diameter, length, etc.), a variety of aspiration qualities (aspiration rate, jet velocity, jet pressure) may be applied in one or more patients. These aspiration qualities can be further achieved by adjustment of the pump 526, to modify pump characteristics (flow rate, pump pressure). In some embodiments, the catheter 516 may be used manually, for example, without the pump 526, and controlled by hand injection. The manual use of the catheter 516 may be appropriate for certain patient conditions, and may serve to reduce the cost of the procedure.

In one contemplated embodiment, the catheter 516 has a variable stiffness ranging from stiffer at the proximal end to more flexible at the distal end. The variation in the stiffness of the catheter 516 may be achieved with a single tube with no radial bonds between two adjacent tubing pieces. For example, the shaft of the catheter 516 may be made from a single length of metal tube that has a spiral cut down the length of the tube to provide shaft flexibility. Variable stiffness may be created by varying the pitch of the spiral cut through different lengths of the metal tube. For example, the pitch of the spiral cut may be lower (where the turns of the spiral cut are closer together) at the distal end of the device to provide greater flexibility. Conversely, the pitch of the spiral cut at the proximal end may be greater (where the turns of the spiral cut are further apart) to provide increased stiffness. A single jacket covers the length of the metal tube to provide for a vacuum tight catheter shaft. Other features of catheter 516 are described with reference to FIG. 54, below.

Figure 53:
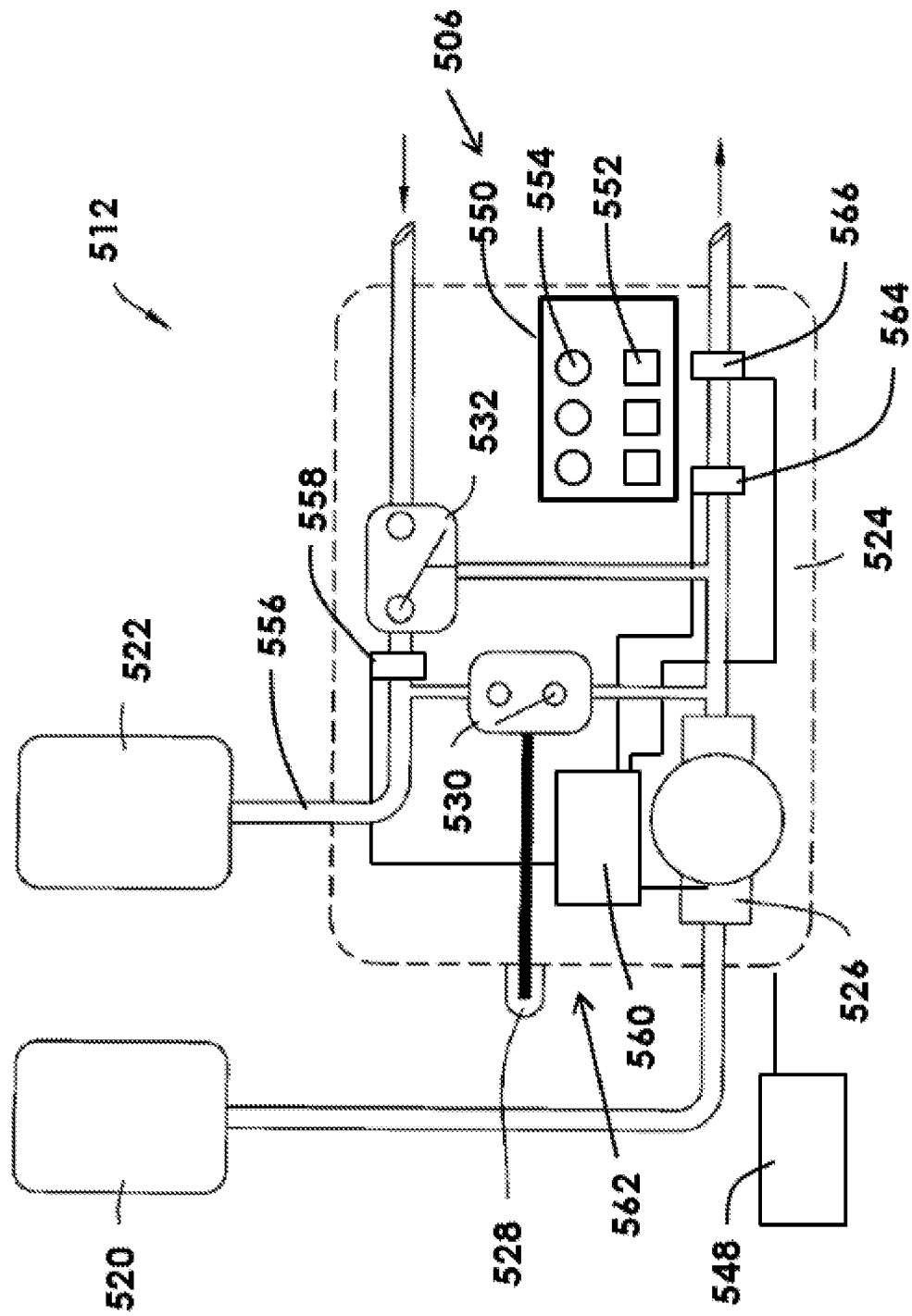
FIG. 53 is a diagrammatic view showing more detail of the proximal portion of the system for aspirating thrombus of FIG. 52.

FIG. 53 is a diagrammatic view showing more detail of the hand piece 512 and the proximal portion of assisted catheter aspiration system 510. The hand piece 512 includes a control box 524 where the power and control systems are disposed. The pump 526 may be a motor driven displacement pump that has a constant output. This pump displacement to catheter volume, along with the location of the orifice 542 (exit) of the catheter high pressure lumen 536 within the aspiration lumen 538 (FIG. 54), ensures that no energy is transferred to the patient from the saline pump as all pressurized fluid is evacuated by the aspiration lumen. A prime button 528 is mechanically connected to a prime valve 530. When preparing the device for use, it is advantageous to evacuate all air from the pressurized fluid system to reduce the possibility of air embolization. By depressing the prime button 528, the user connects the fluid source 520 to the vacuum source 522 via the pump 526. This forcefully pulls fluid (for example 0.9% NaCl solution, or "saline", no "normal saline", or heparinized saline) through the entire pump system, removing all air and positively priming the system for safe operation. A pressure/vacuum valve 532 is used to turn the vacuum on and off synchronously with the fluid pressure system. One contemplated valve 532 is a ported one-way valve. Such a valve is advantageous with respect to manual or electronic valve systems because it acts as a tamper proof safety feature by mechanically and automatically combining the operations of the two primary systems. By having pressure/vacuum valve 532, the possibility of turning the vacuum on without activating the fluid system is eliminated.

The operator control interface 506 is powered by a power system 548 (such as a battery or an electrical line), and may comprise an electronic control board 550, which may be operated by a user by use of one or more switches 552 and one or more indicator lamps 554. The control board 550 also monitors and controls several device safety functions, which include over pressure and air bubble detection and vacuum charge. A pressure sensor 564 monitors pressure, and senses the presence of air bubbles. Alternatively, an optical device 566 may be used to sense air bubbles. In one contemplated embodiment, the pump pressure is proportional to the electric current needed to produce that pressure. Consequently, if the electric current required by pump 526 exceeds a preset limit, the control board will disable the pump by cutting power to it. Air bubble detection may also be monitored by monitoring the electrical current required to drive the pump at any particular moment. In order for a displacement pump 526 to reach high fluid pressures, there should be little or no air (which is highly compressible) present in the pump 526 or connecting system (including the catheter 516 and the extension tubing 514). The fluid volume is small enough that any air in the system will result in no pressure being generated at the pump head. The control board monitors the pump current for any abrupt downward change that may indicate that air has entered the system. If the rate of drop is faster than a preset limit, the control board will disable the pump by cutting power to it until the problem is corrected. Likewise, a block in the high pressure lumen 536, which may be due to the entry of organized or fibrous thrombus, or a solid embolus, may be detected by monitoring the electrical current running the pump 526. In normal use, the current fluxuations of the pump 526 are relatively high. For example, the pump may be configured so that there is a variation of 200 milliAmps or greater in the current during normal operation, so that when current fluxuations drop below 200 milliAmps, air is identified, and the system shuts down. Alternatively, current fluxuations in the range of, for example, 50 milliAmps to 75 milliAmps may be used to identify that air is in the system. Additionally, an increase in the current or current fluxuations may indicate the presence of clot or thrombus within the high pressure lumen 536. For example, a current of greater than 600 milliAmps may indicate that thrombus it partially or completely blocking the high pressure lumen 536, or even the aspiration lumen 538.

A vacuum line 556, connected to the vacuum source 522, may be connected to a negative pressure sensor 558. If the vacuum of the vacuum source 522 is low or if a leak is detected in the vacuum line 556, the control board 550 disables the pump 526 until the problem is corrected. The negative pressure sensor 558 may also be part of a safety circuit 560 that will not allow the pump 526 to run if a vacuum is not present. Thereby a comprehensive safety system 562, including the safety circuit 560, the pressure sensor 564 and/or the optical device 566, and the negative pressure sensor 558, requires both pump pressure and vacuum pressure for the system to run. If a problem exists (for example, if there is either a unacceptably low pump pressure or an absence of significant vacuum), the control board 550 will not allow the user to operate the aspiration system 510 until all problems are corrected. This will keep air from being injected into a patient, and will assure that the aspiration system 510 is not operated at incorrect parameters.

FIG. 54 is a diagrammatic view of the distal end portion 568 of the assisted catheter aspiration system 510, showing more details of the catheter 516. The catheter 516 is a single-operator exchange catheter and includes a short guidewire lumen 534 attached to the distal end of the device. The guidewire lumen 534 can be between about 1 and about 30 cm in length, or between about 5 and about 25 cm in length, or between about 5 and about 20 cm in length, or approximately 13.5 cm in length. An aspiration lumen 538 includes a distal opening 540 which allows a vacuum (for example, from vacuum source 522) to draw thrombotic material into the aspiration lumen 538. A high pressure lumen 536 includes a distal orifice 542 that is set proximally of distal opening 540 by a set amount. For example, distal orifice 42 can be set proximally of distal opening 540 by about 0.0508 cm (0.020 inches), or by 0.0508 cm±0.00762 cm (0.020 inches±0.003 inches) or by another desired amount. The orifice 542 is configured to spray across the aspiration lumen to macerate and/or dilute the thrombotic material for transport to vacuum source 522, for example, by lowering the effective viscosity of the thrombotic material. The axial placement of the fluid orifice 542 is such that the spray pattern interaction with the opposing lumen wall preferably produces a spray mist and not a swirl pattern that could force embolic material out from the distal opening 540. The system may be configured so that the irrigation fluid leaves the pump at a pressure of between about 3,447,378 pascal (500 psi) and about 10,342,135 pascal (1500 psi). In some embodiments, after a pressure head loss along the high pressure lumen 536, the irrigation fluid leaves orifice 542 at between about 4,136,854 pascal (600 psi) and about 8,273,708 pascal (1200 psi), or between about 4,481,592 pascal (650 psi) and about 5,860,543 pascal (850 psi). In some cases, it may be possible (and even desired) to use the assisted catheter aspiration system 510 without operating the pump 526, and thus use the catheter 516 while providing, for example, a hand saline injection via a syringe. Or, in some cases, the assisted catheter aspiration system 510 may be used without the pump 526 attached, with the saline injections done by hand using a syringe through the high pressure lumen 536. If a clog occurs, the syringe may be removed and the pump 526 attached and initiated, for example, for the purpose of unclogging the high pressure lumen 536.

When normal blood flow is achieved after unblocking occlusions or blockages from atherosclerotic lesions and/or thrombosis, there is sometimes a risk of reperfusion injury. This may be particularly significant following thrombectomy of vessels feeding the brain for treatment of thromboembolic stroke, or following thrombectomy of coronary vessels feeding the myocardium. In the case of the revascularization of myocardium following a coronary intervention (e.g. thrombectomy). Reperfusion injury and microvascular dysfunction may be mechanisms that limit significant or full recovery of revascularized myocardium. The sudden reperfusion of a section of myocardium that had previously been underperfused may trigger a range of physiological processes that stun or damage the myocardium. Distal coronary emboli, such as small portions of thrombus, platelets and atheroma, may also play a part. Controlled preconditioning of the myocardium at risk has been proposed to limit the effect of reperfusion injury and microvascular dysfunction. The embodiments of the thrombectomy systems 100, 300 presented herein may be combined with additional features aimed at allowing flow control, in order to limit the potential dangers due to reperfusion following thrombectomy.

FIGS. 55A and 55B illustrate a thrombectomy system 600 comprising a catheter 606 and a guiding catheter 608. The catheter 606 may be an aspiration or thrombectomy catheter as previously described, and may or may not comprise a proximal sealing member. Alternatively, the catheter 606 may be used for partial or complete occlusion of the blood vessel distal of the guiding catheter 608. One purpose for this use is for flow control, as described above, wherein the distal tube 614 or another portion of the catheter 606 may be expanded to partially or completely occlude a blood vessel for a period of time. The catheter 606 may be a combination of an aspiration catheter and a catheter for flow control or occlusion. For example, the distal end of the distal tube 614 may provide some flow control in relation to the blood vessel wall, and the proximal end of the distal tube 614 may provide engagement with the guiding catheter. The guiding catheter 608 may, for example, have an outer diameter of 6 French, an inner lumen diameter of approximately 0.183 cm (0.072 inches), and have a total length of approximately 100 cm. The catheter 606 is configured to be placed through the inner lumen of the guiding catheter 608. The guiding catheter 608 may comprise a composite extruded and braided tubular structure, which has sufficient flexibility and pushability to reach a target area. The guiding catheter 608 may also have a pre-shaped tip. For example, the tip shape may aid in cannulating coronary arteries. The catheter 606 comprises a distal tube 614 which is configured to be extendable out of the inner lumen of the guiding catheter 608, such that a distal end 616 of the distal tube 614 can be advanced a desired length into the blood vessel so that it can be placed adjacent the target area. The proximal end 618 of the distal tube 614 is configured to remain within the inner lumen of the guiding catheter 608, for example, at a region near the distal end of the guiding catheter 608. In some embodiments, the catheter 606 includes a radiopaque marker, which may comprise a band secured to the thrombectomy catheter, and made from radiodense material, such as platinum, gold, or other similar materials. In some embodiments, the distal tube 614 may be formed of polymeric materials containing radiopaque material, such as titanium dioxide (TiO2).

The distal tube 614 comprises a tubular braided member whose diameter increases as the distal tube is made shorter (the distal end 616 and proximal end 618 are brought toward one another) and whose diameter decreases as the distal tube is made longer (the distal end 616 and proximal end 618 are moved away from one another). A tubular member of this type is sometimes referred to as a "Chinese finger trap." A stretchable material (such as silicone or urethane) may be used in some embodiments to fill in the spaces between the woven filaments in order to make a water-tight wall. As in certain other embodiments presented herein, a support member 626 is attached to the proximal end 618 of the distal tube 614 and is used to track the catheter 606 through the guiding catheter 608 and through the vasculature. A push/pull member 605 is attached to the distal end 616 of the distal tube 614 and, like the support member 626, extends proximally, and out of the proximal end of the guiding catheter 608 for access by a user. The support member 626 and the push/pull member 605 each have sufficient tensile strength and sufficient column strength such that each can be pushed and/or pulled accordingly, to cause the distal tube 614 to shorten or lengthen in length, thus changing its diameter. The support member 626 and the push/pull member 605 are each also lockable in relation to each other at their proximal ends, for example, just proximal to the proximal end of the guiding catheter, such that they are no longer able to longitudinally move independent of each other. This locks the distal tube 614 in its particular condition (diameter and length). The catheter 606 may be manipulated by the user so that support member 626 is pulled while the push/pull member 605 is pushed, thus elongating the distal tube 614 while decreasing its diameter (FIG. 55B). In this configuration, the distal tube 614 can be easily inserted through the guiding catheter 608. Once in a desired location within the vasculature, the catheter 606 may be manipulated by the user so that support member 626 is pushed while the push/pull member 605 is pulled, thus shortening the distal tube 614 while increasing its diameter (FIG. 55A). If this is done while the proximal end 618 of the distal tube 614 is within the distal tip of the inner lumen of the guiding catheter 608, an extended lumen may be made, which includes the lumen of the distal tube 614 and the inner lumen of the guiding catheter 608. If the proximal end 618 of the distal tube 614 has a ring of fill or coating material around its outer surface, for example, a stretchable material such as silicone or urethane, a seal may be created between the outer diameter of the distal tube 614 and the inner diameter of the guiding catheter 608. This is appropriate for an aspiration catheter mode. If flow control is desired, the distal tube 614 may be shortened and expanded in the same manner to that it engages the wall of the blood vessel at a desired location. In some embodiments, the push/pull member 605 and/or the support member 626 are constructed from hypo tubing, including but not limited to stainless steel hypo tubing or nitinol hypo tubing.

FIGS. 56A-56C show how the size of the distal tube 614 may be manipulated to reach different specific diameters. Longitudinally-displaced markings 677*a*, 677*b*, 677*c*, 679 or detents on the proximal ends 649, 651 of the support member 626 and/or the push/pull member 605, respectively, may indicate particular corresponding sizes (diameters or lengths) of the distal tube 614. For example, in FIG. 56A, an approximately 5 French diameter configuration of the distal tube 614 may be used for delivering it through the guiding catheter 608. In FIG. 56B, an approximately 6 French diameter configuration of the distal tube 614 may be used when it is tracked through the vasculature, for example, near a lesion site or target site. In FIG. 56C, an approximately 7 French diameter configuration of the distal tube 614 may be used when it is expanded towards or against the wall of a blood vessel. One or more loops 675 are configured to maintain the distance between the support member 626 and the push/pull member 605 in the radial direction (in relation to the distal tube 614). In some embodiments, the one or more loops 675 may be located near the proximal end 618 of the distal tube 614. FIGS. 56A-56C also show how in some embodiments, the push/pull member 605 may be constructed of flat wire. The support member 626 may also be constructed of flat wire.

Figure 57:
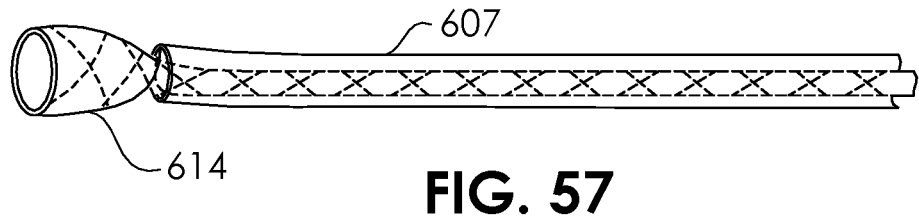
FIG. 57 is a perspective view of an aspiration catheter according to an embodiment of the present disclosure.
Figure 59:
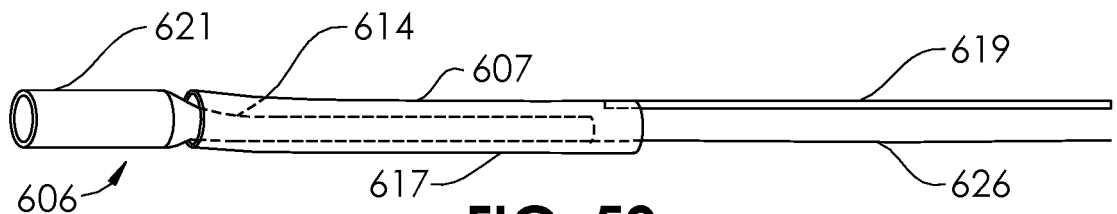
FIG. 59 is a perspective view of an aspiration catheter according to an embodiment of the present disclosure.

FIG. 57 shows an additional sleeve 607 which may be placed over the distal tube 614 to further constrain its diameter for delivery through the guiding catheter 608 and/or the vasculature. The sleeve 607 may extend proximally and out the proximal end of the guiding cateteter 608 so that it can be pulled off in a proximal direction to allow the distal sleeve 614 to expand. The sleeve 607 may be used in addition to the push/pull member 605, or may be used in lieu of the push/pull member 605 and its utility in relation to the support member 626. In an alternative embodiment seen in FIG. 59, the sleeve 607 may comprise an elongate distal tube 617 which is coupled to a proximal wire or pusher member 619, this allowing a user to handle both the proximal wire 619 of the sleeve 607 and the support member 626 of the catheter 606 while removing the sleeve 607 from the patient. This would aid in holding the distal tube 614 at its desired location in the vasculature (and/or in the guiding catheter 608) while removing the sleeve 607. A portion 621 of the distal tube 614 which may remain distal of the sleeve 607 may comprise a non-expandable section.

Figure 58:
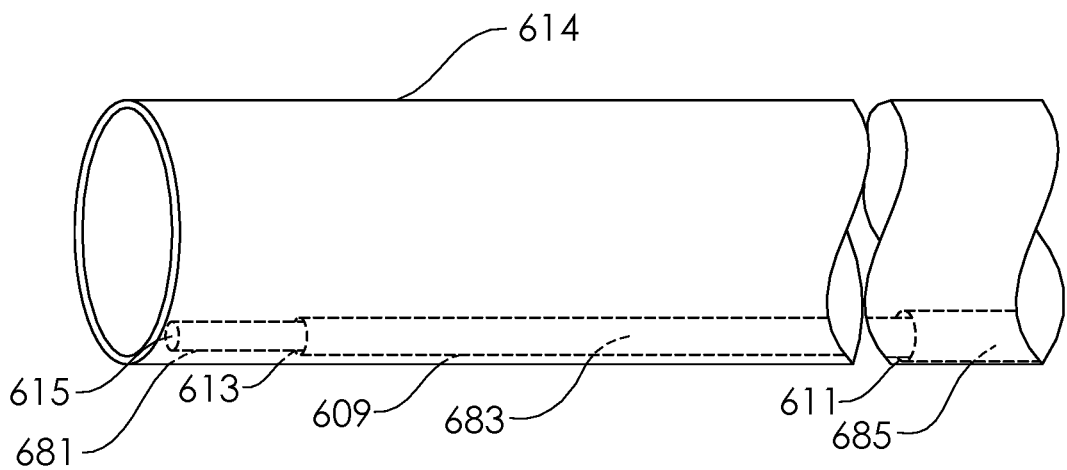
FIG. 58 is a perspective view of a thrombectomy catheter according to an embodiment of the present disclosure.
Figure 64:
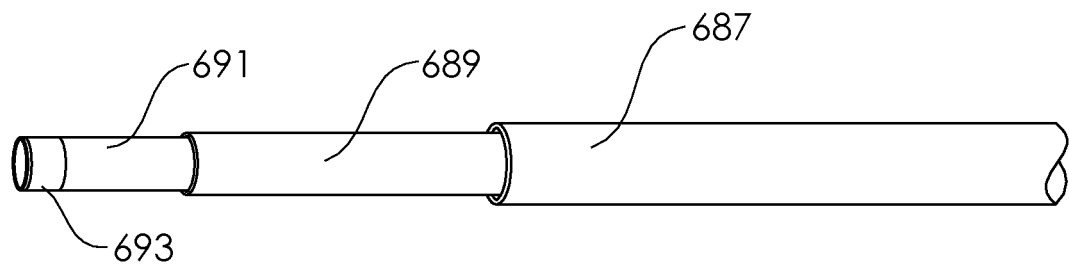
FIG. 64 is a perspective view of a component of an aspiration catheter according to an to an embodiment of the present disclosure.

FIG. 58 illustrates a thrombectomy catheter which may share certain elements of the embodiments of FIGS. 29-42. In this particular embodiment, a high pressure saline injection lumen 609 comprises two or more sections. As depicted, the injection lumen 609 includes a proximal portion 685, a middle portion 683 and a distal portion 681. The middle portion 683 is configured to telescope within the proximal portion 685 and the distal portion 681 is configured to telescope within the middle portion 683. Each portion may be constructed from precision tubing or hypo tubing, such as polyimide or nitinol, such that the difference in diameter between the opposing outer diameter and inner diameter of two neighboring tubes is very small, in order to create a capillary seal between the two. For example, in some embodiments the difference in diameters may be about 0.002 cm (0.0008 inches) or less, or in some embodiments about 0.001 cm (0.0004 inches) or less, or in some embodiments about 0.0005 cm (0.0002 inches) or less. This allows a section of injection lumen 609 that has a variable length, while being dynamically sealed, thus minimizing or eliminating any leakage at telescope points 611, 613, and allowing all or the vast majority of the injected saline to exit at exit port 615. In some embodiments, the capillary seal should be liquid tight, or water tight (saline tight), and in some embodiments need not be air tight (gas tight). A progressively smaller inner diameter from the proximal portion 685 to the distal portion 681 helps to maintain a high pressure jet at the exit port 615 (maximum pressure), without requiring too large of a pump head pressure. During delivery (tracking) of the catheter, a stylet may be placed within the injection lumen 609 in order to add stiffness, improve transition flexibility and protect the telescope points 611, 613 from damage. The stylet may be removed once the catheter is tracked to its desired location, and prior to the injection of saline and the aspiration of thrombus. In some embodiments, the proximal portion 685 may have an outer diameter of between about 0.0508 cm (0.020 inches) and 0.0732 cm (0.030 inches) or about 0.066 cm (0.026 inches). In some embodiments, the middle portion 683 may have an outer diameter of between about 0.0305 cm (0.012 inches) and 0.0559 cm (0.022 inches) or about 0.0406 cm (0.016 inches). In some embodiments, the distal portion 681 may have an outer diameter of between about 0.020 cm (0.008 inches) and 0.0406 cm (0.016 inches) or about 0.0305 cm (0.012 inches). In some embodiments, the proximal portion 685 may have an inner diameter of about 0.559 cm (0.022 inches), the middle portion 683 may have an inner diameter of about 0.0483 cm (0.019 inches), and the distal portion 681 may have an inner diameter of about 0.028 cm (0.011 inches). In the distal portion 681, an inner diameter of between about 0.0229 cm (0.009 inches) and about 0.0381 cm (0.015 inches) optimizes the delivery volume, while minimizing the outer diameter of the distal portion 681, thus maintaining the largest possible aspiration lumen cross-sectional area. In some embodiments, the distal tube 614 is a Chinese finger trap (braided tubular member) as previously described, and thus, the telescoping of the injection lumen 609 tubes allows the length change of the distal tube 614 freely. In this embodiment or any of the embodiments herein, the distal tube 614 may comprise a bumper of softer material at the distal end to add atraumatic characteristics. In alternative embodiments which do not require the telescoping of the injection lumen 609, the multiple layers of different diameter tubes may still be used in order to create a transition from larger diameter to smaller diameter and from stiffer to more flexible moving from the proximal end to the distal end. The tube sections may in this case be adhesively, epoxy or heat bonded together, or may be friction fit. FIG. 64 illustrates possible dimensions and assembly of an embodiment. The proximal portion 687 may comprise 0.066 cm×0.048 cm (0.026 inches×0.019 inches) stainless steel hypo tubing, for example, 304 series stainless steel. The middle portion 689 may comprise 0.066 cm×0.048 cm (0.016 inches×0.013 inches) nitinol tubing. The distal portion 691 may comprise polymeric tubing having a proximal outer diameter of about 0.028 cm (0.011 inches) tapering down distally to an outer diameter of about 0.028 cm (0.011 inches). A radiopaque marker band 693 may be carried on the distal portion having the 0.028 cm (0.011 inches) outer diameter. In some embodiments the high pressure injection lumen 609 may be secured to the inner wall of the distal tube 614, so that it will not severely flex or kink, and thus interfere with passage of a guidewire 28, 134 or cause a pinch or clog in the high pressure injection lumen 609. The high pressure injection lumen 609 may be secured with adhesive or other equivalent techniques.

Figure 60:
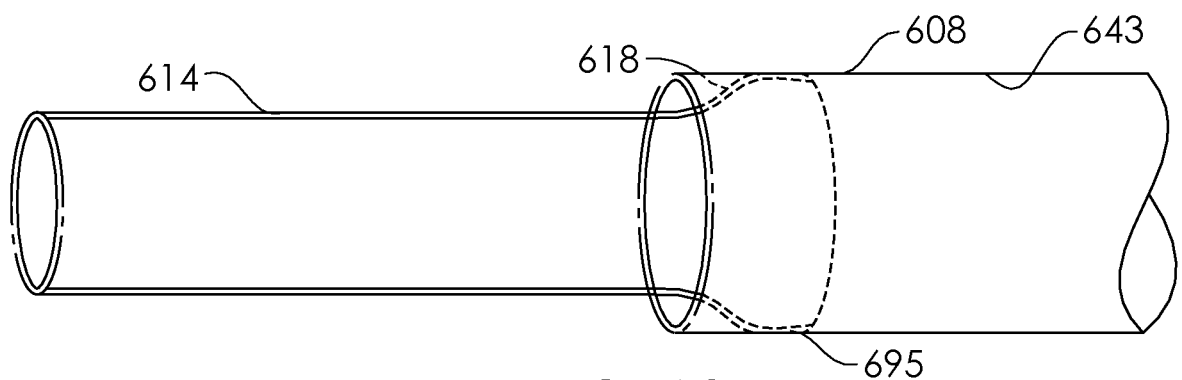
FIG. 60 is a perspective view of an aspiration system according to an embodiment of the present disclosure.

FIG. 60 illustrates the proximal end 618 of an embodiment of the distal tube 614 of the catheter 606 having an expanding structure 695 which seals against the inner diameter 643 of the guiding catheter 608. This may seal via the size of its formed diameter or it may be expandable by the user, for example, by using the combination of the support member 626 and the push/pull member 605 described herein.

Figure 61A:
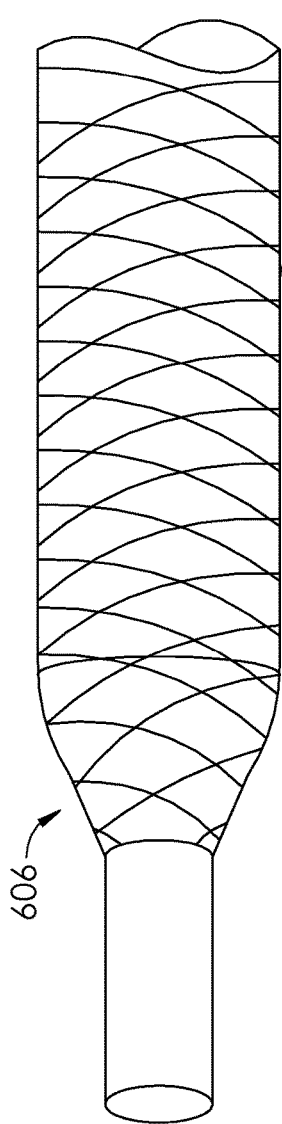
FIGS. 61A-61C are perspective views of an aspiration system according to an embodiment of the present disclosure in multiple configurations.
Figure 61B:
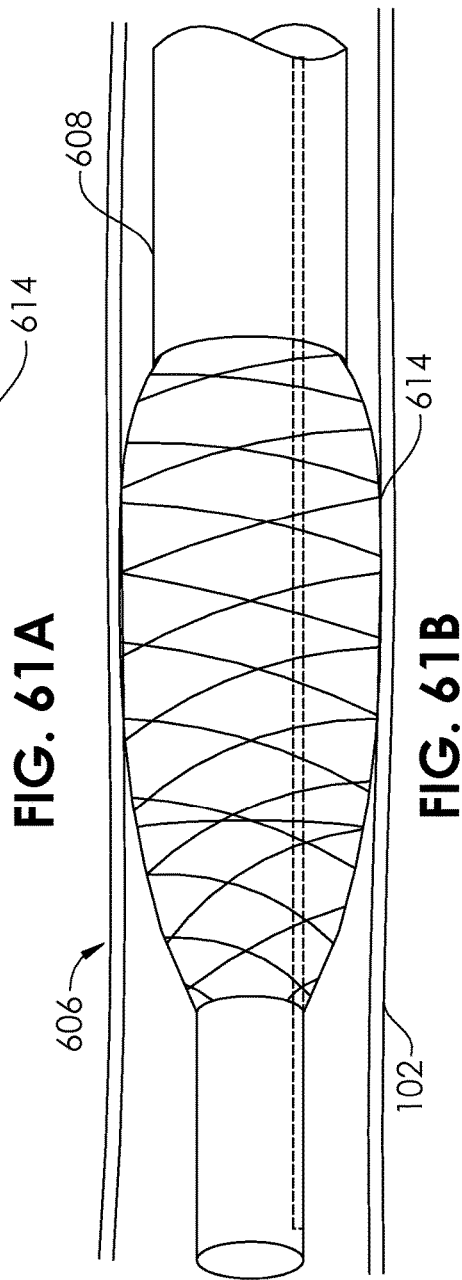
Figure 61C:
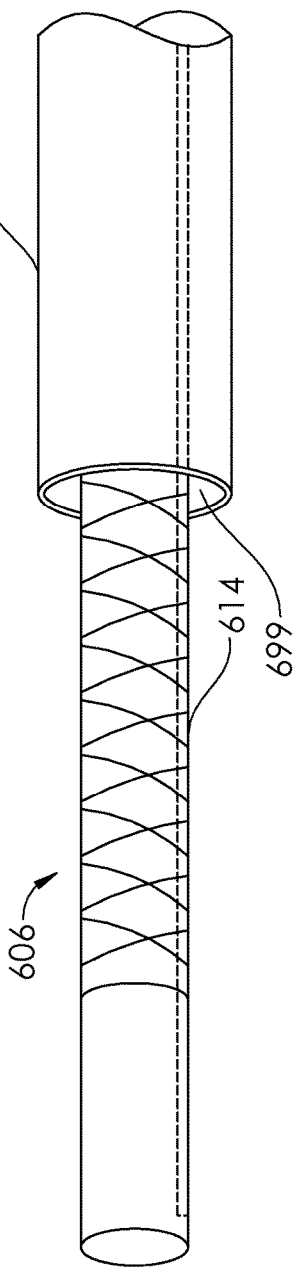

FIGS. 61A-61C illustrate the flow control mode of the catheter 606 for approaching and/or sealing against the blood vessel wall. In some embodiments, the distal tube 614 may include a portion that has a diameter that is less than the blood vessel diameter. In these embodiments, the push/pull member 605 may be pulled and the support member 626 pushed in order to deliver the distal tube 614 against the vessel wall (while the diameter is increased and the length is shortened). In other embodiments, the distal tube 614 may include a portion that has a diameter that is about the same or larger than the blood vessel diameter. In these embodiments, the push/pull member 605 may be pushed and the support member 626 pulled in order to decrease the diameter (while increasing the length) to allow delivery down the guiding catheter 608 and through the vasculature. FIG. 61B illustrates the distal tube 614 extending from the guiding catheter 608, and expanded to seal against the wall of the blood vessel 102. FIG. 61C illustrates the distal tube 614 in a reduced diameter state configured for placement through the inner lumen 699 of the guiding catheter 608.

Figure 62:
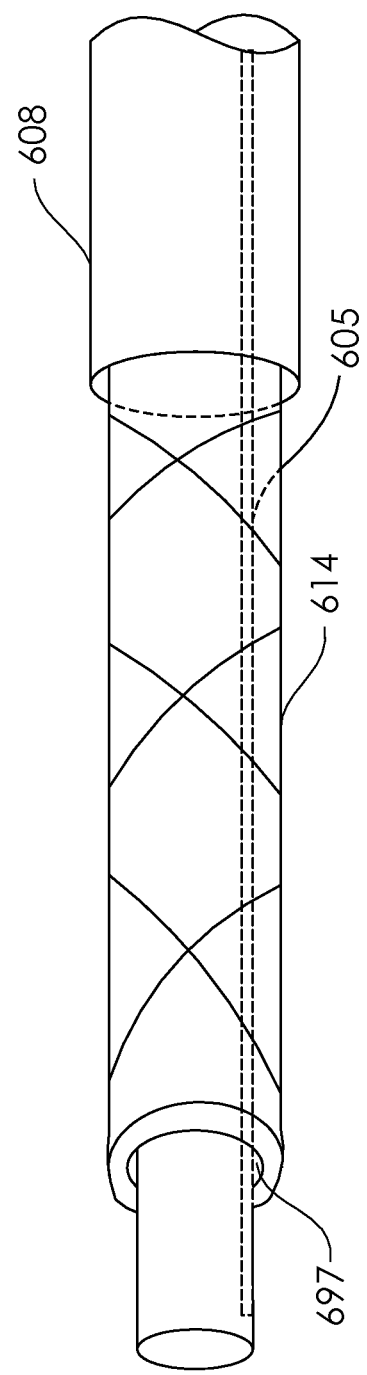
FIG. 62 is a perspective view of an aspiration system according to an embodiment of the present disclosure.

FIG. 62 illustrates an embodiment of the distal tube 614 with the Chinese finger trap in which pulling on the push/pull member 605 causes the distal tube 614 to invert at an inversion point 697. In some embodiments, the inversion may be done partially and may be used to cause an increase in the diameter of the distal tube 614 (for example, to perform flow control in the blood vessel). In some embodiments, the inversion may be done to remove the distal tube 614 from the vasculature and into the guiding catheter 608 or to remove the distal tube from the guiding catheter 608. By pushing on the push/pull member 605, the distal tube 614 may be delivered into a location in the blood vessel.

Figure 63A:
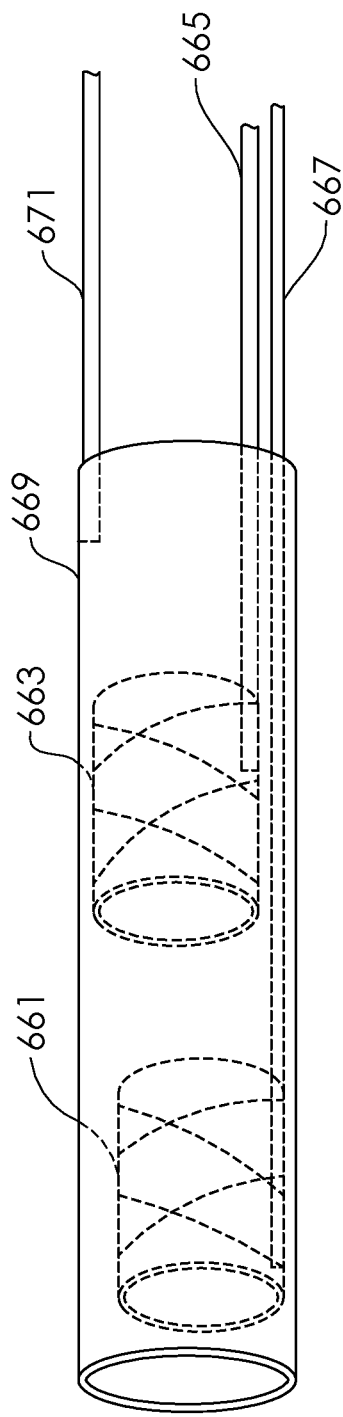
FIGS. 63A-63B are perspective views of an aspiration system according to an embodiment of the present disclosure.
Figure 63B:
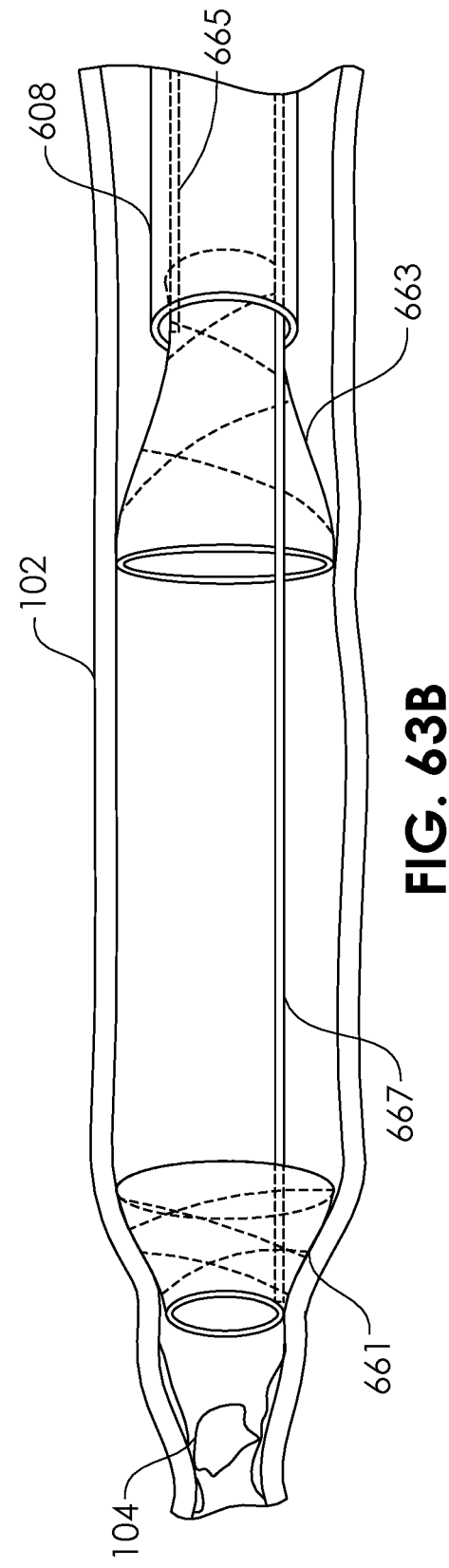

FIGS. 63A-63B illustrate how both flow control and the coupling to the guiding catheter 608 may be achieved using two different catheters, labeled in FIG. 63A as first catheter 661 and second catheter 663. The second catheter 663 (having support member 665) and the first catheter 661 (having support member 667) may each be delivered together within a larger delivery catheter 669 (having support member 671). After delivery through the guiding catheter 608 and to or near a target site (for example a clot/thrombus and/or an atherosclerotic lesion), the delivery catheter 669 is removed by pulling it proximally, and the first catheter 661 is positioned in the blood vessel 102 for flow control, and/or adjacent a thrombus 104, and the second catheter 663 is positioned an a coupling manner to the guiding catheter 608.

Figure 65:
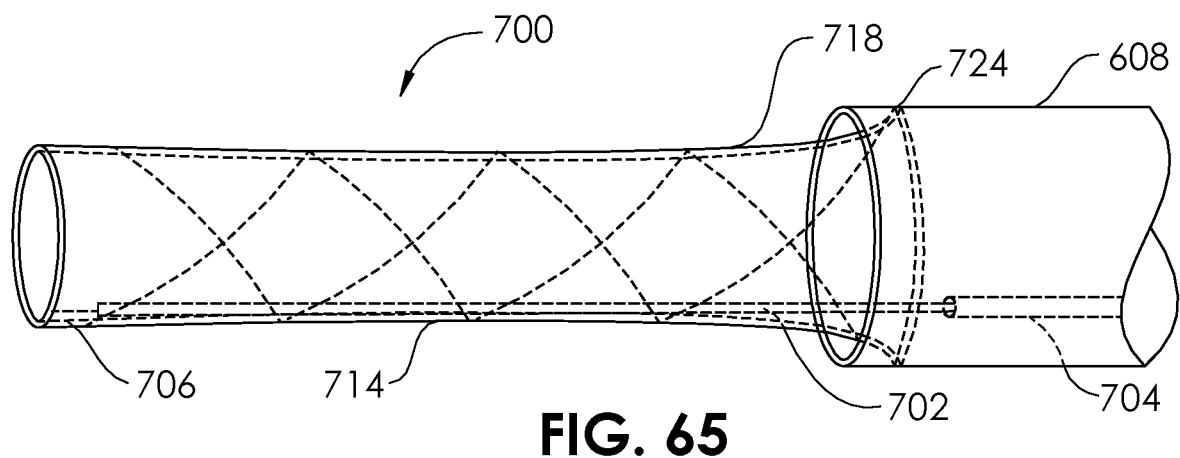
FIG. 65 is a perspective detail view of a portion of an aspiration catheter according to an embodiment of the present disclosure.

FIG. 65 is an embodiment for a catheter 700 which also makes use of a distal tube using the Chinese finger trap braided tubular member 714. In this embodiment, a wire 702, for example a Nitinol wire, is telescopically located within a proximal tube 704. In some embodiments, a length of a more flexible material 706, such as polyimide is attached distal of the wire 702 for a transition of flexibility. The proximal end 718 of the distal tube 714 has a seal section 724 for engaging with the guiding catheter 608. The proximal end of the wire 702 extends proximally of the proximal end of the proximal tube 704. By pushing on the proximal tube 704 and pulling on the wire 702 at each of their respective proximal ends, a user may expand the distal tube 714 for flow control (e.g. blocking or slowing down blood flow that is coming from the right side of FIG. 65 to the left side of FIG. 65). A thrombectomy procedure may be performed through the extended lumen comprising the lumen of the distal tube and the inner lumen of the guiding catheter. Any combination of the embodiments disclosed herein may be used to create a combination flow control and thrombectomy embodiment. The thrombectomy portion may include aspiration only, or may combine aspiration and saline injection.

Figure 66:
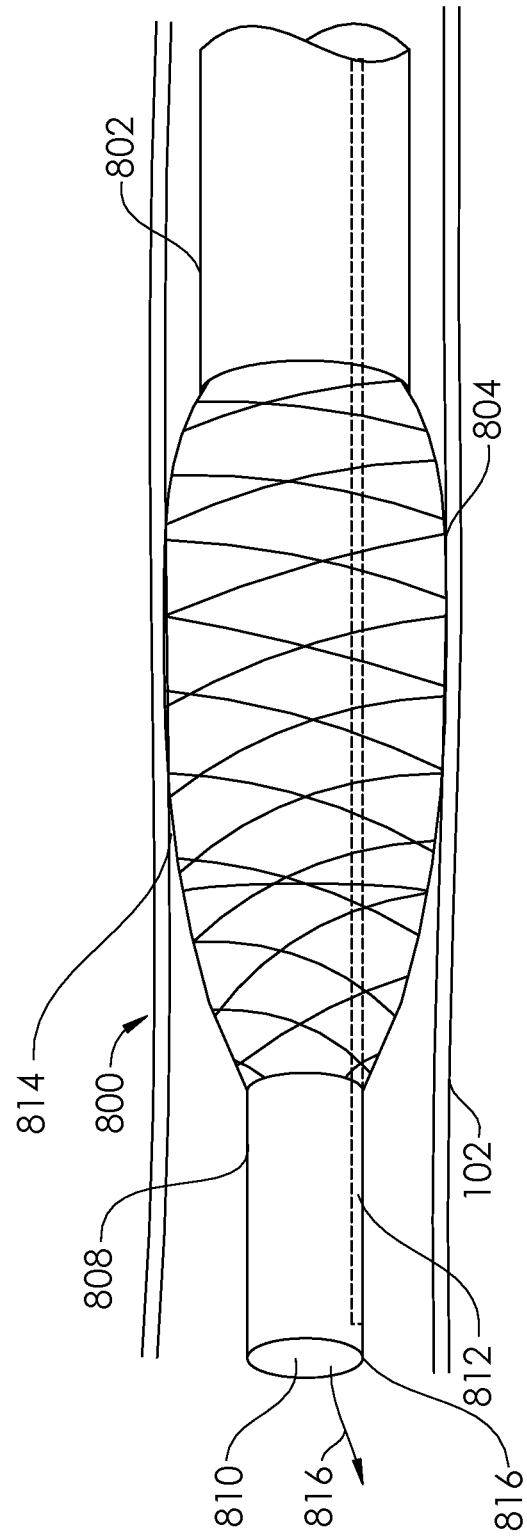
FIG. 66 is a perspective view of a flow control system according to an embodiment of the present disclosure.

FIG. 66 illustrates a system for flow control 800 comprising a guiding catheter 802 for delivery in a blood vessel 102 and a flow control catheter 808 having a self-expandable portion 804. The flow control catheter 808 has a lumen 810 for delivery of a fluid and is pushable and retractable by a support member 812. The support member 812 may comprise wire with a flat or round cross-section, or may comprise tubing, such as hypo tubing, including stainless steel, Nitinol, polyimide, or other materials. The self-expandable portion 804 is configured to create a seal 814 with the blood vessel 102. In some embodiments, a medicant 816 or drug is delivered through the lumen 810 from a proximal end of the flow control catheter 808 to a distal end 816. The seal 814 enables the medicant 816 to be delivered into the blood vessel 102 (for example, into thrombus, atherosclerotic plaque, or into the blood vessel wall) with a relatively high concentration, and the self-expandable portion 804 by means of the seal 814 that limits the amount of blood flow that would otherwise dilute the medicant 816. The seal 814 provided by the self-expandable portion 804 may also in some cases be used to limit the amount of downstream perfusion. This may be helpful in cases in which a stable mechanical environment is desired, such that significant blood flow does not alter the environment in which a procedure is being performed. The control of downstream perfusion may also minimize reperfusion injury by protecting distal tissue from any emboli that may be carried downstream by significant flow, or from the sudden perfusion of oxygen-rich blood in quantities which may create free radicals. Reperfusion injury may result from inflammation or oxidative damage, through the induction of oxidative stress. Though the self-expandable portion 804 may be used to reduce flow or perfusion of the blood vessel 102, in some cases, the self-expandable portion 804 need not entirely block the lumen of the blood vessel 102, thus allowing a controlled, reduced, and tolerable amount of perfusion at the critical period. The self-expandable portion 804 may also provide added support, for example to the guiding catheter 802, and may serve to center the lumen 810 in the blood vessel 102. In certain embodiments, the lumen 810 may comprise one or more lumens, including at least one aspiration lumen. The self-expandable portion 804 may serve to keep the distal end of the aspiration lumen away from the blood vessel wall, and thus prevent damage to the blood vessel wall, and the keep the tip of the lumen 810 from being blocked (e.g., by the blood vessel wall).

In one embodiment, a system for delivery of a medicant or aspiration of blood or thrombus includes a flow control catheter having a proximal end and a distal end and lumen having a proximal end configured for user access external to a patient, and a distal port, a self-expandable member having an expanded state and a constricted state, and configured to be advanceable through the lumen of a guiding catheter in the constricted state, an elongate support member coupled to the distal end of the flow control catheter and configured to apply a distally-directed force to the distal end of the flow control catheter when a compressive load is applied to the elongate support member, wherein the self-expandable member is configured to move towards its expanded state within vasculature of the patient, when the self-expandable member is moved outside of the lumen of the guiding catheter. In some embodiments, the self-expandable member comprises flat wire. In some embodiments, the self-expandable member comprises round wire. In some embodiments, the self-expandable member comprises hypo tubing. In some embodiments, the self-expandable member comprises at least one of the materials selected from the list consisting of stainless steel, Nitinol, and polyimide. In some embodiments, the self-expandable member is a braided tubular construction. In some embodiments, the braided tubular construction is coated with an elastomeric material. In some embodiments, the lumen of the flow control catheter is configured to deliver a medicant. In some embodiments, the self-expandable member is configured to create a seal against an inner wall of a blood vessel.

Figure 67:
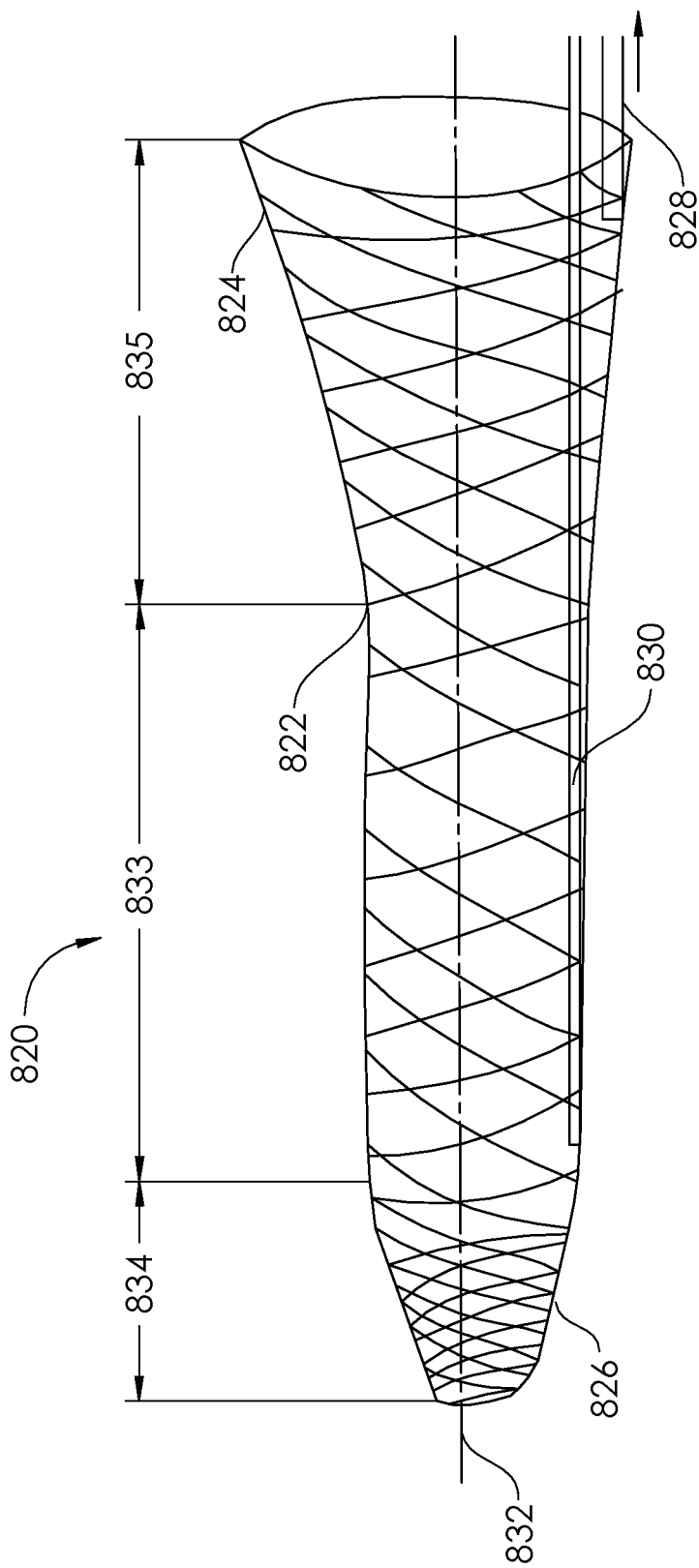
FIG. 67 is a perspective view of a catheter system having a collapsible and expandable distal portion.

FIG. 67 illustrates a catheter 820 having an expandable portion 822 having a proximal end 824 and a distal end 826. The expandable portion 822 may be self-expandable as described in relation to FIG. 66, or may be expandable by use of a support member 828 and a push/pull member 830, as described in relation to FIGS. 56A-56C. Representative dimensions in inches are shown for different sections of the expandable portion 822. The distal end 826 may be twistable and untwistable about a longitudinal axis 832, such that a tapered portion 834 may be created. The tapered portion 834 may have a length of between about one cm and about three cm, or may have a length of about 2 cm. An intermediate portion 833 has a substantially constant expanded diameter, and may have a length of between about two cm and about ten cm, or may have a length of between about three cm and about five cm. A proximal flared portion 835 (in its expanded state) may have a diameter that increases proximally. The proximal flared portion 835 may have a length of between about six cm and about twelve cm. In some embodiments, the intermediate portion 833 and the majority of the tapered portion 834 (in its untwisted state) have substantially the same outer diameter. In one particular embodiment, this outer diameter may be around 0.068 inches (1.7 mm). The tapered portion 834 (in its twisted state) may taper down from around 0.068 inches (1.7 mm) to around 0.032 inches (0.81 mm) to 0.035 inches (0.89 mm). The proximal flared portion 835 may gradually increase to an outer diameter on the order of 0.100 inches (2.5 mm). The proximal flared portion 835 may be collapsible/expandable on its own (without any changes to the tapered portion 834 or intermediate portion 833). For example, the proximal flared portion 835 may be collapsible so that its entire length has an outer diameter of about 0.068 inches (1.7 mm) and expandable so that the outer diameter starts at about 0.068 inches (1.7 mm) and tapers up to about 0.100 inches (2.5 mm). The entire expandable portion 822 may comprise a braided tubular structure and may be coated with an elastomeric material, for example, by a dipping process.

In one embodiment, an expandable catheter includes a proximal end and a distal end and a distal port, an expandable member having an expanded state and a constricted state, and configured to be advanceable through the lumen of a guiding catheter in the constricted state, a first elongate member coupled to the distal end of the expandable member and a second elongate support member coupled to the proximal end of the expandable member, wherein compression applied on the first elongate member coupled with tension applied on the second elongate member moves the expandable member towards its constricted state and tension applied on the first elongate member coupled with compression applied on the second elongate member moves the expandable member towards its expanded state. In some embodiments, the distal portion of the expandable member is configured to be twisted into a shape having a tapered diameter.

Figure 68A:
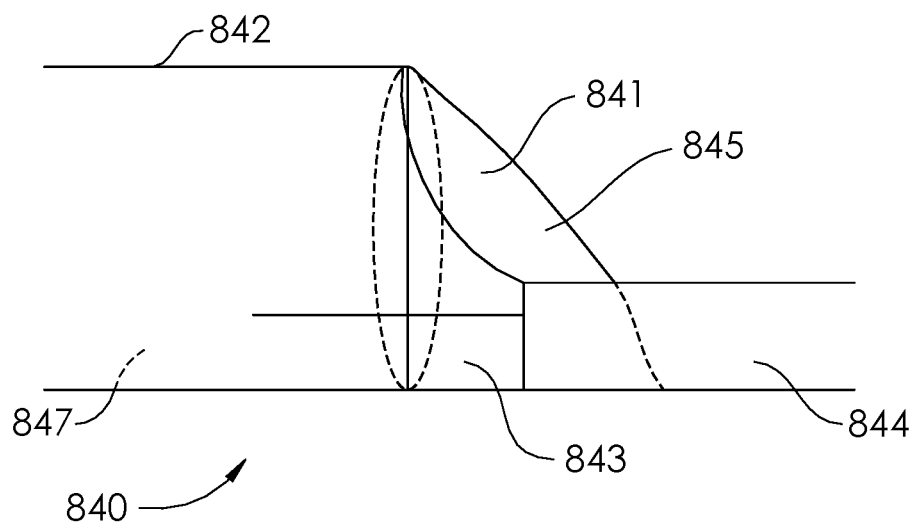
FIG. 68A is a perspective view of a connection between a distal tube and a support member.
Figure 68B:
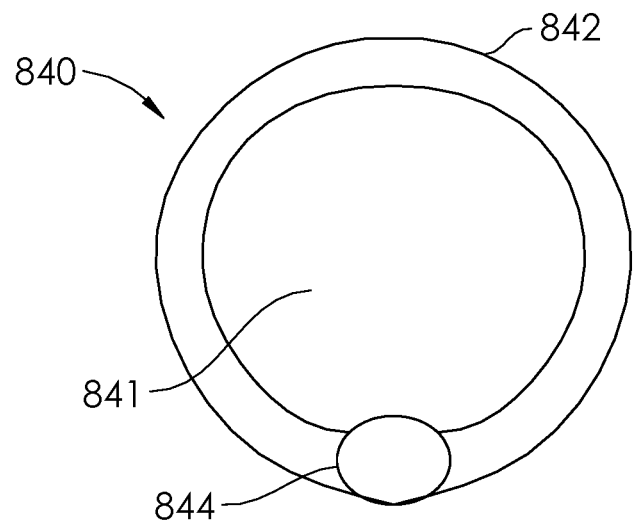
FIG. 68B is a proximal end view of the connection in FIG. 68A.

FIGS. 68A-68B illustrate a connection 840 between a distal tube 842 and a support member 844 which may be utilized in many of the embodiments described herein. The support member 844 transitions to a smaller diameter extension 843. In some embodiments, the smaller diameter extension 843 extends from within an internal lumen 849 of the support member 844, with exterior of the smaller diameter extension 843 bonded to the interior of the support member 844. A skive 845 is angled in relation to a line perpendicular to the longitudinal axis 851, to increase the cross-sectional area of an opening 841 of the lumen 847 of the distal tube 842. In this manner, the flow through the lumen 847 is not significantly restricted by the cross-sections of the support member 844 and the smaller diameter extension 843.

FIG. 69A illustrates a system for forced aspiration 853 including an IV bag 855, a tubing set 857 including a cassette 859 for coupling to a pump 861, and an aspiration catheter 863 having a y-connector 865, a high pressure delivery tube 867, and an expandable aspiration lumen 869. A high pressure lumen 871 of the high pressure delivery tube 867 is shown outputting into a jet 873, which flows into the expandable aspiration lumen 869. The expandable aspiration lumen 869 includes an expandable member 875 which may expand when there is a positive pressure (+P) created by the jet 873 within the expandable aspiration lumen 869, thus increasing the cross-sectional area of the expandable aspiration lumen 869 over a length between the distal end 877 of the expandable aspiration lumen 869 and a point more proximal at which a pressure drop reduces the pressure within the lumen so that the expandable member 875 does not expand. Over this section, the volume of the expanded expandable aspiration lumen 869 is thus increased, allowing for increased flow of the material (thrombus, blood, etc.) being removed. In some cases, a seal 814 may be made against the vessel wall 879 by the expandable member 875, for example to control flow, though this is optional. The diameter of the expandable member 875 when expanded may be selected by a user such that expandable member 875 does or does not seal against the vessel wall 879 when the expandable member 875 is expanded. The expandable member 875 may be formed integrally with a tubular (non-expandable) portion 881 of the aspiration catheter 863, or may be attached by heat fusing, adhesive, epoxy, shrink tubing, or other joining methods.

FIG. 69B illustrates the expandable member 875 when it is not expanded. The wall 885 of the expandable member 875 is configured to be foldable into a two or more wings 883a, 883b, 883c to lower its profile and aid is passage through other devices such as introducer sheaths 897 or guiding catheters and through the vasculature itself. Returning to FIG. 69A, the y-connector 865 includes a first port 887 which is fluidly coupled to the expandable aspiration lumen 869, and a second port 889 which is fluidly coupled to the high pressure lumen 871 of the high pressure delivery tube 867. In some embodiments one or both of the ports 887, 889 comprise luer connectors, such as, for example, female luer lock connectors. The first port 887 is shown coupled to a vacuum source 891. A syringe is shown as the fluid source 891 in FIG. 69A, but a vacuum pump or vacuum bottle may instead be used. An aspiration monitoring system 895 may incorporate any of the aspiration monitoring systems 48, 62, 78 described herein, and shown in FIG. 69A coupled in such a manner that it is configured to sense a pressure within at least a portion of the expandable aspiration lumen 869. An extension tube 893 may be coupled between the vacuum source 891 and the aspiration monitoring system 895. The cassette 859 may include a piston element such that the cassette 859 and the pump 861 act together as a piston pump for pumping high pressure fluid through the high pressure lumen 871 of the high pressure delivery tube 867. A catheter, cassette, and pump system or elements thereof may be utilized such as those disclosed in U.S. Patent Application No. 2015/0327875 to Look et al., published Nov. 19, 2015, which is incorporated herein by reference in its entirety for all purposes.

In an alternative, embodiment, the delivery tube may be used to inject a fluid (saline, drug, etc.) into the lumen of the blood vessel through the distal opening 913 of the expandable aspiration lumen 869. The IV bag 855 may be cooled by a cooling system 915 in order to deliver cooled fluid, which may be used to cool the entire body of the patient (through circulation) or to selectively cool one or more organs or end structures. A drug may also be cooled to temporarily decrease its activity, or to delay its treatment effectiveness. Alternatively, the drug may be warmed to increase or accelerate its activity.

FIG. 70 illustrates mateable connectors 901, 903 which may be used for connection of the tubing set 857 to the port 889, instead of standard luer connectors. Connector 903 is sealingly secured to a rigid tube 905. The rigid tube 905 may comprise stainless steel, and may comprise hypo tubing. The opposite end of the rigid tube 905 may be coupled to flexible tubing. Connector 901 is sealingly secured to tubing 907 and includes a cavity 909 which is sized to allow the free passage of a distal end 911 of the rigid tube 905 when the mateable connectors 901, 903 are secured to each other. An o-ring 917 is configured to seal over the outer diameter 919 of the rigid tube 905. The connector 901 and the connector 903 may include male and female snapping features 921, 923 in order to be able to releasably lock to each other, so that they may reliably maintain the seal between the o-ring 917 and the rigid tube 905. In some embodiments, a single tubing set extending between the connectors 901, 903 and the IV bag 855 (FIG. 69A) includes a connector half, extension tubing, a pump cassette, tubing and a spike (e.g., to the IV bag). The embodiment of FIGS. 69A-70 facilitates several key treatment modalities in ST segment elevation myocardial infarction (STEMI): platelet inhibition, clot removal, bleeding avoidance, stent apposition, and flow control.

In one embodiment, an aspiration system for removal of material from a lumen, cavity or duct of a patient includes an aspiration catheter having a proximal end and a distal end and comprising an expandable aspiration lumen, a high pressure injection lumen extending within the elongate support member and having a proximal end adjacent the proximal end of the aspiration catheter and a distal end adjacent the distal end of the aspiration catheter, at least one orifice located at the distal end of the high pressure injection lumen configured to allow liquid injected through the high pressure injection lumen to be released at or adjacent a distal end of the expandable aspiration lumen. In some embodiments, the expandable aspiration lumen has an expanded state and a non-expanded state, wherein at least some peripheral walls of the aspiration catheter surrounding the expandable aspiration lumen have a folded shape.

Although several embodiments have been presented for breaking up or removing thrombus, general aspiration (with or without high pressure saline injection) of normal blood, or other liquids or deposits within the blood vessels, ducts or other tubular or non-tubular cavities of the body is contemplated as being within the scope of the embodiments of the present disclosure.

Any of the embodiments described herein may utilize the thrombectomy cathteters and pumps described in U.S. Patent Application No. 2007/0073233 to Thor et al. ("Thor") published Mar. 29, 2007, which is incorporated herein by reference in its entirety for all purposes.

Any of the embodiments described herein may utilize the thrombectomy catheters described in U.S. Patent Application No. 2001/0051811 to Bonnette et al. ("Bonnette") published Dec. 13, 2001, which is incorporated herein by reference in its entirety for all purposes.

Any of the embodiments described herein may utilize the aspiration catheter and separator described in U.S. Patent Application No. 2014/0155931 to Bose et al. ("Bose") published Jun. 5, 2014, which is incorporated herein by reference in its entirety for all purposes.

Any of the embodiments described herein may utilize the aspiration catheter and separator described in U.S. Patent Application No. 2010/0204672 to Lockhart et al. ("Lockhart") published Aug. 12, 2010, which is incorporated herein by reference in its entirety for all purposes.

Any of the embodiments described herein may utilize the surgical instrument having a cutter described in U.S. Patent Application No. 2007/0225739 to Pintor et al. ("Pintor") published Sep. 27, 2007, which is incorporated herein by reference in its entirety for all purposes.

Other contemplated embodiments of an assisted aspiration system 510 which may be utilized are disclosed in U.S. Patent Application No. 2010/0094201 to Mallaby ("Mallaby") published Apr. 15, 2010, which is incorporated herein by reference in its entirety for all purposes. Other contemplated aspiration catheters which may be utilized are disclosed in U.S. Patent Application No. 2008/0255596 to Jenson et al. ("Jenson") published Oct. 16, 2008, which is incorporated herein by reference in its entirety for all purposes.

While embodiments have been shown and described, various modifications may be made without departing from the scope of the inventive concepts disclosed herein.

What is claimed is:

1. An aspiration system for removal of material from a lumen, cavity or duct of a patient, comprising:
   an aspiration catheter having a proximal end and a distal end and configured to be inserted through a lumen of an elongate tubular member, the elongate tubular member configured for insertion into the vasculature of a subject and having a proximal end and a distal end, the lumen of the elongate tubular member extending from the proximal end to the distal end, and an inner surface defined by the lumen of the elongate tubular member, the aspiration catheter comprising:
      a tubular aspiration member having a proximal end, a distal end, and a lumen, and configured to at least partially extend out of the lumen of the elongate tubular member at the distal end of the elongate tubular member and into the vasculature of the subject;
      an elongate support member coupled to the tubular aspiration member and extending between the proximal end of the aspiration catheter and the proximal end of the tubular aspiration member; and
      a composite annular sealing member carried by the tubular aspiration member and configured to create a liquid seal against the inner surface of the elongate tubular member, wherein the composite annular sealing member comprises an o-ring and an elastomeric coating, the o-ring carried on an outer surface of the tubular aspiration member and the elastomeric coating covering an outer diameter of the o-ring and covering the outer surface of the tubular aspiration member immediately proximal to the o-ring and immediately distal to the o-ring, the elastomeric coating extending continuously from the outer surface of the tubular aspiration member proximal to the o-ring to the outer surface of the tubular aspiration member distal to the o-ring.

2. The aspiration system of claim 1, wherein the elastomeric coating comprises polyurethane.

3. The aspiration system of claim 1, wherein the elastomeric coating comprises a thermoplastic elastomer.

4. The aspiration system of claim 1, wherein the elastomeric coating is a dip coating.

5. The aspiration system of claim 1, wherein the elastomeric coating has a thickness of 0.001 inches or less.

6. The aspiration system of claim 1, wherein o-ring is secured such that it is not configured to significantly move longitudinally in relation to the tubular aspiration member.

7. The aspiration system of claim 1, wherein the o-ring comprises an elastomer selected from the list consisting of: EPDM, silicone, and Buna-N.

8. The aspiration system of claim 1, wherein the o-ring comprises a substantially non-elastomeric material.

9. The aspiration system of claim 1, wherein the elastomeric coating covers the o-ring and the outer surface of the tubular aspiration member over a total longitudinal distance of between 0.38 cm and 20 cm.

10. The aspiration system of claim 1, wherein the elastomeric coating covers the o-ring and the outer surface of the tubular aspiration member over a total longitudinal distance of between 0.38 cm and 2 cm.

11. The aspiration system of claim 1, wherein the composite annular sealing member has a first outer diameter over the elastomeric coating and the o-ring and a second outer diameter over the elastomeric coating longitudinally adjacent the o-ring, the first outer diameter greater than the second outer diameter.

12. The aspiration system of claim 11, further comprising a diametric transition between the first outer diameter and the second outer diameter.

13. The aspiration system of claim 1, wherein the elastomeric coating comprises shrink tubing.

14. The aspiration system of claim 13, wherein the shrink tubing comprises PEBAX shrink tubing.

15. The aspiration system of claim 1, wherein the aspiration catheter further comprises:
   a high pressure injection lumen extending within the elongate support member and having a proximal end adjacent the proximal end of the aspiration catheter and a distal end adjacent the distal end of the tubular aspiration member; and
   at least one orifice located at the distal end of the high pressure injection lumen configured to allow liquid injected through the high pressure injection lumen to be released into the lumen of the tubular aspiration member.

16. The aspiration system of claim 15, wherein the distal end of the high pressure injection lumen includes a curved portion configured to change a direction of fluid flow through the high pressure injection lumen by at least about 90°.

17. The aspiration system of claim 1, further comprising a guiding catheter configured for insertion into the vasculature of a subject and having a proximal end, a distal end, and a lumen, the lumen of the guiding catheter extending from the proximal end to the distal end, the guiding catheter further comprising a guiding catheter lumen inner surface defined by the lumen of the guiding catheter, wherein the composite annular sealing member is further configured to create a liquid seal against the inner surface of the guiding catheter, the guiding catheter further comprising a connector at its proximal end configured for coupling the lumen of the guiding catheter to a vacuum source.

18. An aspiration catheter having a proximal end and a distal end and configured to be inserted through a lumen of an elongate tubular member, the elongate tubular member configured for insertion into the vasculature of a subject and having a proximal end and a distal end, the lumen of the elongate tubular member extending from the proximal end to the distal end, and an inner surface defined by the lumen of the elongate tubular member, the aspiration catheter comprising:
   a tubular aspiration member having a proximal end, a distal end, and a lumen, and configured to at least partially extend out of the lumen of the elongate tubular member at the distal end of the elongate tubular member and into the vasculature of the subject;
   an elongate support member having a proximal end and a distal end, the elongate support member coupled to the tubular aspiration member and extending between the proximal end of the aspiration catheter and the proximal end of the tubular aspiration member, the elongate support member having a first outer diameter at its distal end;
   a tubular extension having a proximal end and a distal end, the proximal end of the tubular extension connected to the distal end of the elongate support member and the distal end of the tubular extension connected to the tubular aspiration member, the tubular extension having a second outer diameter, the second outer diameter less than the first outer diameter of the distal end of the elongate support member; and an annular sealing member carried by the tubular aspiration member and configured to create a liquid seal against the inner surface of the elongate tubular member, wherein the proximal end of the tubular aspiration member comprises an angled proximal opening to the lumen of the tubular aspiration member, wherein the lumen of the tubular aspiration member distal to the angled proximal opening has a luminal cross-sectional area and wherein the angled proximal opening of the lumen of the tubular aspiration member has a proximal opening area, the luminal cross-sectional area less than the proximal opening area.

19. The aspiration catheter of claim 18, wherein the elongate support member comprises a lumen, and therein the tubular extension extends from within the lumen of the elongate support member.

20. The aspiration catheter of claim 19, wherein the proximal end of the tubular extension is bonded to the elongate support member.

* * * * *